(12) United States Patent
Huang et al.

(10) Patent No.: US 11,766,193 B2
(45) Date of Patent: Sep. 26, 2023

(54) BIOSENSOR AND METHOD FOR DETERMINING DIMENSION OF COUNTER ELECTRODE AND PROLONGING USAGE LIFETIME OF THE SAME

(71) Applicant: BIONIME CORPORATION, Taichung (TW)

(72) Inventors: Chun-Mu Huang, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 261 days.

(21) Appl. No.: 16/983,055

(22) Filed: Aug. 3, 2020

(65) Prior Publication Data

US 2021/0030338 A1 Feb. 4, 2021

Related U.S. Application Data

(60) Provisional application No. 62/988,549, filed on Mar. 12, 2020, provisional application No. 62/882,162, filed on Aug. 2, 2019.

(51) Int. Cl.
*A61B 5/145* (2006.01)
*A61B 5/1486* (2006.01)
*A61B 5/1473* (2006.01)

(52) U.S. Cl.
CPC ........ *A61B 5/14503* (2013.01); *A61B 5/1451* (2013.01); *A61B 5/1473* (2013.01);
(Continued)

(58) Field of Classification Search
CPC .............. A61B 5/1451; A61B 5/14532; A61B 5/14564; A61B 5/14865; A61B 5/1495;
(Continued)

(56) References Cited

U.S. PATENT DOCUMENTS 6,002,954 A * 12/1999 Van Antwerp ......... G01N 33/66
600/317
6,068,743 A 5/2000 Fleckenstein
(Continued)

FOREIGN PATENT DOCUMENTS

WO 2019004585 A1 1/2019

OTHER PUBLICATIONS

EPO, Extended European Search Report for European Patent Application No. 20189170.2. dated Dec. 23, 2020. 11 pages.

*Primary Examiner* — Tse W Chen
*Assistant Examiner* — Alice Ling Zou
(74) *Attorney, Agent, or Firm* — Perkins Coie LLP; Viola Kung; Gautam Thatte

(57) ABSTRACT

A biosensor for measuring a physiological signal representative of a physiological parameter associated with an analyte is described. The biosensor includes a working electrode and a counter electrode. The counter electrode including a silver and a silver halide having an initial amount, wherein the initial amount is determined by the following steps of defining a required consumption range of the silver halide during at least one of the measurement periods performed by the biosensor; and determining the initial amount based on a sum of an upper limit of the required consumption range and a buffer amount, so that a required replenishment amount range of the silver halide during the replenishment period is controlled to be sufficient to maintain an amount of the silver halide within a safe storage range.

15 Claims, 36 Drawing Sheets

(52) U.S. Cl.
CPC ...... *A61B 5/14532* (2013.01); *A61B 5/14546*
(2013.01); *A61B 5/14735* (2013.01); ***A61B
5/14865*** (2013.01); *A61B 2560/0223*
(2013.01); *A61B 2560/0468* (2013.01); *A61B
2562/028* (2013.01); *A61B 2562/0215*
(2017.08); *A61B 2562/125* (2013.01); *A61B
2562/16* (2013.01)

(58) Field of Classification Search
CPC .... A61B 2562/12–125; A61B 2560/02; A61B
2560/0266; A61B 2560/063; A61B
2562/0295; G01N 27/301; G01N
27/3272; G01N 27/3274; G01N 27/3273;
G01N 27/38; C12Q 1/006
See application file for complete search history.

(56) References Cited

U.S. PATENT DOCUMENTS

| | | | |
|---|---|---|---|
| 2003/0135100 A1* | 7/2003 | Kim | A61B 5/1486 |
| | | | 600/365 |
| 2009/0298104 A1 | 12/2009 | Liu et al. | |
| 2013/0245412 A1* | 9/2013 | Rong | A61B 5/14532 |
| | | | 600/347 |
| 2018/0100826 A1* | 4/2018 | Marquant | G01N 27/301 |
| 2018/0280691 A1* | 10/2018 | Ackermann | A61N 1/20 |
| 2021/0015407 A1* | 1/2021 | Bohm | A61B 5/685 |
| 2021/0030342 A1* | 2/2021 | Huang | A61B 5/1451 |

\* cited by examiner

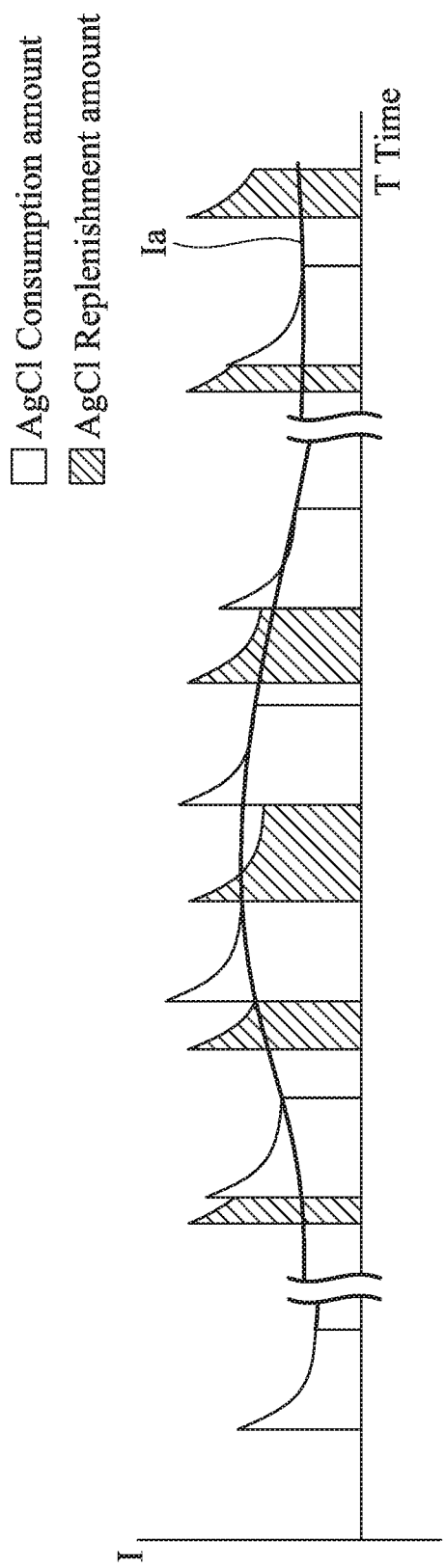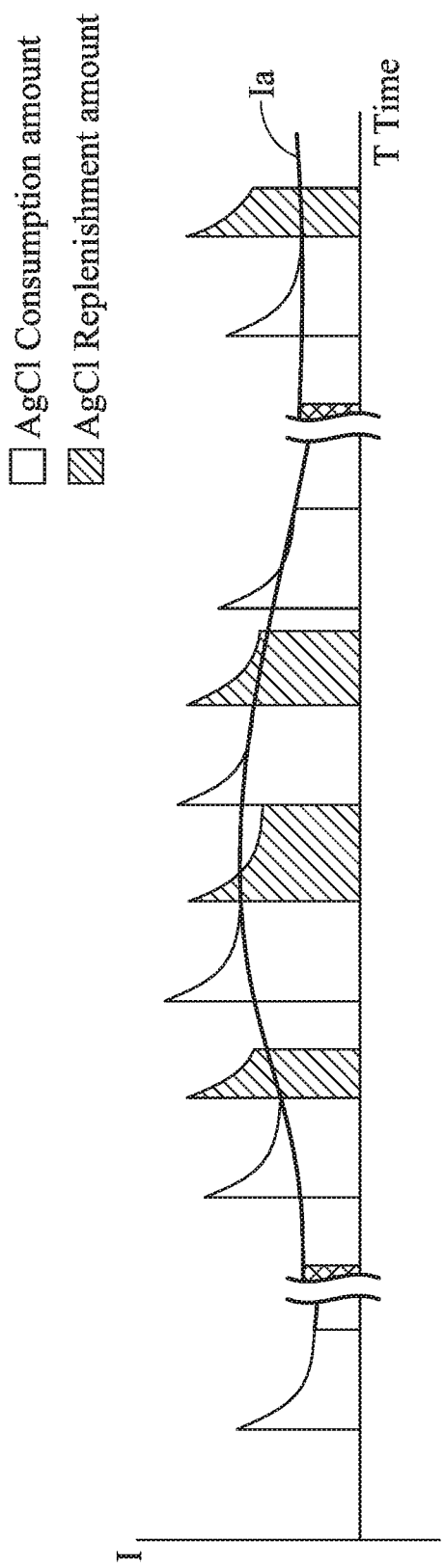

BIOSENSOR AND METHOD FOR DETERMINING DIMENSION OF COUNTER ELECTRODE AND PROLONGING USAGE LIFETIME OF THE SAME

CROSS-REFERENCE TO RELATED APPLICATION AND CLAIM OF PRIORITY

This application claims the benefit of the U.S. Provisional Patent Application No. 62/882,162, filed on Aug. 2, 2019, and the U.S. Provisional Patent Application No. 62/988,549, filed on Mar. 12, 2020 at the U.S. Patent and Trademark Office, the disclosures of which are incorporated herein in their entirety by reference.

FIELD OF THE INVENTION

The present disclosure is related to a biosensor and a method for determining a dimension of a counter electrode of the same. In particular, the present disclosure is related to a biosensor for measuring a physiological signal representative of a physiological parameter associated with an analyte, and a method for prolonging a usage lifetime of the biosensor.

BACKGROUND OF THE INVENTION

The population of diabetic patients is growing rapidly, and there is increasing emphasis on the need to monitor glucose changes in the human body. Therefore, many studies have begun to develop a system that can be implanted in the human body for continuous glucose monitoring (CGM) system to solve the inconvenience to the patient resulting from the repeated blood samplings and detections performed each day.

In the field of an enzyme-based biosensor of CGM system in which a biochemical reaction signal that depends on the concentration of an analyte is converted into a measurable physical signal, such as an optical or electrochemical signal. In case of a measurement of glucose, the electrochemical reaction occurs so that the glucose oxidase (GOx) catalyzes the glucose to react and produce the gluconolactone and the reduced enzyme. Then, the reduced enzyme transfers electrons to the oxygen in the biofluid in the living body to produce a product hydrogen peroxide ($H_2O_2$), and the concentration of the glucose is quantified by oxidizing the product $H_2O_2$. The reaction is as follows:

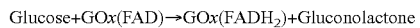

Glucose+GOx(FAD)→GOx(FADH$_2$)+Gluconolactone

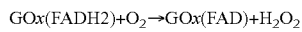

GOx(FADH2)+O$_2$→GOx(FAD)+H$_2$O$_2$ wherein the FAD (which is Flavin Adenine Dinucleotide) is an active center of the GOx.

A user usually wears the CGM system for a long period of time, for example at least 14 days, thus the miniaturization of its size is a necessary development. The basic structure of a CGM system comprises: (a) a biosensor, which measures the physiological signals corresponding to the glucose concentration in the human body; and (b) a transmitter for transmitting these physiological signals. The biosensor may be a two-electrode system or a three-electrode system. The biosensor with a three-electrode system includes a working electrode (WE), a counter electrode (CE), and a reference electrode (RE). The biosensor with a two-electrode system includes a working electrode (WE) and a counter electrode (CE), in which the counter electrode also functions as a reference electrode, and is sometimes called a counter/reference electrode (R/C) accordingly. For the reference electrode in the biosensor with the three-electrode system and for the counter electrode also functioning as a reference electrode in the biosensor with the two-electrode system, a suitable material applicable for a stable measurement to the concentration of the glucose is silver and silver chloride (Ag/AgCl). However, after the biosensor is implanted into a living body, when an oxidation-reaction occurs on the working electrode to measure the concentration of the glucose, a reduction reaction occurs on the corresponding reference electrode (R) or reference/counter electrode (R/C) to cause the AgCl to be reduced to Ag and the AgCl is consumed. In addition, if the biosensor implanted into the living body is a biosensor with the two or three-electrode system, the depletion of the silver chloride from the reference electrode will occur due to its dissolution in the body fluid, and will cause a drifting problem to the reference voltage. However, due to the reaction of the reference/counter electrode (R/C) of the two-electrode system, the consumption of silver chloride is even higher than that of the three-electrode system. Therefore, the usage lifetime of the biosensor is limited by the content of the silver chloride on the counter electrode and/or the reference electrode.

There are also many inventions proposed to address this problem. Taking a biosensor with a two-electrode system as an example, the consumption on the counter electrode is about 1.73 millicoulombs (mC) per day at an average sensing current of 20 nanoamperes (nA). Assuming that the length, width and height of the counter electrode are 3.3 mm, 0.25 mm and 0.01 mm respectively and the originally designed electrode capacity is only 6 mC, the stable measurement that the biosensor can provide can be maintained for about one day at most. However, if it is necessary to further prolong the usage lifetime of the biosensor so that the subcutaneously implanted biosensor can support continuous glucose monitoring for 16 days, the capacity of the counter electrode must be at least 27.68 mC. Without changing the width and thickness of the counter electrode, the length of the counter electrode in the prior art needs to be up to 15.2 mm. Accordingly, the length of the counter electrode of the biosensor has been extended to be larger than 10 mm in the prior art. However, in order to avoid such a kind of biosensor being implanted deeply into the subcutaneous tissues, the biosensor needs to be implanted at an oblique angle. Therefore, it causes problems such as a larger implantation wound and a higher risk of infection to the patient, and because the implantation length is long, the pain during implantation is also more significant.

U.S. Pat. No. 8,620,398 describes a biosensor, which is mainly with a three-electrode system. Although the reference electrode basically does not participate in the chemical reaction, the silver chloride is still gradually consumed naturally in the environment in vivo, the consumption rate is slower than that in the counter electrode of the two-electrode system. The specification disclosed that the AgCl regenerates when the AgCl is almost totally consumed. That is to say, until the measured signals are unstable, or until the measured signals are all noises, the replenishment process will be activated to recover the AgCl back to having the amount sufficient to perform a plurality of measurements. Then, until next time when the noise occurs again, AgCl needs to be replenished again. It can be understood that, although U.S. Pat. No. 8,620,398 considers that AgCl will be consumed in the measurement and replenishing AgCl when the biosensor fails, the measured value at the time of failure can no longer be trusted. It is necessary to wait for the biosensor to complete the AgCl replenishment procedure so as to obtain the correct measured value, to temporarily perform the measurement by taking a blood sample, or to skip this measurement directly. This problem is always troublesome for the patient or those who need to know the present concentration of the blood glucose. In addition, because the biosensor has to deal with a plurality of measurements of consecutive several measurements or over several days, more AgCl capacity must be prepared. However, it will inevitably result in the problem of a longer implantation length of the biosensor. U.S. Pat. No. 8,620,398 has not proposed anything about the timely AgCl replenishment method that can provide uninterrupted measurements, and a shorter implantation length and a longer usage lifetime of the biosensor.

U.S. Pat. No. 9,351,677 proposes a sensor to measure an analyte, which is mainly with a two-electrode system, The reference/counter electrode (R/C) participates in the chemical reaction, so the silver chloride is consumed by the electrochemical reaction. The patent disclosed an analyte sensor with an increased AgCl capacity. The sensor uses $H_2O_2$ to regenerate AgCl on the reference electrode. However, because $H_2O_2$ is easily reduced to $H_2O$ or oxidized to $O_2$, it is not easy to be stably present in the human body. Therefore, during the regeneration/replenishment period, the concentration of $H_2O_2$ in the human body may not be enough to stably replenish a sufficient amount of AgCl, and the biosensor needs to be equipped with a larger AgCl electrode size, and the implantation end is also up to 12 mm long.

In addition, the usage lifetime of the biosensor depends on the amount of the silver halide present in the counter electrode. However, the dimension of the counter electrode also depends on the amount of the silver halide. The longer the life of the biosensor is, the larger the amount of the silver halide is. The larger the amount of the silver halide is, the larger the dimension of the counter electrode is. The larger the dimension of the counter electrode is, the longer the implantation length to the patient is. The longer the implantation length to the patient is, the more discomfort the patient suffers. The present disclosure provides a solution to reduce the dimension of the counter electrode and provides a method to quantify the initial amount of the silver halide required on the counter electrode.

Therefore, the present disclosure provides a biosensor, which is capable of achieving the effects of providing uninterrupted measurements by replenishing AgCl after measuring, stably replenishing AgCl, prolonging the usage lifetime of the biosensor, and miniaturizing the implantation end of the biosensor to a compact size, and reducing the manufacturing cost of the product. These effects can solve the aforementioned problems that the prior art has found impossible to overcome.

In view of the above, because of the defect in the prior art, the inventors provide the present invention to effectively overcome the disadvantages of the prior art. The descriptions of the present invention are as follows:

SUMMARY OF THE INVENTION

By the replenishing technique in the present invention, the micro biosensors in the present invention have a prolonged usage lifetime and the size of the signal sensing section of the counter electrode in the micro biosensor can be reduced, which can reduce biological toxicity. In addition, the reduced size of the electrode specifically refers to the shortened length of the implantation end of the sensor, which would reduce pain for the user during implantation. The device including four electrodes in the present invention can provide more flexible and efficient operation modes.

In accordance with another aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes a working electrode and a counter electrode, the working electrode is at least partially covered by a chemical reagent configured to react with the analyte, and the counter electrode has silver and a silver chloride. The method includes the following cyclic steps of: a) performing a measurement step, including sub-steps of: i. applying a measurement potential difference across the working electrode and the counter electrode so that the working electrode has a higher voltage than that of the counter electrode during a measurement period, causing a first oxidation reaction to occur on the working electrode having an electrochemical reaction with the chemical reagent and the analyte, thereby the working electrode outputs a physiological signal, where the silver halide of the counter electrode has a consumption amount corresponding to the physiological signal; and ii. removing the measurement potential difference to stop the physiological signal measurement step, and converting the physiological signal to output a physiological parameter; and b) performing a replenishment step, including sub-steps of: i. applying a replenishment potential difference across the counter electrode and the working electrode during a replenishment period so that the counter electrode has a higher voltage than that of the working electrode, causing a second oxidation reaction to occur to the silver on the counter electrode, so that the silver chloride gains a replenishment amount, wherein the replenishment amount is related to the consumption amount that the silver halide of the counter electrode has an amount maintained in a safe storage range, and a next physiological signal and a next physiological parameter obtained in a next measurement step are kept in a stable correlation; and ii. removing the replenishment potential difference to stop the replenishment step.

In accordance with one more aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes a working electrode and a counter electrode, the working electrode is at least partially covered by a chemical reagent, and the counter electrode includes silver and a silver halide having an initial amount. The method comprising cyclic steps of: applying a measurement voltage to drive the working electrode to measure the physiological signal, thereby obtaining the physiological parameter, where the silver halide is consumed by a specific amount; stopping applying the measurement voltage; and whenever the physiological parameter is obtained, applying a replenishment voltage to drive the counter electrode to cause an oxidation reaction, thereby the silver halide of a replenishment amount being replenished to the counter electrode, wherein a guarding value of a sum of the replenishment amount and the initial amount subtracting the consumption amount is controlled within a range of the initial amount plus or minus a specific value.

In accordance with one more aspect of the present disclosure, a micro biosensor for implanting subcutaneous implantation to measure a physiological parameter representative of a physiological signal associated with an analyte in a living body is provided. The micro biosensor includes: a substrate; a chemical reagent; a working electrode disposed on the substrate, at least partially covered by the chemical reagent, and driven for a first oxidation reaction to measure the physiological signal for obtaining the physiological parameter within a measurement period; a counter electrode disposed on the substrate, and including a silver and a silver halide having an initial amount and being consumed in a specific amount within the measurement period; and whenever the respective physiological parameter is obtained, driving the counter electrode for a second oxidation reaction within a replenishment period, thereby the silver halide of a replenishment amount being replenished to the counter electrode, wherein a guarding value of a sum of the replenishment amount and the initial amount subtracting the consumption amount is controlled within a range of the original amount plus or minus a specific value.

In accordance with another aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes a working electrode, a counter electrode and an auxiliary electrode, the working electrode being at least partially covered by a chemical reagent configured to react with the analyte, the counter electrode having silver and a silver halide. The method includes the following steps of: a) performing a measurement step, including sub-steps of: i. applying a measurement potential difference across the working electrode and the counter electrode so that the working electrode has a higher voltage level than that of the counter electrode during a measurement period, for causing a first oxidation reaction to occur on the working electrode having an electrochemical reaction with the chemical reagent and the analyte to output a current physiological signal, where the silver halide of the counter electrode has a current consumption amount corresponding to the current physiological signal; and ii. removing the measurement potential difference to stop the measurement step, and operating the current physiological signal to output a current physiological parameter; b) performing a replenishment step, including sub-steps of: i. applying a replenishment potential difference across the counter electrode and the auxiliary electrode during a replenishment period so that the counter electrode has a higher voltage level than that of the auxiliary electrode, causing a second oxidation reaction to occur to the silver on the counter electrode, so that the silver halide gains a replenishment amount corresponding to the consumption amount so that the silver halide of the counter electrode has an amount maintained in a safe storage range, and a next physiological signal and a next physiological parameter obtained in a next measurement step are kept in a specific correlation; and ii. removing the replenishment potential difference to stop the replenishment step; c) performing a next measurement step including the same sub-steps as those in the step a); and d) performing a next replenishment step including the same sub-steps as those in the step b).

In accordance with one more aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes a working electrode, a counter electrode and an auxiliary electrode, the working electrode being at least partially covered by a chemical reagent, the counter electrode including silver and a silver halide having an initial amount. The method includes cyclic steps of: applying a measurement voltage to drive the working electrode to measure the physiological signal, thereby obtaining the physiological parameter, where the silver halide is consumed by a consumption amount; stopping applying the measurement voltage; and whenever the physiological parameter is obtained, applying a replenishment voltage between the counter electrode and the auxiliary electrode to drive the counter electrode to cause an oxidation reaction, thereby the silver halide of a replenishment amount being replenished to the counter electrode, wherein a guarding value of a sum of the replenishment amount and the initial amount subtracting the consumption amount is controlled within a range of the initial amount plus or minus a specific value.

In accordance with one more aspect of the present disclosure, a micro biosensor for subcutaneous implantation to measure a physiological parameter representative of a physiological signal associated with an analyte in a living body is provided. The micro biosensor includes: a substrate; a chemical reagent; a working electrode disposed on the substrate, at least partially covered by the chemical reagent, and being driven for a first oxidation reaction to measure the physiological signal to obtain the physiological parameter within a measurement period; a counter electrode disposed on the substrate, and including a silver and a silver halide having an initial amount and being consumed with a specific amount within the measurement period; and an auxiliary electrode disposed on the substrate, wherein: whenever the respective physiological parameter is obtained, driving the counter electrode and the auxiliary electrode for a second oxidation reaction within a replenishment period, thereby the silver halide of a replenishment amount being replenished to the counter electrode, wherein a guarding value of a sum of the replenishment amount and the initial amount subtracting the consumption amount is controlled within a range of the original amount plus or minus a specific value.

In accordance with another aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes a first working electrode, a second working electrode, a first counter electrode and a second counter electrode, wherein each working electrode is at least partially covered by a chemical reagent configured to react with the analyte, and each counter electrode has silver and a silver halide. The method includes the following steps of: a) performing a first measurement step, including sub-steps of: i. applying a first measurement potential difference across the first working electrode and the first counter electrode so that the first working electrode has a higher voltage level than that of the first counter electrode during a first measurement period, for causing a first oxidation reaction to occur on the first working electrode having an electrochemical reaction with the chemical reagent and the analyte, thereby the first working electrode outputting a first physiological signal, where the silver halide of the first counter electrode has a first consumption amount corresponding to the first physiological signal; and ii. removing the first measurement potential difference to stop the first measurement step, and operating the first physiological signal to output a first physiological parameter; b) performing a first replenishment step, including sub-steps of: i. applying a first replenishment potential difference across the first counter electrode and one of the first and the second working electrodes during a first replenishment period so that the first counter electrode has a higher voltage level than that of the one of the first and the second working electrodes, for causing a second oxidation reaction to occur to the silver on the first counter electrode so that the silver halide gains a first replenishment amount corresponding to the first consumption amount; and ii. removing the first replenishment potential difference to stop the first replenishment step; c) performing a second measurement step, including sub-steps of: i. applying a second measurement potential difference across one of the first and the second working electrodes and the second counter electrode so that the one of the first and the second working electrodes has a higher voltage level than that of the second counter electrode during a second measurement period, for causing the first oxidation reaction to occur on the one of the first and the second working electrodes having the electrochemical reaction with the chemical reagent and the analyte, thereby the one of the first and the second working electrodes outputting a second physiological signal, where the silver halide of the second counter electrode has a second consumption amount corresponding to the second physiological signal; and ii. removing the second measurement potential difference to stop the second measurement step, and operating the second physiological signal to output a second physiological parameter; d) performing a second replenishment step, including sub-steps of: i. applying a second replenishment potential difference across the second counter electrode and the second working electrode during a second replenishment period so that the second counter electrode has a higher voltage level than that of the second working electrode, for causing the second oxidation reaction to occur to the silver on the second counter electrode so that the silver halide gains a second replenishment amount; and ii. removing the second replenishment potential difference to stop the second replenishment step; and e) repeatedly performing steps like the steps a-b), or c)-d), wherein: the silver halide of each counter electrode has an amount maintained in a safe storage range so that a next physiological signal and a next physiological parameter obtained in a next measurement step are kept in a specific correlation.

In accordance with one more aspect of the present disclosure, a method of measuring an analyte using a biosensor for prolonging a usage lifetime of the biosensor implanted subcutaneously to measure a physiological signal representative of a physiological parameter associated with the analyte in a biofluid is disclosed. The biosensor includes two working electrodes and two counter electrodes disposed on a substrate, wherein each working electrode is at least partially covered by a chemical reagent, each counter electrode includes an electrode material having silver and a silver halide, and each silver halide has an initial amount. The method includes cyclic steps of: applying a measurement voltage to drive one of the two working electrodes at a measurement period to measure the physiological signal, thereby obtaining the physiological parameter, wherein the silver halide of one of the two working electrodes is consumed by a consumption amount; stopping applying the measurement voltage; and applying a replenishment voltage to drive the consumed counter electrode at a replenishment period to replenish the silver halide of a replenishment amount to the consumed counter electrode, wherein: whenever the physiological parameter is obtained, within the replenishment period, a guarding value of a sum of the replenishment amount and the initial amount subtracting the consumption amount is controlled within a range of the initial amount plus or minus a specific value.

In accordance with one more aspect of the present disclosure, an implantation micro biosensor with relatively long usage lifetime and relatively small size of counter electrode for measuring a physiological parameter representative of a physiological signal associated with an analyte in a living body is disclosed. The implantation micro biosensor includes: a substrate; a chemical reagent; two working electrodes disposed on the substrate, wherein each of the working electrodes includes a first signal sensing section at least partially covered by the chemical reagent, and one of the two working electrodes is driven for an oxidation reaction to measure the physiological signal to obtain the physiological parameter within a specific measurement period; and two counter electrodes disposed on the substrate, wherein each of the counter electrodes includes a second signal sensing section having a size and a electrode material having a silver and a silver halide, and the silver halide has an initial amount and is consumed with a consumption amount within the specific measurement period, wherein: whenever the respective physiological parameter is obtained, one of the counter electrodes is driven within a replenishment period, thereby the silver halide of a replenishment amount being replenished to the driven counter electrode, wherein a guarding value of a sum of the replenishment amount and the initial amount subtracting the consumption amount is controlled within a range of the original amount plus or minus a specific value.

In accordance with one aspect of the present disclosure, it provides a method for determining a dimension of a counter electrode of a biosensor and for prolonging a usage lifetime of the biosensor, wherein the counter electrode comprises a silver and a silver halide, the dimension is quantified based on an initial amount of the silver halide being sufficient to measure a physiological signal representative of a physiological parameter associated with an analyte in a living body, the biosensor is implanted subcutaneously into the living body and further includes a working electrode, and the silver halide is consumed during a measurement period and replenished during a replenishment period, the method comprising the following steps of: (a) defining a required consumption range of the silver halide during at least one measurement period performed by the biosensor; (b) determining the initial amount based on a sum of an upper limit of the required consumption range and a buffer amount, so that a required replenishment amount of the silver halide during the replenishment period is safeguarded to be sufficient to maintain an amount of the silver halide within a safe storage range, for ensuring a successful retrieval of and a correct correlation between a next physiological signal and a next physiological parameter in a next measurement period; (c) converting the initial amount into the dimension of the counter electrode; (d) providing the counter electrode with at least the initial amount of the silver halide; (e) measuring the physiological signal and a consumption amount of the silver halide during the measurement period; and if) replenishing the silver halide with a replenishment amount during the replenishment period.

In accordance with another aspect of the present disclosure, it provides a method for determining a dimension of a counter electrode of a biosensor and for prolonging a usage lifetime of the biosensor, wherein the counter electrode comprises a silver and a silver halide, the dimension is quantified based on an initial amount of the silver halide being sufficient to measure a physiological signal representative of a physiological parameter associated with an analyte in a living body, the biosensor is implanted subcutaneously into the living body and further includes a working electrode, and the silver halide is consumed during a measurement period and replenished during a replenishment period, the method comprising the following steps of: (a) defining a required consumption range of the silver halide during at least one the measurement period performed by the biosensor; (b) determining the initial amount based on a sum of an upper limit of the required consumption range and a buffer amount, so that a required replenishment amount of the silver halide during the replenishment period is safeguarded to be sufficient to maintain an amount of the silver halide within a safe storage range, for ensuring a successful retrieval of and a correct correlation between a next physiological signal and a next physiological parameter in a next measurement period; (c) converting the initial amount into the dimension of the counter electrode; (d) providing the counter electrode with at least the initial amount of the silver halide; (e) measuring the physiological signal and a consumption amount of the silver halide during the measurement period; and (f) replenishing the silver halide with a replenishment amount during the replenishment period, wherein the step (d) is performed before the step (e) and after the biosensor is implanted.

In accordance with another aspect of the present disclosure, it provides a biosensor for measuring a physiological signal representative of a physiological parameter associated with an analyte, comprising: a working electrode driven for measuring the physiological signal during a first measurement period; a counter electrode including a silver and a silver halide having an initial amount, wherein the counter electrode consumes the silver halide in a consumption amount during the first measurement period, and during a first replenishment period, the counter electrode and the working electrode are driven to replenish the silver halide, wherein the initial amount is determined by the following steps: (a) defining a required consumption range of the silver halide during at least one measurement period performed by the biosensor; and (b) determining the initial amount based on a sum of an upper limit of the required consumption range and a buffer amount, so that a required replenishment amount range of the silver halide during the replenishment period is controlled to be sufficient to maintain an amount of the silver halide within a safe storage range.

BRIEF DESCRIPTION OF THE DRAWINGS

The above embodiments and advantages of the present invention will become more readily apparent to those ordinarily skilled in the art after reviewing the following detailed descriptions and accompanying drawings.

FIG. 5E shows a current schematic diagram of the constant voltage circuit running in the measurement mode and the replenishment mode by turns in a fifth way.

FIG. 5F shows a current schematic diagram of the constant voltage circuit running in the measurement mode and the replenishment mode by turns in a sixth way.

DETAILED DESCRIPTION OF THE PREFERRED EMBODIMENTS

The present disclosure will now be described more specifically with reference to the following embodiments. It is to be noted that the following descriptions of embodiments of the present disclosure are presented herein for the purposes of illustration and description only; they are not intended to be exhaustive or to be limited to the precise form disclosed.

Unless there are other restrictions defined in the specific example, the following definitions apply to the terms used throughout the specification.

The term "amount" refers to a capacity of silver halide (AgX) or silver chloride (AgCl) on the counter electrode, and preferably represents in a unit of micro Coulomb ($\mu$C), milli Coulomb (mC) or Coulomb (C), but is not limited to concentration by weight percentage (wt %), mole number, molar concentration, etc.

Please refer to all figures of the present invention when reading the following detailed description, wherein all Figures of the present invention demonstrate different embodiments of the present invention by showing examples, and help the skilled person in the art to understand how to implement the present invention. The present examples provide sufficient embodiments to demonstrate the spirit of the present invention, each embodiment does not conflict with the others, and new embodiments can be implemented through an arbitrary combination thereof, i.e., the present invention is not restricted to the embodiments disclosed in the present specification.

Embodiment I

Figure 1:
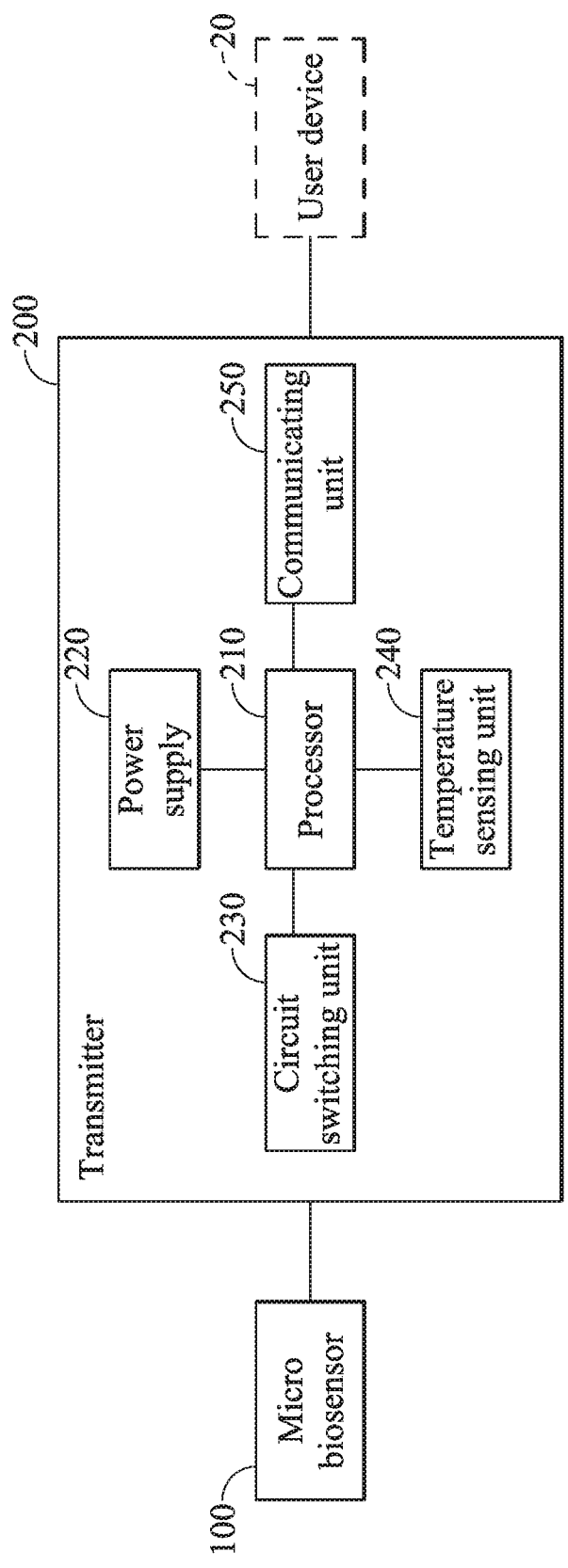
FIG. 1 shows a schematic diagram of a physiological signal measurement device of the present invention.

Please refer to FIG. 1, which is a schematic diagram of a physiological signal measurement device of the present invention. The physiological signal measurement device 10 of the present invention can be implanted subcutaneously to measure a physiological signal representing a physiological parameter associated with an analyte in a biofluid. The physiological signal measurement device 10 of the present invention includes a micro biosensor 100 and a transmitter 200, wherein the transmitter 200 is electrically connected to the micro biosensor 100 and includes a processor 210, a power supply 220, a circuit switching unit 230, a temperature sensing unit 240 and a communicating unit 250. The power supply 220 provides a voltage to the micro biosensor 100 through the circuit switching unit 230 for measuring the physiological signal, the temperature sensing unit 240 measures the body temperature of the living body, thereby the temperature measuring signal and the measured physiological signal measured by the micro biosensor 100 are transmitted to the processor 210, and the processor 210 operates the measured physiological signal to a physiological parameter. The communicating unit 250 can communicate with a user device 20 by a wire or wireless transmission.

Figure 2A:
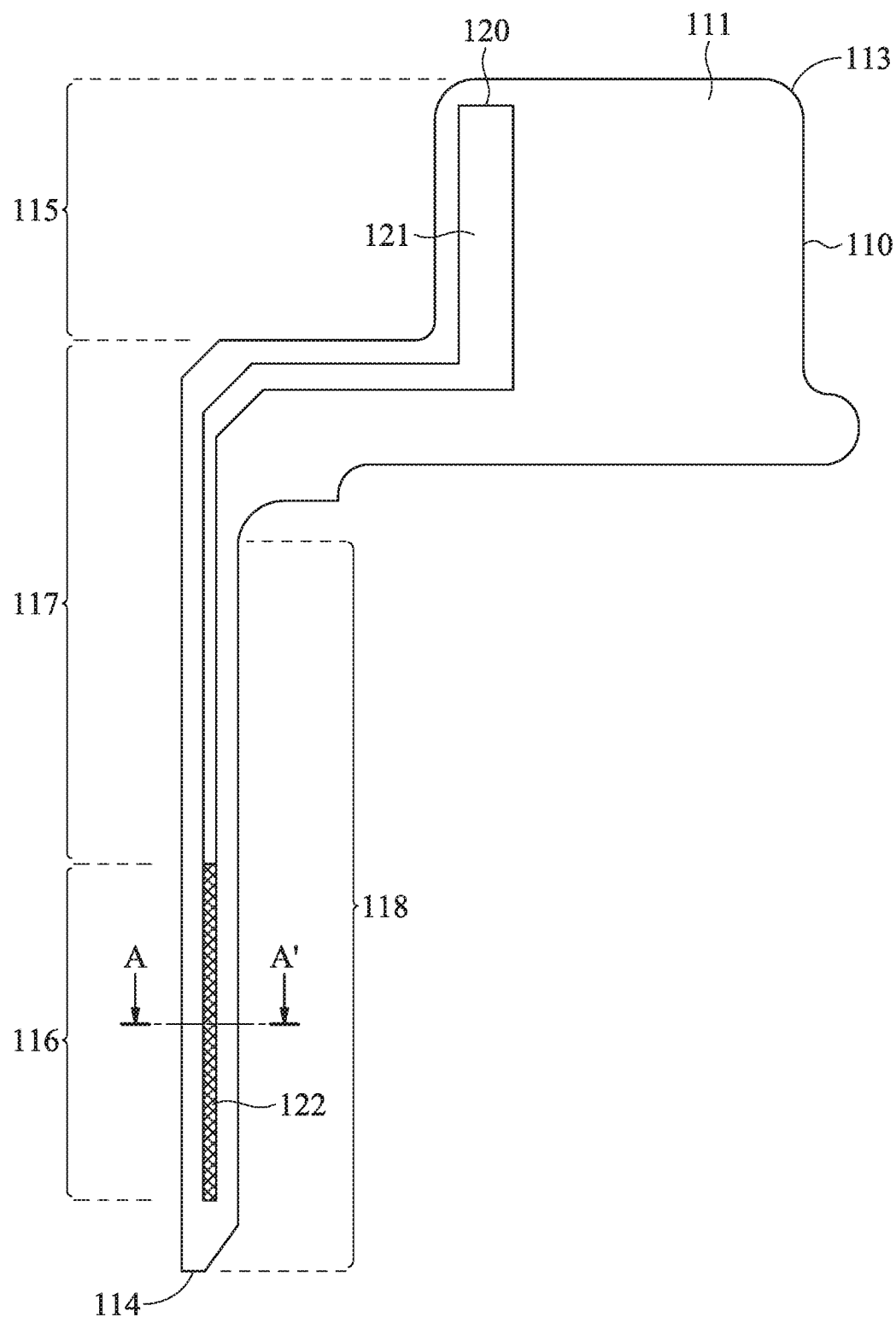
FIG. 2A shows a front schematic diagram of a micro biosensor of the present invention.
Figure 2B:
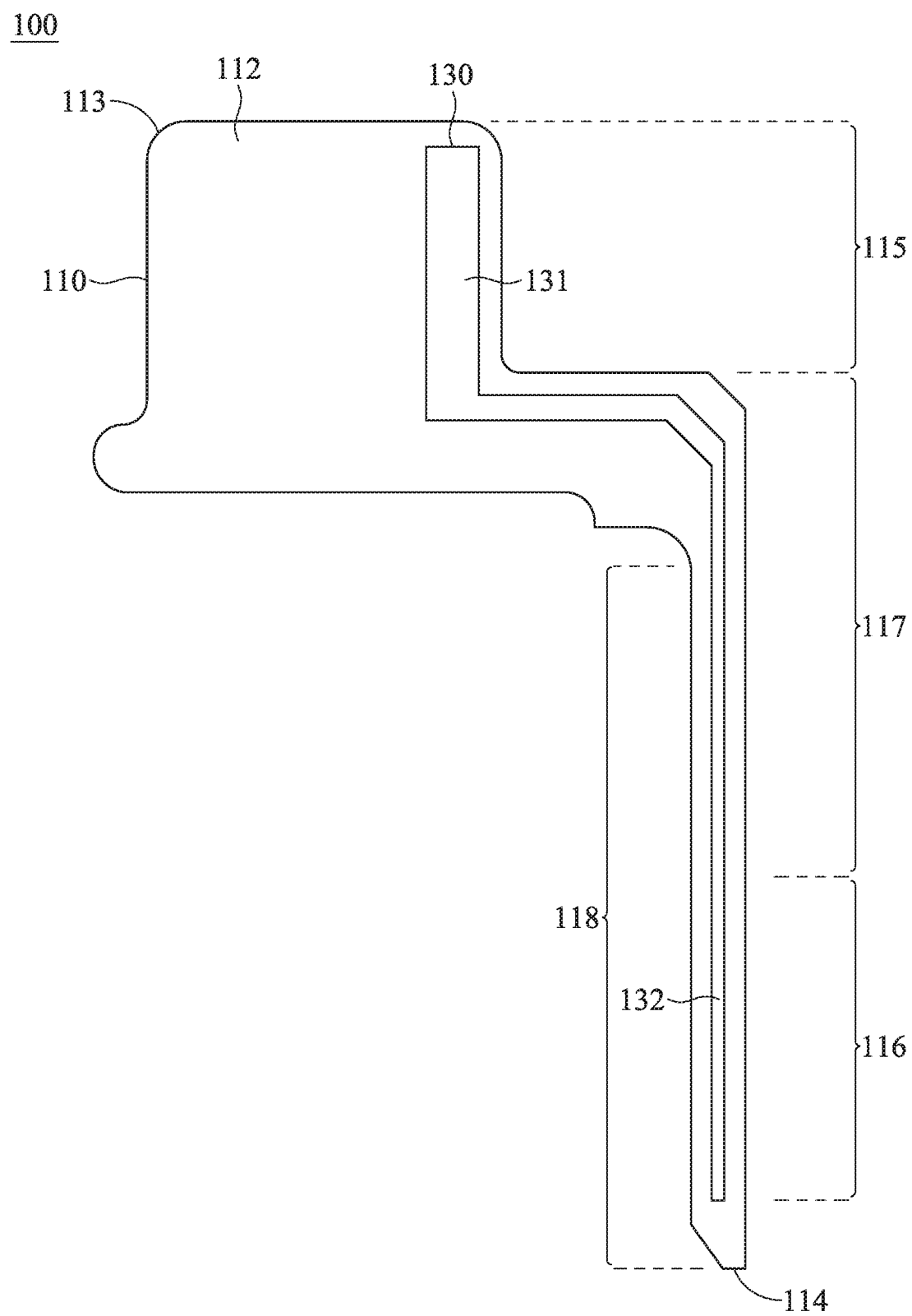
FIG. 2B shows a back schematic diagram of a micro biosensor of the present invention.
Figure 2C:
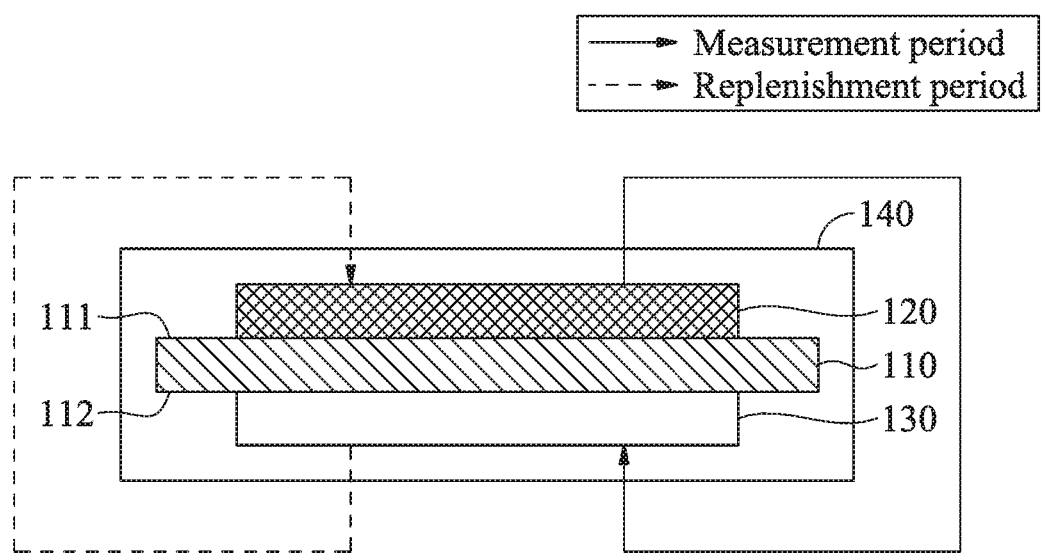
FIG. 2C shows a sectional schematic diagram of a cut view of the micro biosensor along the section line A-A' in FIG. 2A.

Please refer to FIGS. 2A and 2B, which are front and back schematic diagrams of the micro biosensor of the present invention. The micro biosensor 100 of the present invention includes a substrate 110, a working electrode 120 and a counter electrode 130 disposed on the substrate 110, and a chemical reagent 140 (as shown in FIG. 2C) covering the working electrode 120 and the counter electrode 130. The material of the substrate 110 can be any material that is known to be suitable for use in electrode substrates and preferably has flexibility and insulation properties, such as but not limited to: polymer materials such as polyester and polyimide. The aforementioned polymer materials can be used alone or in combination. The substrate 110 includes a surface 111 (i.e. a first surface), an opposite surface 112 (i.e. a second surface) opposite to the surface 111, a first end 113 and a second end 114. The substrate 110 is separated into three areas respectively—they are a signal output area 115 located close to the first end 113, a sensing area 116 located close to the second end 114, and a connecting area 117 located between the signal output area 115 and the sensing area 116. The working electrode 120 is disposed on the surface 111 of the substrate 110 and extended from the first end 113 to the second end 114 of the substrate 110. The working electrode 120 includes a signal output section 121 located in the signal output area 115 of the substrate 110, and a signal sensing section 122 located in the sensing area 116 of the substrate 110. A material of the working electrode 120 includes but is not limited to: carbon, platinum, aluminum, gallium, gold, indium, iridium, iron, lead, magnesium, nickel, manganese, molybdenum, osmium, palladium, rhodium, silver, tin, titanium, zinc, silicon, zirconium, a mixture thereof, or derivatives thereof (such as alloys, oxides or metal compounds, etc.). Preferably, the material of the working electrode 120 is a precious metal, a precious metal derivative or a combination thereof. More preferably, the working electrode 120 is made of platinum-containing material.

The counter electrode 130 is disposed on the opposite surface 112 of the substrate 110 and extended from the first end 113 to the second end 114 of the substrate 110. The counter electrode 130 includes a signal output section 131 located in the signal output area 115 of the substrate 110, and a signal sensing section 132 located in the sensing area 116 of the substrate 110. The material of the surface of the counter electrode 130 includes silver and silver halide, preferably silver chloride or silver iodine. Because the electrode material of the counter electrode 130 of the present invention includes silver and silver halide (Ag/AgX), the counter electrode 130 of the present invention includes functions of the counter electrode and the reference electrode of the common knowledge in the art. Specifically, the counter electrode 130 of the present invention can (1) form an electronic circuit with the working electrode 120 to cause the current between the counter electrode 130 and the working electrode 120 to be conducted to ensure that the electrochemical reaction occurs on the working electrode 120; and (2) provide a stable relative potential as a reference potential. Therefore, the working electrode 120 and the counter electrode 130 of the present invention form a 2-electrode system. In order to further reduce the cost and improve the biocompatibility of the biosensor of the present invention, the Ag/AgX can be used with carbon, for example, the Ag/AgX is mixed into carbon paste, and the content of the silver halide can be an amount that allows the counter electrode 130 to stably perform the measurement step. The surface of the counter electrode 130 can be partially covered by a conductive material to prevent silver halide from the dissolution and to protect the counter electrode 130, wherein the conductive material is selected from the material that does not affect the measuring result of the working electrode. For example, the conductive material is carbon.

In another embodiment, the biosensor is not limited to a wire-type or stacked-type electrode structure.

According to another embodiment of the present disclosure, the initial amount of the silver halide can be zero before the biosensor is ready for shipping out of the plant for sale. In this case the counter electrode 130 of the biosensor has no silver halide. After the biosensor is subcutaneously implanted in the patient and during the first replenishment period before the first measurement, the initial amount of the silver halide can be replenished by oxidizing the silver coated on the electrodes 130.

The chemical reagent 140 at least covers on the surface of the signal sensing section 122 of the working electrode 120. In other embodiment, the chemical reagent 140 further covers on the signal sensing section 132 of the counter electrode 130. That is to say, the counter electrode 130 is not covered by the chemical reagent 140. The sensing area 116 of the micro biosensor 100 can be implanted subcutaneously to cause the signal sensing section 122 of the working electrode 120 to measure the physiological signal of the analyte in the biofluid. The physiological signal is transmitted to the processor 210 through the signal output section 121 of the working electrode 120 to obtain the physiological parameter. In addition, apart from the transmitter 200, the physiological parameter can also be obtained from the user device 20 through the wire/wireless communication. The common user device 20 can be a smartphone, a physiological signal receiver or a blood glucose meter.

Figure 9:
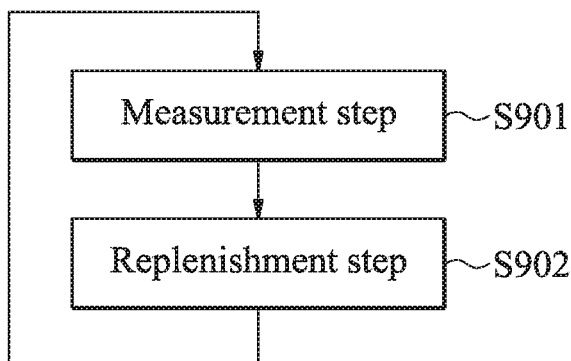
FIG. 9 shows a method of measuring an analyte according to an embodiment in the present invention.

Please refer to FIG. 2C, which is a sectional schematic diagram of a cut view of the micro biosensor along the section line A-A working electrode 120 to measure the physiological signal of the analyte in the bioflicro biosensor 100. In FIG. 2C, the working electrode 120 is disposed on the surface 111 of the substrate 110, the counter electrode 130 is disposed on the opposite surface 112 of the substrate 110, and the surfaces of the working electrode 120 and the counter electrode 130 are covered by the chemical reagent 140. Basically, the chemical reagent 140 covers at least part of the surface of the working electrode 120. The micro biosensor 100 of the present invention performs a measurement step during a measurement period, and performs a replenishment (regeneration) step during a replenishment period. When the measurement step is performed, a voltage level of the working electrode 120 is higher than that of the counter electrode 130, causing a current to flow from the working electrode 120 to the counter electrode 130, so that an oxidation reaction occurs on the working electrode 120 having an electrochemical reaction with the chemical reagent 140 and the analyte and the physiological signal is measured, and a reduction reaction occurs on the counter electrode 130, so that silver halide (AgX) in the counter electrode 130 is consumed and dissociated into silver (Ag) and halide ion ($X^-$). Because the silver halide in the counter electrode 130 is consumed, the silver halide needs to be replenished in the counter electrode 130 to perform the next measurement step. When the replenishment step is performed, the voltage level of the counter electrode 130 is higher than that of the working electrode 120, causing a current to flow from the counter electrode 130 to the working electrode 120, so that an oxidation reaction occurs on the counter electrode 130 to cause silver to combine with halide ion in the living body or Cl− oxidized (or dissociated) from AgCl to replenish silver halide. The detailed measurement step and the detailed replenishment step are illustrated in FIG. 9.

Figure 3:
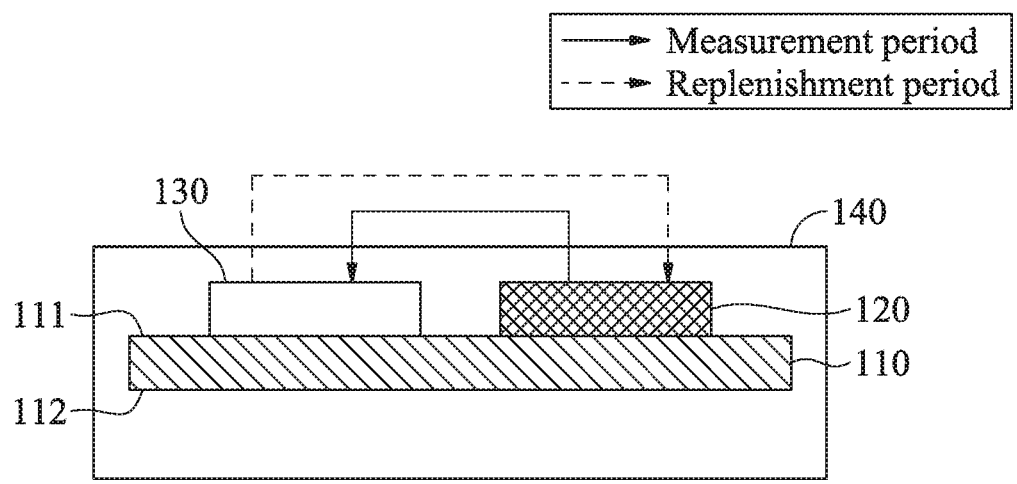
FIG. 3 shows a sectional schematic diagram of a second embodiment of the micro biosensor of the present invention.

In another embodiment, the working electrode 120 and the counter electrode 130 can be disposed on the same surface of the substrate 110. Specifically, both the working electrode 120 and the counter electrode 130 can be disposed on the surface 111 or the opposite surface 112 of the substrate 110, as shown in FIG. 3. Similarly, when the measurement step is performed, a current flows from the working electrode 120 to the counter electrode 130, so that an oxidation reaction occurs on the working electrode 120 and the physiological signal is measured, and silver halide (AgX) in the counter electrode 130 is consumed and dissociated into silver (Ag) and halide ion (X−). When the replenishment step is performed, a current flows from the counter electrode 130 to the working electrode 120, so that an oxidation reaction occurs on the counter electrode 130 to cause the combination of silver and halide ion to replenish silver halide.

In any embodiment above, to prevent the silver electrode material from breakage due to over chlorination, a layer of conductive material, such as carbon, can be further disposed between the opposite surface 112 of the substrate 110 and the silver of the counter electrode 130. However, if the bottom layer of the counter electrode 130 is carbon, the resistance at a switch position will be too high. A conductive layer, such as silver, can be further disposed between the carbon conductive material and the opposite surface 112 of the substrate 110. Therefore, the material of the counter electrode 130 of the present invention sequentially is the conductive layer, the carbon layer and the silver/silver halide layer from the opposite surface 112 of the substrate 110.

Switching Applications of a Constant Voltage Circuit

Figure 4A:
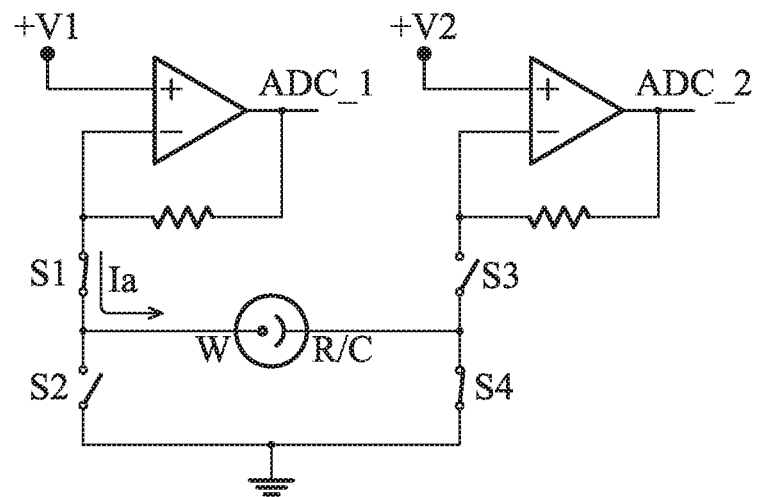
FIG. 4A shows a constant voltage circuit in a measurement mode in the present invention.
Figure 4B:
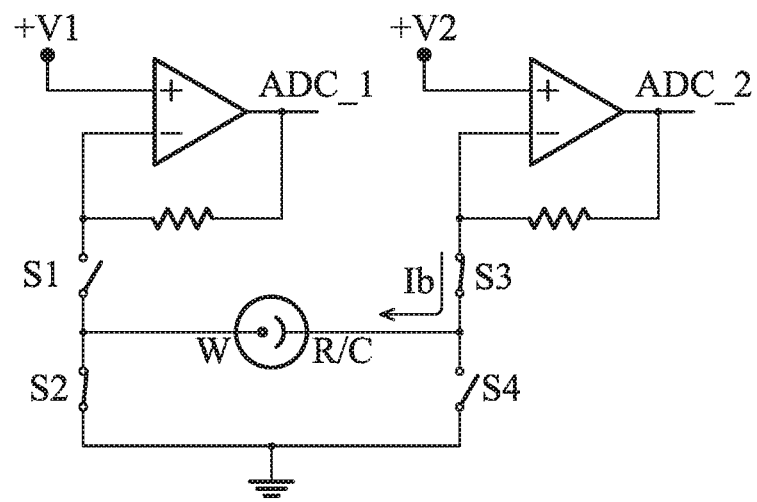
FIG. 4B shows a constant voltage circuit in a replenishment mode in the present invention.

Please refer to FIGS. 4A-4B and FIGS. 5A-5D, wherein FIGS. 4A and 4B show a constant voltage circuit in a measurement mode and a replenishment mode, respectively, in the present invention, and FIGS. 5A-5D respectively show the current schematic diagrams of the constant voltage circuit running in the measurement mode and the replenishment mode by turns in different ways. The measurement mode can be started and stopped by applying a measurement potential difference V1 and removing the measurement potential difference V1, respectively, and the corresponding current is represented by Ia. In the measurement mode, the measurement potential difference V1 is applied across the working electrode W and the counter electrode R/C during the measurement period T1, so that the voltage of the working electrode W is higher than that of the counter electrode R/C. During the measurement mode, as shown in FIG. 4A, the switches S1 and S4 are in the close circuit state, the switches S2 and S3 are in the open circuit state, the working electrode W is +V1, and the counter electrode R/C is grounded, so that at the working electrode W, an oxidation reaction occurs, and the working electrode W electrochemically reacts with chemical reagents and an analyte to output a physiological signal Ia. The AgCl in the counter electrode R/C has a consumption amount corresponding to the physiological signal Ia. As shown in FIGS. 5A-5D, between any two of a plurality of measurement periods T1 is a period T2 during which no measurement is performed. In some preferred embodiments, T2 is a constant value.

The replenishment mode can be started and stopped by applying a replenishment potential difference V2 and removing the replenishment potential difference V2, respectively, and the corresponding current is represented by Ib. V2 is a constant value in a range of 0.1V to 0.8V, preferably range of 0.2V to 0.5V. In the replenishment mode, the replenishment potential difference V2 is applied across the working electrode W and the counter electrode R/C during the replenishment period t2 (t2 is in a range of 0 to T2), so that the voltage of the counter electrode R/C is higher than that of the working electrode W. During the replenishment mode, as shown in FIG. 4B, the switches S1 and S4 are in the open circuit state, the switches S2 and S3 are in the close circuit state, the working electrode W is grounded, and the counter electrode R/C is +V2, so that on the counter electrode R/C, an oxidation reaction of Ag occurs to replenish the counter electrode R/C with AgCl by a replenishment amount. In the constant voltage circuit, the replenishment potential difference V2 is a constant voltage, and the measured output current is Ib. In the present invention, the amount or value of capacity (with the unit "coulomb" and represented by the symbol "C") of AgCl is defined by calculating the area under the current curve, so the consumption amount of AgCl in the measurement mode is Ia*T1, and the replenishment amount of AgCl in the replenishment mode is Ib*t2. In such case, the replenishment amount of AgCl can be controlled by adjusting the period t2 during which the potential difference V2 is applied. In other words, on the premise that the AgCl on the counter electrode R/C is kept within the safe storage range, the replenishment amount can be equal to or not equal to (including approximately similar, greater than or less than) consumption amount.

Figure 5A:
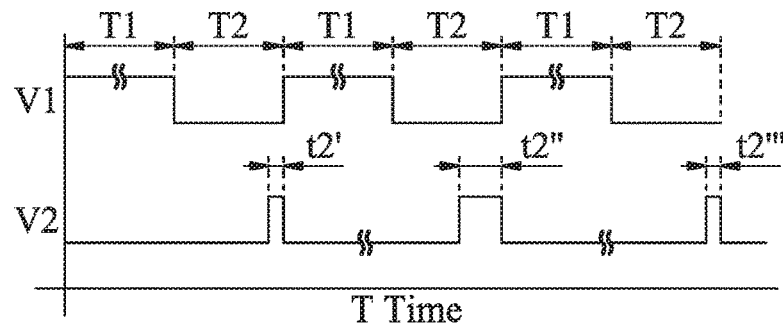
FIG. 5A shows a current schematic diagram of the constant voltage circuit running in the measurement mode and the replenishment mode by turns in a first way.
Figure 5B:
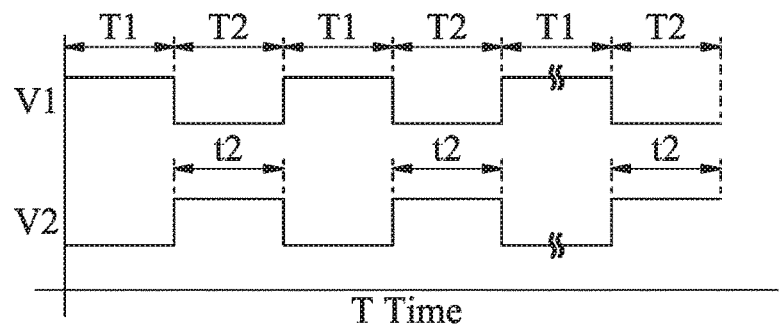
FIG. 5B shows a current schematic diagram of the constant voltage circuit running in the measurement mode and the replenishment mode by turns in a second way.
Figure 5C:
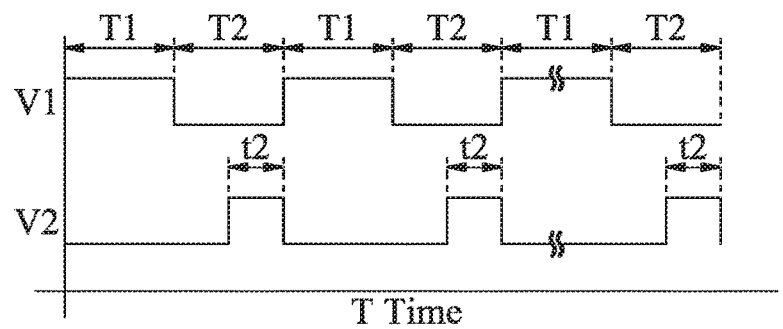
FIG. 5C shows a current schematic diagram of the constant voltage circuit running in the measurement mode and the replenishment mode by turns in a third way.
Figure 5D:
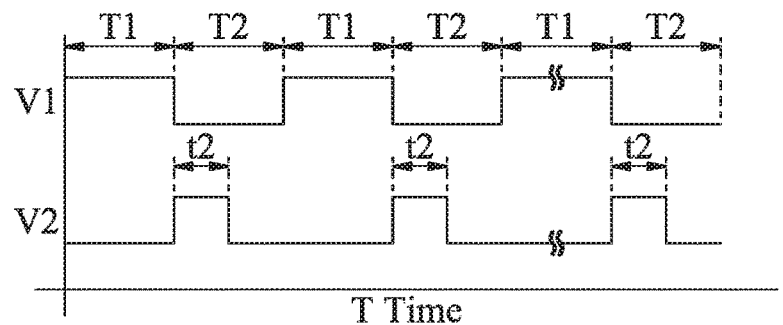
FIG. 5D shows a current schematic diagram of the constant voltage circuit running in the measurement mode and the replenishment mode by turns in a fourth way.

In FIGS. 5A-5D, the horizontal axis represents time, the curve for V1 represents the application and removal of the measurement potential difference V1, and the curve for V2 represents the application and removal of the replenishment potential difference V2. Please refer to FIG. 5A. In a preferred embodiment, both V2 and T2 are constant values, and the period t2 (i.e., the replenishment period) during which V2 is applied is a variable value. The replenishment period t2 is dynamically adjusted in a range of 0 to T2 according to the physiological signal Ia measured in the measurement mode and during the measurement period T1. As shown in FIG. 5A, t2 can be t2t2 of the measurement potential difference V1, and the curperiod t2 can be changed according to the consumption amount of AgCl. In the condition of a high consumption amount of AgCl, the counter electrode R/C can be replenished for a longer time to keep the AgCl on the counter electrode R/C within the safe storage range. For example, the amount of AgCl replenished during t2' t2' C within the safe storage range. AgCl replenished during t2g Please refer to FIG. 5B, in another preferred embodiment, V2, T2 and t2 are all constant values, wherein t2=T2. That is, the measurement mode and replenishment mode alternate seamlessly, and the period during which no measurement is performed is the replenishment period. Please refer to FIGS. 5C and 5D, in some preferred embodiments, V2, T2, and t2 are constant values, wherein t2 is a constant value greater than 0 and less than T2. For example, t2=½ T2, ⅖ T2, ⅗ T2, etc. The difference between FIG. 5C and FIG. 5D is that in FIG. 5C, after each measurement mode, a buffer time (buffer time=T2−t2) is passed before the replenishment mode starts; and in FIG. 5D, after each measurement mode, the replenishment mode starts immediately without any buffer time, and there is a period of time between the end of each replenishment mode and the start of the next measurement mode. In some preferred embodiments, t2 is less than T2, and t2 can be any time period during T2.

Please refer to FIGS. 5E and 5F, which show current-time schematic diagrams of the constant voltage circuit running in the measurement mode and the replenishment mode by turns in different ways. In FIGS. 5E and 5F, the horizontal axis represents time, the vertical axis represents current, and the curve represents the physiological parameter curve calculated from the measured physiological signal Ia. In the two embodiments, similar to that in FIG. 5A, V2 and T2 are constant values and the replenishment period t2 is a variable value. In FIGS. 5E and 5F, the white area under the curve represents the AgCl consumption amount in the measurement mode (Ia*T1), and the oblique area represents the replenishment amount of AgCl in the replenishment mode (Ib*t2). It can be seen from the figures that in order to make Ib*t2 close to Ia*T1 or within a certain range of Ia*T1, the replenishment period t2 is dynamically adjusted in a range of 0 to T2 according to the measured physiological signal Ia and the measurement period T1. According to requirements, the front part (as shown in FIG. 5E) or the back part (as shown in FIG. 5F) of the period (T2) where the measurement mode is not executed can be selected to perform the replenishment mode.

Switching Applications of a Segmental Constant Current Circuit

Figure 6A:
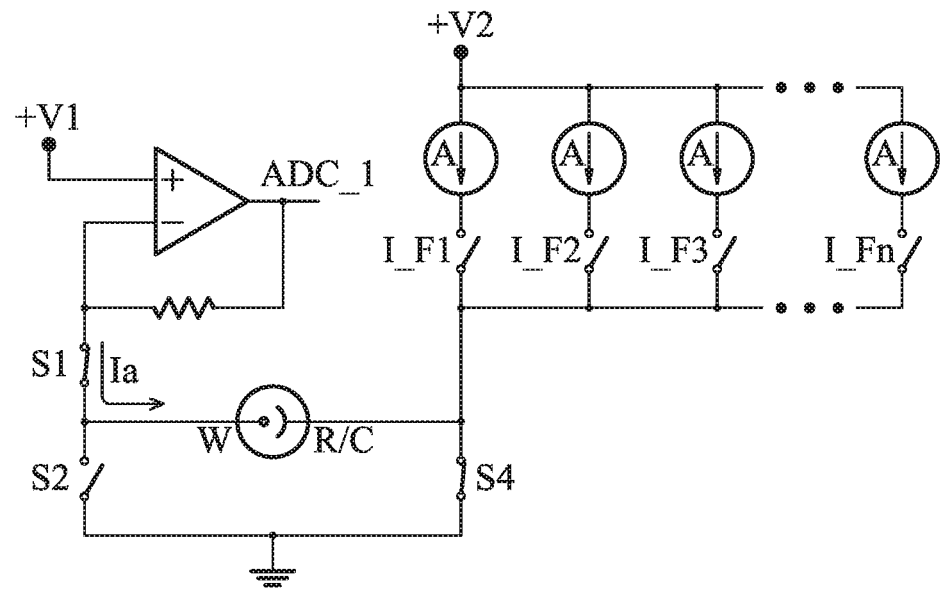
FIG. 6A shows a segmental constant current circuit in a measurement mode in the present invention.
Figure 6B:
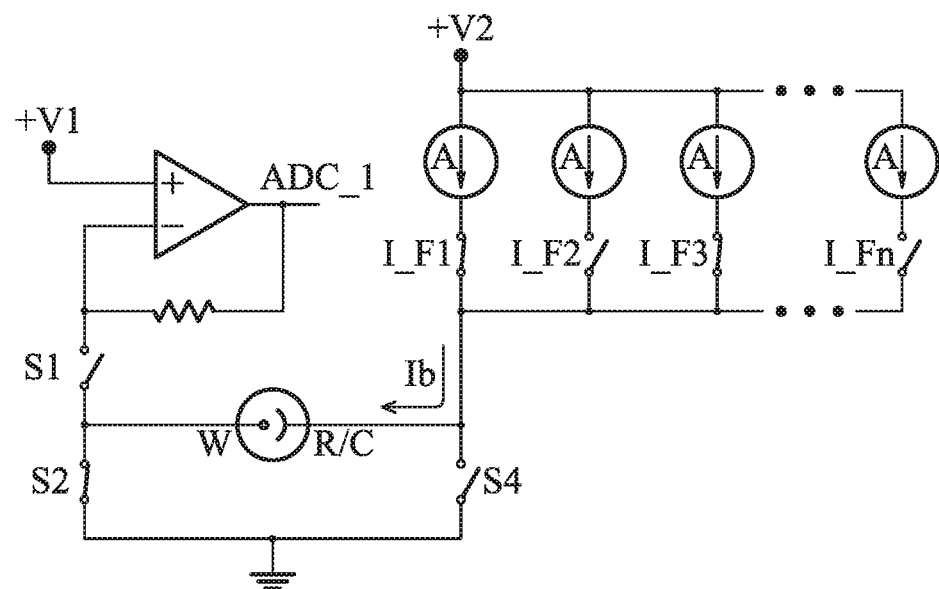
FIG. 6B shows a segmental constant current circuit in a replenishment mode in the present invention.
Figure 8A:
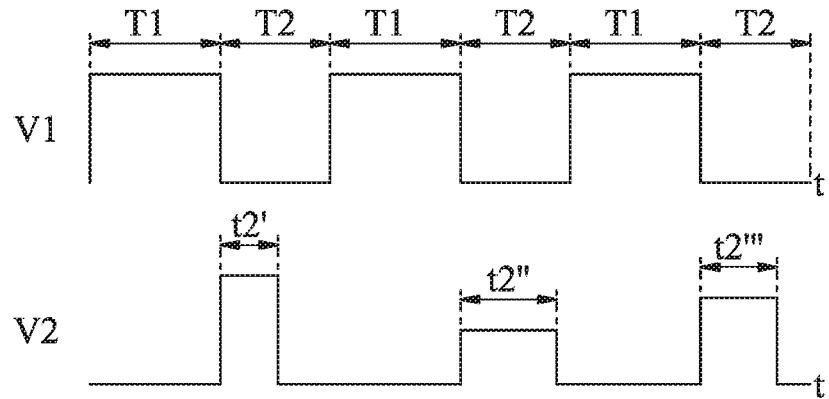
FIG. 8A shows a voltage schematic diagram of the constant current circuit running in the measurement mode and the replenishment mode by turns in a first way.
Figure 8B:
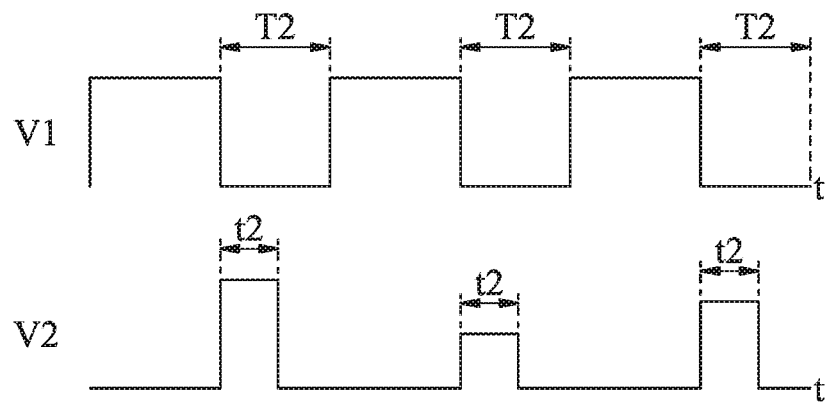
FIG. 8B shows a voltage schematic diagram of the constant current circuit running in the measurement mode and the replenishment mode by turns in a second way.
Figure 8C:
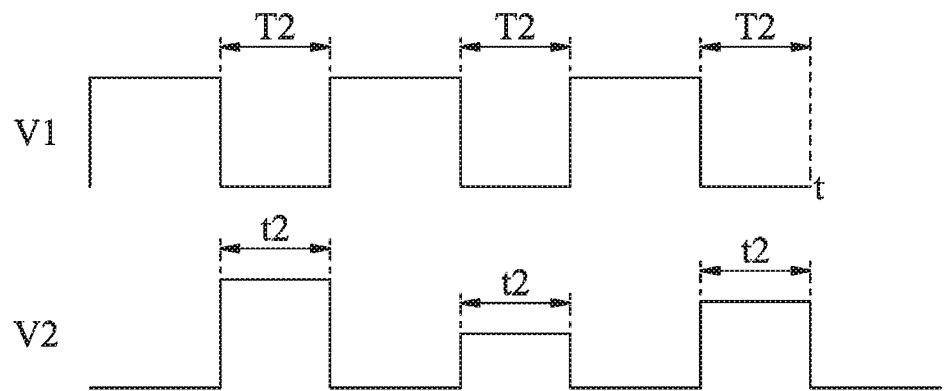
FIG. 8C shows a voltage schematic diagram of the constant current circuit running in the measurement mode and the replenishment mode by turns in a third way.

Please refer to FIGS. 6A-6B and FIGS. 8A-8C, wherein FIGS. 6A and 6B show a segmental constant current circuit in a measurement mode and a replenishment mode, respectively, according to the present invention, and FIGS. 8A-8C respectively show the voltage schematic diagrams of the constant current circuit running in the measurement mode and the replenishment mode by turns in different ways. The measurement mode can be started and stopped by applying a measurement potential difference V1 and removing the measurement potential difference V1, respectively, and the corresponding current is represented by Ia. In the measurement mode, the measurement potential difference V1 is applied across the working electrode W and the counter electrode R/C during the measurement period T1. During the measurement mode, as shown in FIG. 6A, the switches S1 and S4 are in the close circuit state, the remaining switches are in the open circuit state, the working electrode W is +V1, and the counter electrode R/C is grounded, so that at the working electrode W, an oxidation reaction occurs, and the working electrode W electrochemically reacts with chemical reagents and an analyte to output a physiological signal Ia. The AgCl in the counter electrode R/C has a consumption amount corresponding to the physiological signal Ia. As shown in FIGS. 8A-C, between any two of a plurality of measurement periods T1 is a period T2 during which no measurement is performed. In some preferred embodiments, T2 is a constant value.

The replenishment mode can be started and stopped by applying a replenishment potential difference V2, which is a variable value, and removing the replenishment potential difference V2, respectively, and the corresponding current is represented by Ib. In the replenishment mode, the replenishment potential difference V2 is applied across the working electrode W and the counter electrode R/C during the replenishment period t2 (wherein t2 is in a range of 0 to T2). During the replenishment mode, as shown in FIG. 6B, the switches S1 and S4 are in the open circuit state, the switch S2 and at least one of switches corresponding to I_F1 to I_Fn are in the close circuit state (wherein FIG. 6B exemplarily shows that the switches corresponding to I_F1 and I_F3 are in the close circuit state), the working electrode W is grounded, and the counter electrode R/C is +V2, so that on the counter electrode R/C, an oxidation reaction of Ag occurs to replenish the counter electrode R/C with AgCl. In the replenishment mode, according to the magnitude of the physiological signal Ia and the measurement period T1, at least one of the switches corresponding to I_F1 to I_Fn can be selected to be turned on to output a constant current Ib, and the replenishment amount of AgCl can be controlled by adjusting the period t2 during which the potential difference V2 is applied. That is, on the premise that the AgCl on the counter electrode R/C is kept within the safe storage range, the replenishment amount can be equal to or not equal to (including approximately similar, greater than or less than) consumption amount.

Switching Applications of a Continuous Variable Constant Current Circuit.

Figure 7A:
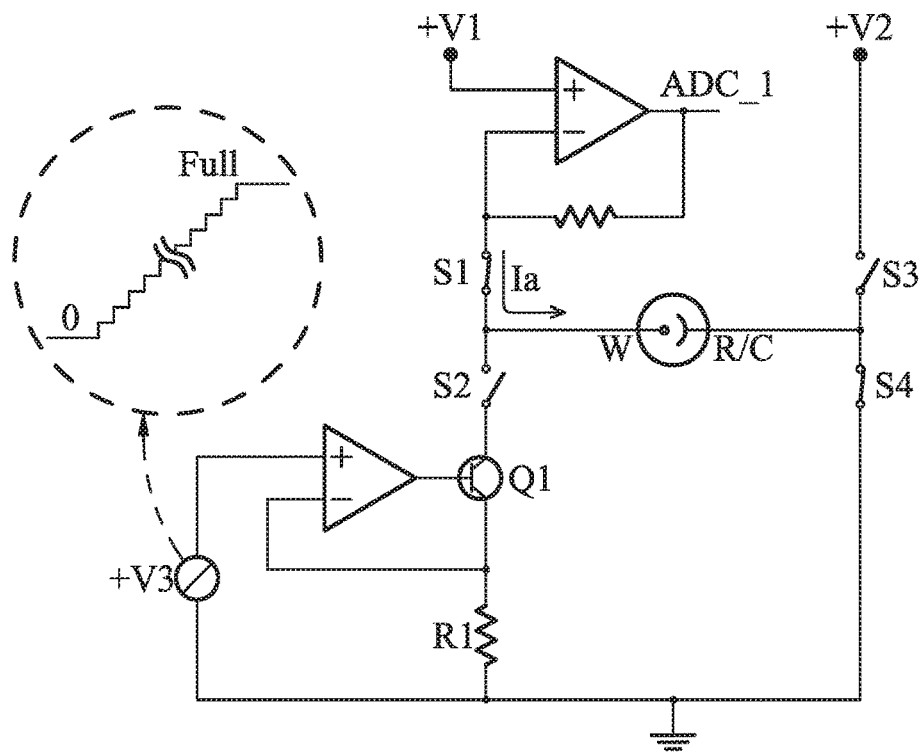
FIG. 7A shows a continuous variable constant current circuit in a measurement mode in the present invention.
Figure 7B:
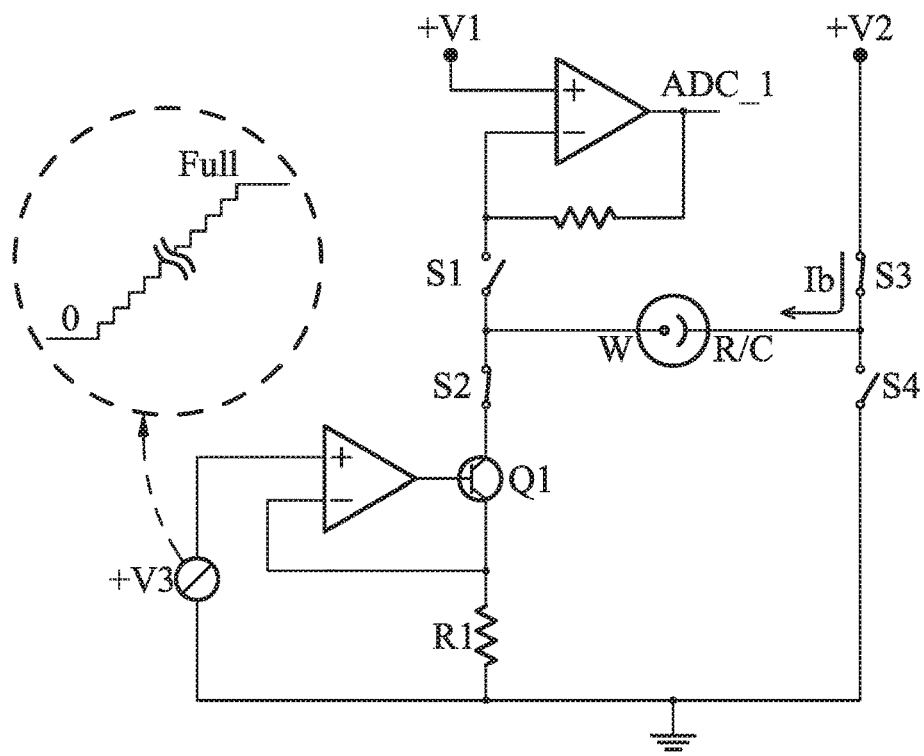
FIG. 7B shows a continuous variable constant current circuit in a replenishment mode in the present invention.

Please refer to FIGS. 7A-7B and FIGS. 8A-8C, wherein FIGS. 7A and 7B show a continuous variable constant current circuit in a measurement mode and a replenishment mode, respectively, according to the present invention. The measurement mode and the replenishment mode in this embodiment are similar to those in FIGS. 6A and 6B, so they will not be repeated here. This embodiment differs from that in FIGS. 6A and 6B only in that in the replenishment mode, according to the magnitude of the physiological signal Ia, a constant current Ib can be output by the control of the digital-to-analog converter (DAC), and the replenishment amount of AgCl can be controlled by adjusting the period t2 during which the potential difference V2 is applied. That is, on the premise that the AgCl on the counter electrode R/C is kept within the safe storage range, the replenishment amount can be equal to or not equal to (including approximately similar, greater than or less than) consumption amount.

In FIGS. 8A-8C, the horizontal axis represents time, the vertical axis represents current, the curve for V1 represents the application and removal of the measurement potential difference V1, and the curve for V2 represents the application and removal of the replenishment potential difference V2. Please refer to FIG. 8A, in a preferred embodiment, T2 is a constant value, V2 and the period t2 (i.e., the replenishment period) during which V2 is applied are variable values. The replenishment period t2 is dynamically adjusted in a range of 0 to T2 according to the measurement period T1 and the physiological signal Ia measured in the measurement mode. As shown in FIG. 8A, t2 can be t2/2 is applied are variable values. The repe replenishment period t2 can be changed according to the consumption amount of AgCl. In the condition of a high consumption amount of AgCl, the counter electrode R/C can be replenished for a longer time to keep the AgCl on the counter electrode R/C within the safe storage range.

Please refer to FIG. 8B, in another preferred embodiment, V2 is a variable value, and T2 and t2 are constant values, wherein t2 is a constant value greater than 0 and less than T2. For example, t2 can be ½ T2, ⅖ T2, ⅗ T2, etc. In this embodiment, V2 is dynamically adjusted according to the consumption amount of AgCl in the step of measuring the physiological signal (i.e., in the measurement mode). One example of the dynamic adjustment method is as follows. For example, the segmental constant current circuit is used. The circuit includes n constant current supplies and n switches, and each constant current supply corresponds to a switch. In the replenishment mode, according to the consumption amount of AgCl, at least one of the n switches is selected to be turned on (i.e., in the close circuit state) to output a constant current value. When the replenishment period t2 is a constant value, the replenishment amount of AgCl can be controlled by selecting different constant current outputs.

Please refer to FIG. 8C, in another preferred embodiment, V2 is a variable value, T2 and t2 are constant values, wherein t2=T2. That is, the measurement mode and replenishment mode alternate seamlessly, and the period during which no measurement is performed is the replenishment period.

Compared with the continuous variable constant current circuit, in the segmental constant current circuit, multiple current paths can be controlled through multiple switches, and thus the replenishment can be performed by multi-segment constant current according to the amount of current required. The multi-segment constant current, in this way, saves electricity and can reduce costs. In addition, whether it is a constant voltage circuit or a constant current circuit, the potential difference can come from a DC power supply or an AC power supply, preferably from a DC power supply.

The embodiments of FIGS. 5A to 8C all involve the operation manner of alternately cycling measurement step and replenishment step, which means that there is an AgCl replenishment step between any two measurement steps. Such manner can better ensure that AgCl remains within the safe storage range. However, in some preferred embodiments, Y times of AgCl replenishment can be optionally performed during N measurements, where Y N, in such a way that the accumulated replenishment amount of AgCl can still be kept within the safe storage range. The measurement step and the replenishment step do not necessarily need to be performed in an alternate cycle. A replenishment step can also be performed after several measurement steps, or after a predetermined measurement time. For example, a replenishment step can be performed after 10 measurement steps, or after the accumulated measurement time reaches 1 hour.

Figure 8D:
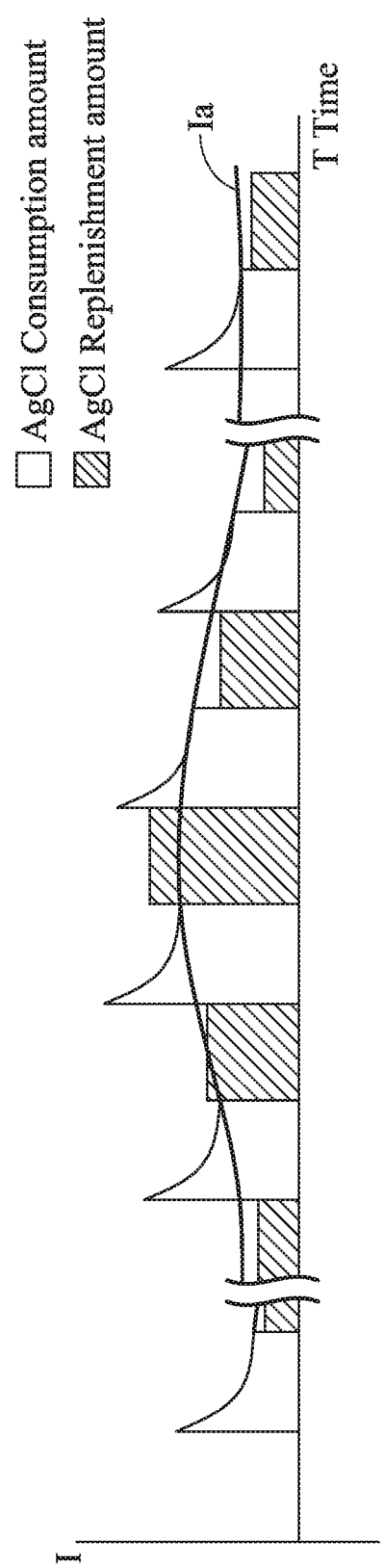
FIG. 8D shows a schematic diagram of the constant current circuit running in the measurement mode and the replenishment mode by turns in a third way.

Please refer to FIG. 8D, which shows a current-time schematic diagram of the constant current circuit running in the measurement mode and the replenishment mode by turns in a way similar to that of FIG. 8C. In FIG. 8D, the curve represents the physiological parameter curve calculated from the measured physiological signal Ia, the conditions of T2 and t2 being both constant values and V2 being a variable value are similar to those in FIG. 8C. In FIG. 8D, the white area under the curve represents the AgCl consumption amount in the measurement mode (Ia*Tl), and the oblique area represents the replenishment amount of AgCl in the replenishment mode (Ib*t2). It can be seen from this figure that in order to make Ib*t2 close to Ia*Tl or within a certain range of Ia*Tl, the replenishment potential difference V2 is dynamically adjusted according to the consumption amount of AgCl.

In addition, although FIGS. 5E, 5F, and 8D do not show the output timing of each physiological parameter value after each measurement step for measuring a physiological signal is performed, the physiological parameter value may be output, but is not limited to, when the measurement is completed or during the replenishment period and the AgCl replenishment step may be performed after every physiological parameter is output or after obtaining the physiological signal, but is not limited thereto.

Please refer to FIG. 9, which shows a method of measuring an analyte according to the present invention. A usage lifetime of a micro biosensor can be prolonged by the method. The micro biosensor, which may be, for example, the micro biosensor shown in FIG. 2A to FIG. 3, is used to be implanted subcutaneously to measure a physiological signal representative of a physiological parameter associated with the analyte in a biofluid (such as tissue fluid). In the embodiment of FIG. 9, the analyte can be glucose in the tissue fluid, the physiological parameter is the glucose level in the human body, and the physiological signal is a current value measured by the micro-biological sensor. In this embodiment, the method for measuring the analyte includes repeatedly performing the measurement step (S901) and the replenishment step (S902). The measurement step (S901) includes using the aforementioned constant voltage circuit or the constant current circuit to perform the aforementioned measurement mode during the measurement period T1 to output a physiological signal (i.e., a current value), and at the same time, the AgCl on the counter electrode has a consumption amount corresponding to the current value. The measurement step (S901) also includes stopping the measurement step by stopping the measurement mode, and the current value is calculated to output a physiological parameter (i.e., glucose level).

In the measurement step (S901), the chemical equations are as follows.

The following oxidation reactions occur at the working electrode 120.

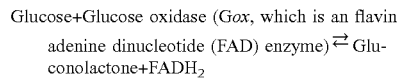

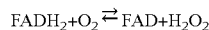

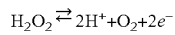

The following reduction reactions occur at the counter electrode 130.

$$2AgCl+2e^- \rightleftarrows 2Ag+2Cl^-$$

The replenishment step (S902) includes using the aforementioned constant voltage circuit or constant current circuit to perform the aforementioned replenishment mode during the replenishment period, such that the AgCl on the counter electrode has a replenishment amount corresponding to consumption amount, and thus the AgCl on the counter electrode has an amount controlled within a safe storage range. As a result, the potential difference between the working electrode and the counter electrode can be kept stable, so that the obtained current value can still maintain a stable correlation with the glucose value (if the detected substance is other analytes, the correlation may be proportional or inverse correlation). In other words, it is possible to keep a stable correlation between a next current value obtained in a next measurement step and a next glucose value. The replenishment step (S902) also includes a step of stopping the replenishment step by stopping the aforementioned replenishment mode. After the replenishment step (S902) is finished, the method returns to the measurement step (S901) until N measurement steps (S901) and N replenishment steps (S902) are executed.

In the replenishment step (S902), the chemical equations are as follows. The following reduction reactions occur at the working electrode 120.

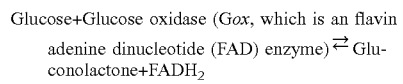

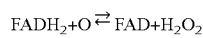

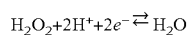

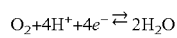

The positive potential on the counter electrode 130 cause the following oxidation reactions occurring at the counter electrode 130.

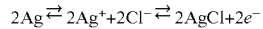

The Ag on the counter electrode is oxidized to Ag$^+$ and combined with Cl$^-$ from the body or from oxidation (or dissociation) of AgCl to form AgCl, such that part or all of the AgCl consumed during the measurement period T1 is replenished onto the counter electrode.

Human can intake chloride ions and iodide ions through iodine-doped salts. The available halide ions include at least chloride ions and iodide ions for replenishing the counter electrode with silver halide.

The following embodiments are directed to cycles of N measurement steps (S901) and N replenishment steps (S902). The physiological parameter mentioned is preferably a glucose value, and the physiological signal mentioned is preferably a current value. According to some preferred embodiments, each measurement potential difference V1 is applied during the measurement period T1, each replenishment potential difference V2 is applied during the replenishment period t2, and the measurement period T1 is a constant value, which can be a value within 3 seconds, 5 seconds, 10 seconds, 15 seconds, 30 seconds, 1 minute, 2.5 minutes, 5 minutes, 10 minutes, or 10 minutes. According to some preferred embodiments, the constant value may be a value within 30 seconds. The measurement period T1 is a constant value, and can be 2.5 seconds, 5 seconds, 15 seconds, 30 seconds, 1 minute, 2.5 minutes, 5 minutes, 10 minutes, or 30 minutes, preferably 30 seconds. According to some preferred embodiments, each measurement period T1 plus each replenishment period t2 is a constant value. According to some preferred embodiments, each replenishment potential difference V2 has a constant voltage value, and each replenishment period t2 is dynamically adjusted according to each consumption amount of AgCl (as shown in FIG. 5A). According to some preferred embodiments, each output physiological parameter is obtained through calculation of the physiological signals at a single measurement time point in each measurement period T1. According to some preferred embodiments, each output physiological parameter is obtained through a mathematical operation value of a plurality of physiological signals at a plurality of measurement time points in each measurement period T1. The aforementioned mathematical operation value is, for example, a accumulated value, an average value, a median value, an average value of median, and so on. According to some preferred embodiments, the replenishment amount of AgCl on the counter electrode is controlled within a safe storage range by controlling each replenishment amount to be equal to or not equal to (including approximately similar, greater than or less than) each consumption amount. As a result, a next physiological signal obtained during a next measurement step maintains a stable proportional correlation with a next physiological parameter. According to some preferred embodiments, the step of removing each measurement potential difference V1 is to disconnect the circuit that connects the working electrode and the counter electrode, or set each measurement potential difference V1 to zero. In other words, the power can be turned off to make the measurement circuit have an open circuit state; or, a 0 volt voltage can be applied across the working electrode and the counter electrode, wherein the operation time of either of the two operations is 0.01~0.5 seconds. The step of removing the measurement potential difference V1 can avoid the generation of A-shaped physiological signals. According to some preferred embodiments, the step of removing each replenishment potential difference V2 is to disconnect the circuit configured to connect the working electrode and the counter electrode, or set each replenishment potential difference V2 to zero.

According to some preferred embodiments, after the biosensor is implanted in the human body, a warm-up time is required for the biosensor to be in the condition of equilibrium and stability in the body in order to stably present a physiological signal that is positively correlated with an analyte concentration. Therefore, in the measurement step (S901), the measurement voltage is continuously applied until the end of the measurement period T1, and the measurement period T1 is controlled such that the physiological signal and the physiological parameter of the analyte have a stable proportional correlation. To this end, the measurement period T1 can be a variable value or a combination of a variable value and a constant value (for example, a variable value plus a constant value, in which the variable value may be 1 hour, 2 hours, 3 hours, 6 hours, 12 hours or 24 hours, and the constant value may be, for example, 30 seconds).

Please refer to FIGS. 5A-F, 8A-8D and 9. The present invention uses a voltage applied to the counter electrode R/C during a period to measure a resultant current of the counter electrode, and the initial capacity of AgCl is obtained by mathematical calculation of the resultant current during the period. For example, the initial capacity of AgCl is defined by calculating area under a curve of the resultant current. The initial capacity of AgCl is also referred to as the initial amount or initial coulomb amount ($C_{initial}$), the following are all described by amount. The counter electrode R/C contains Ag and AgCl. When the amount of AgCl (X % AgCl) is known, the amount of Ag can be calculated (Y % Ag=100%−X % AgCl). In each measurement step (S901), the consumption amount of AgCl (denoted by $C_{consume}$) is defined by calculating the area under the current curve of the working electrode W. The AgCl of the counter electrode R/C has a consumption amount $C_{consume}$ corresponding to the physiological signal Ia, i.e., $C_{consume}$=Ia*T1. In each replenishment step (S902), each replenishment amount (denoted by $C_{replenish}$) of AgCl is defined by calculating the area under the current curve of the counter electrode R/C, i.e., $C_{replenish}$=Ib*t2, where t2 is a value in a range of 0~T2.

The calculation method of AgCl safe storage amount is described below. In some preferred embodiments, the safe storage range is represented by the ratio of Ag to AgCl. The present invention uses the coulomb amount (C) measured at the counter electrode to reflect the ratio of Ag to AgCl. In some preferred embodiments, the ratio of Ag to AgCl is 99.9%:0.1%, 99%:1%, 95%:5%, 90%:10%, 70%:30%, 50%:50%, 40%:60% or 30:70%, which assure of a certain amount of the AgCl on the counter electrode without being exhausted, and thus each measurement step for measuring the physiological signal can be performed stably. The remaining amount of AgCl is the sum of the replenishment amount and the initial amount minus the consumption amount. In some preferred embodiments, the remaining amount of AgCl varies within a range, that is, the remaining amount of AgCl is controlled within a range of the initial amount plus or minus a specific value (X value). Namely, ($C_{replenish}$+$C_{initial}$)−$C_{consume}$=$C_{initial}$±X, where 0<X<100% $C_{initial}$, 10% $C_{initial}$<X≤90% $C_{initial}$, or 0.5% $C_{initial}$<X≤50% $C_{initial}$. In some preferred embodiments, the remaining amount of AgCl may, within a range, gradually decrease, gradually increase, change steadily, or change arbitrarily but still within the range.

Figure 10:
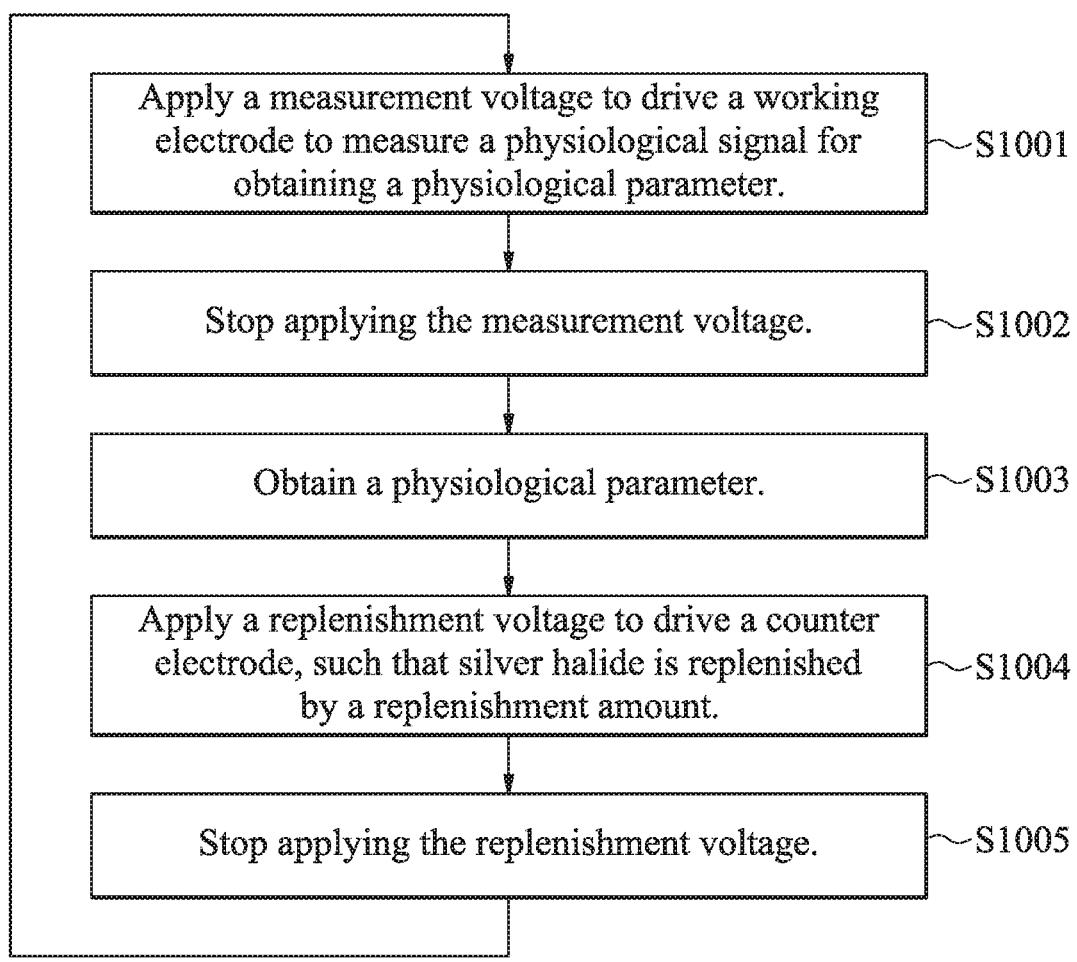
FIG. 10 shows a method of measuring an analyte according to another embodiment in the present invention.

Please refer to FIG. 10, which shows a method for measuring an analyte according to another embodiment of the present invention. Through this method, the usage lifetime of the micro biosensor can be prolonged and the amount of silver and silver halide materials of the counter electrode can be reduced. The micro biosensor, which may be, for example, the micro biosensor shown in FIG. 2A-2C and FIG. 3, is used to be implanted subcutaneously to measure a physiological signal representative of a physiological parameter associated with the analyte in a biofluid (such as tissue fluid). The electrode material of the counter electrode of the micro biosensor includes silver and silver halide. In the embodiment of FIG. 10, the analyte can be glucose in tissue fluid, the physiological parameter is the glucose value in the human body, and the physiological signal is a current value measured by the micro biosensor. Only one cycle of this embodiment is described below. The method of this embodiment starts with the step of applying a measurement voltage to drive a working electrode to measure a physiological signal for obtaining a physiological parameter, wherein a specific amount of silver halide is consumed (hereinafter referred to as "consumption amount") (S1001).

Then the step of applying the measurement voltage is stopped (S1002), and the obtained physiological signal is used to obtain a physiological parameter (S1003). After the physiological parameter is obtained, a replenishment voltage is applied across a counter electrode and a working electrode to drive a counter electrode, such that silver halide is replenished by a replenishment amount (S1004), wherein a value (i.e., the aforementioned 1 parameter (S1003). fluisum of the replenishment amount and an initial amount minus the consumption amount is controlled within a range of the initial amount plus or minus a specific value. The above control step is achieved by controlling the replenishment amount to be equal to or not equal to (including approximately similar, greater than or less than) the consumption amount so as to maintain the amount of silver halide within a safe storage range. According to the chemical equations, the increase or decrease of the mole number of silver halide corresponds to the increase or decrease of the mole number of silver. Therefore, for the ease of descriptions, the consumption amount of silver halide corresponds to a simulated increased amount of silver. In some preferred embodiments, a value of the remaining amount is controlled such that the ratio of the amount of silver halide to the sum of the amount of silver halide plus the amount of silver ($AgCl/Ag+AgCl$) is greater than 0 and less than 1 (which means that there should be a certain amount of silver halide in the counter electrode), preferably between 0.01-0.99, between 0.1-0.9, between 0.2-0.8, between 0.3-0.7, or between 0.4-0.6. When the replenishment amount is reached, the step of applying the replenishment voltage is stopped (S1005). Then the method returns to step S1001 to execute the next loop.

A specific embodiment of the present invention will be described below. Taking a usage lifetime of a biosensor must reach 16 days as an example. To this end, the method to calculate the required size of Ag/AgCl material on a signal sensing section of a electrode is described below. For example, the average of the measured current of the analyte for each measurement is 30 nA, the measurement period (T1) is 30 seconds, and the replenishment period (t2) is 30 seconds. The daily consumption amount of AgCl ($C_{consume/day}$)=1.3 mC/day. Assuming that the requirement of a usage lifetime of a biosensor is 16 days, the consumption amount of AgCl required for using 16 days is 1.3× 16=20.8 mC.

For example, the length of the counter electrode is 2.5 mm, which corresponds to the initial amount of AgCl $C_{initial}$=10 mC.

(1) On a condition that AgCl replenishment is not performed, for the sensor usage lifetime of 16 days, the required length of the counter electrode is at least:

$$C_{16day}/C_{consume/day}=20.8 \text{ mC}/1.3 \text{ mg/day}=16 \text{ mm}.$$

(2) Therefore, on a condition that the replenishment method for the silver halide in the present application is not performed, the length of the counter electrode needs to exceed 16 mm in order to make the usage lifetime of the sensor achieve 16 days.

In this embodiment, on a condition that the replenishing technique for silver halide in the present invention is not used, the signal sensing section of the counter electrode needs to be configured with a relatively large size of Ag/AgCl material to achieve the usage lifetime of 16 days. Through the replenishment method for silver halide in the present invention, the replenishment step for silver halide is performed between two measurement steps. The consumption and replenishment of the silver halide cycles repeated in a short period of time (replenished when used), so the amount of Ag/AgCl material in the sensor can be reduced, and thereby the sensor is miniaturized. Therefore, there is no need to prepare 16 days of AgCl capacity for the signal sensing section material of the electrode for consumption. For example, the preparation of the capacity of AgCl for about 1-2 days can achieve a usage time of 16 days of the sensor. Thus, the present invention has the effect of prolonging the usage lifetime of the sensor. The capacity of AgCl for 1-2 days also refers to the initial amount of AgCl in the counter electrode before leaving the factory or before performing the first measurement. The initial amount of AgCl may be, for example, between about 1.3 and 2.6 mC, and can be in other smaller range or a larger range. In other embodiments, different AgCl capacities for 1-5 days, 1-3 days, 6-24 hours, and 6-12 hours can also be prepared. The size of the signal sensing section of the counter electrode can be configured in such a way that the counter electrode has a capacity which enables stable executions of each measurement step for glucose and the positive correlation between the measurement current and the glucose concentration in the body.

The prior art increased the electrode length/area to make the sensor reach the required measurement days without using the silver chloride replenishment technology of the present invention. For example, the length of the implantation end of the prior art is about 12 mm. Due to the long implantation length of the prior art, the implantation end needs to be implanted subcutaneous at an oblique angle to avoid the implantation end from implanting deeply into the subcutaneous tissue, which causes a large implantation wound. For another example, the capacity of AgCl for 1-2 days is about 1.3~2.6 mC, the length of the counter electrode for 1~2 days is 2.5~5 mm after conversion, and thus the length of the counter electrode needs 16 mm without using the replenishment method for silver halide in the present invention. Comparing to the example above, it is obvious that the present invention has more significant effect on shortening the size of the counter electrode. According to the silver chloride replenishment step of the present invention, the implantation end of the present invention can be shortened, for example, to no greater than 10 mm. Please refer to FIGS. 2A-2C, the lower half of the connecting area 117 to the second end 114 of the micro biosensor 100 of the present invention forms a short implantation end 118, as shown in FIGS. 2A and 2B. The implantation depth of the short implantation end 118 is at least a depth to the dermis where can measure the glucose concentration in the tissue fluid. According to the silver chloride replenishment step of the present invention, a length of the longest side of the short implantation end 118 is no greater than 6 mm, so that the short implantation end 118 of the micro biosensor 100 can be perpendicularly implanted under the biological epidermis. Preferably, the length of the longest side of the short implantation end 118 is no greater than 5 mm, 4.5 mm, 3.5 mm or 2.5 mm. The short implantation end 118 of the present invention includes the signal sensing section 132 of the counter electrode 130, and a length of the longest side of the signal sensing section 132 of the counter electrode 130 is no greater than 6 mm, preferably 2-6 mm, 2-5 mm, 2-4.5 mm, 2-3.5 mm, 0.5-2 mm or 0.2-1 mm.

Therefore, compared with the cases where the silver halide replenishment technique of the present invention is not used, the silver halide replenishment method of the present invention can effectively extend the micro sensor's usage lifetime, and can also greatly reduce the use of Ag/AgCl material on the counter electrode, which causes the size of the signal sensing section of the counter electrode to be reduced. Because of the reduced use of the Ag/AgCl material on the counter electrode, the sensor can be miniaturized and biological toxicity can be reduced. In addition, the reduced size of the electrode specifically refers to the shortened length of the implantation end of the sensor, which would reduce pain for the user during implantation.

Embodiment II

Figure 11:
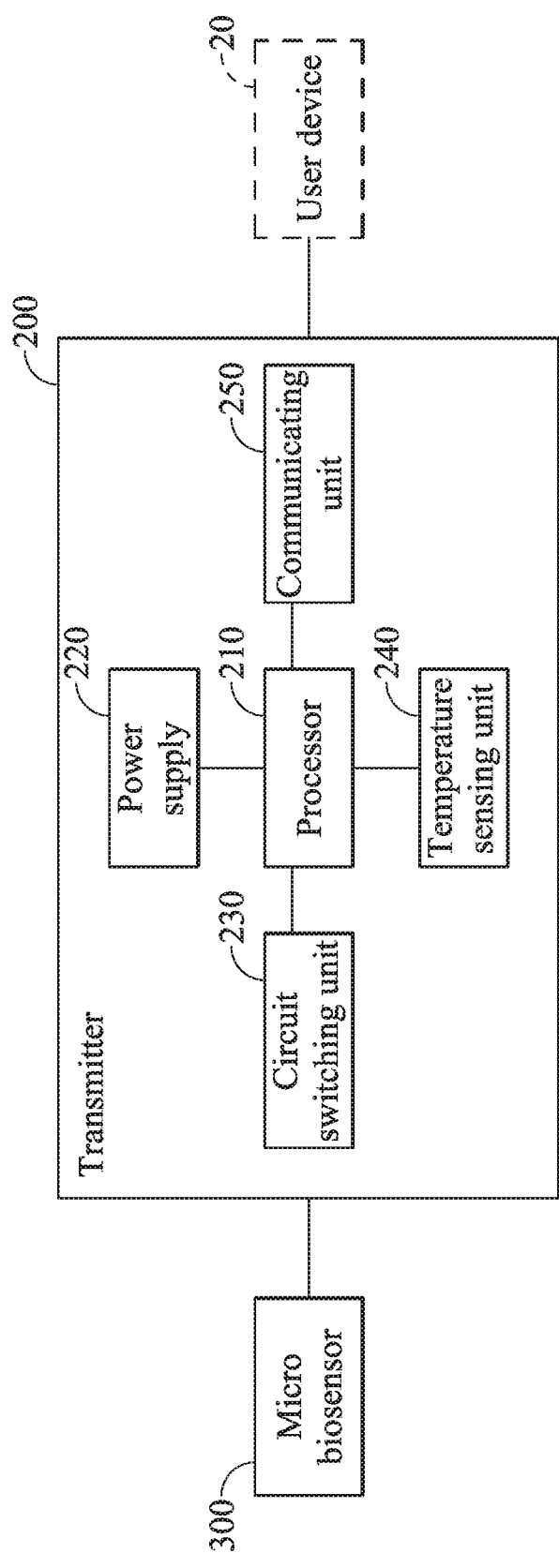
FIG. 11 shows a schematic diagram of a physiological signal measurement device of the present invention.

Please refer to FIG. 11, which is a schematic diagram of a physiological signal measurement device of the present invention. The physiological signal measurement device 10 of the present invention can be implanted subcutaneously to measure a physiological signal representing a physiological parameter associated with an analyte in a biofluid. The physiological signal measurement device 10 of the present invention includes a micro biosensor 300 and a transmitter 200, wherein the transmitter 200 is electrically connected to the micro biosensor 300, includes a processor 210 and a power supply 220, a circuit switching unit 230, a temperature sensing unit 240 and a communicating unit 250. The power supply 220 provides a voltage to the micro biosensor 300 through the circuit switching unit 230 for measuring the physiological signal, the temperature sensing unit 240 measures the body temperature of the living body, thereby the temperature measuring signal and the measured physiological signal measured by the micro biosensor 100 are transmitted to the processor 210, and the processor 210 operates the measured physiological signal to a physiological parameter. The communicating unit 250 can communicate with a user device 20 by a wire or wireless transmission.

Figure 12A:
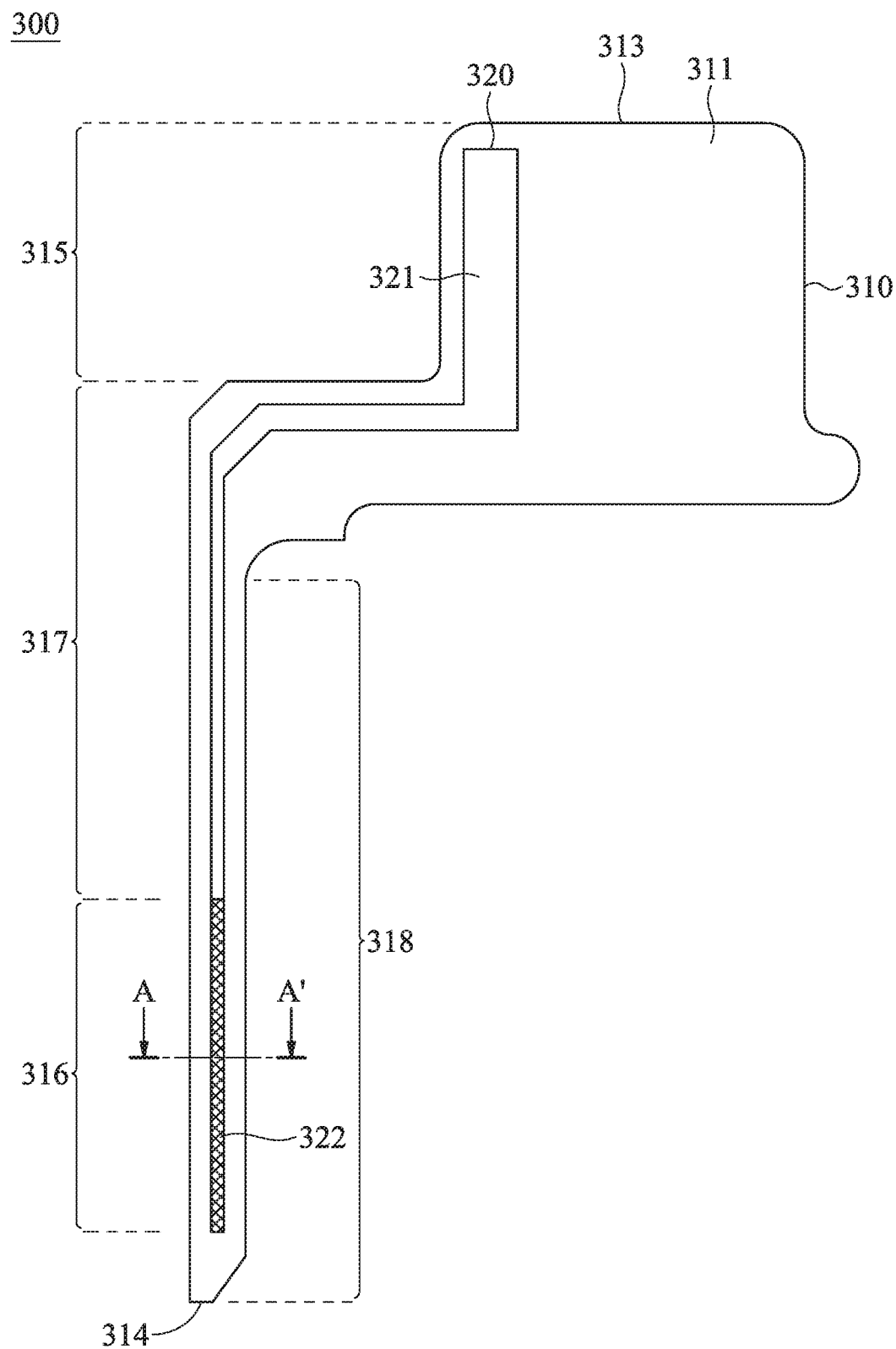
FIG. 12A shows a front schematic diagram of a first embodiment of a micro biosensor of the present invention.
Figure 12B:
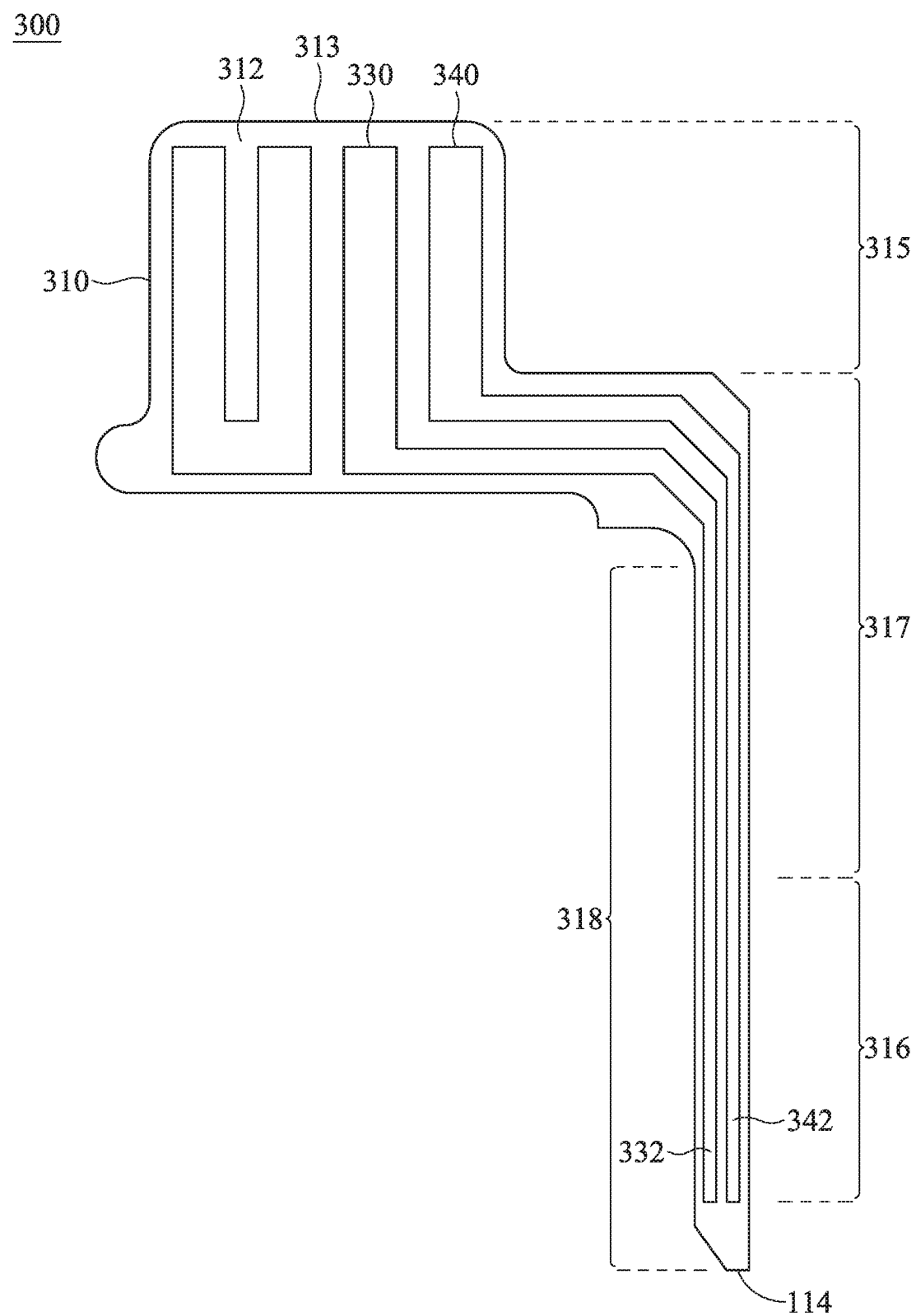
FIG. 12B shows a back schematic diagram of the first embodiment the micro biosensor of the present invention.
Figure 12C:
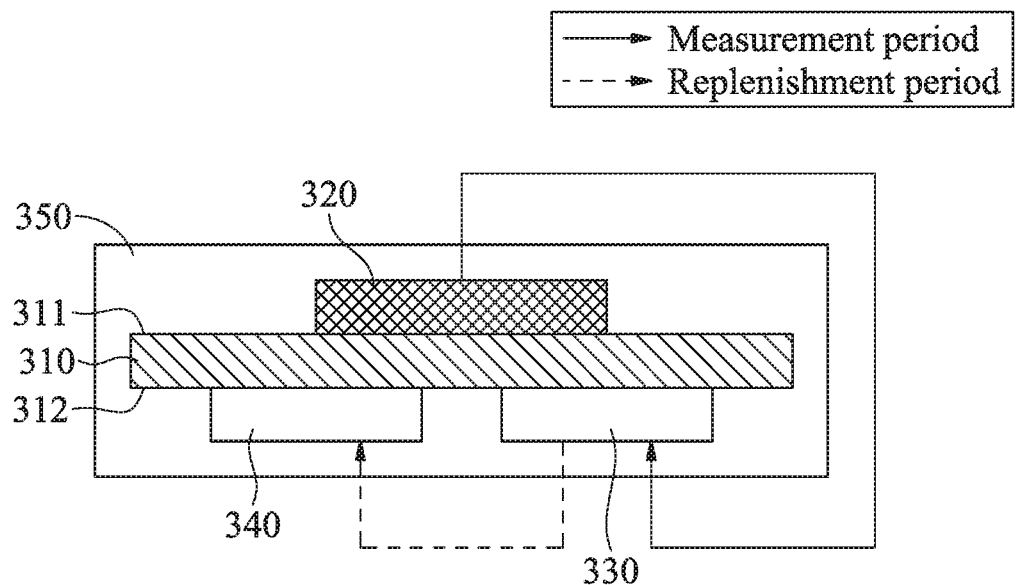
FIG. 12C shows a sectional schematic diagram of a cut view of the micro biosensor along the section line A-A' in FIG. 2A.

Please refer to FIGS. 12A and 12B, which are front and back schematic diagrams of a first embodiment of the micro biosensor of the present invention. The micro biosensor 300 of the present invention includes a substrate 310, a working electrode 320, a counter electrode 330 and an auxiliary electrode 340 disposed on the substrate 310, and a chemical reagent 350 (as shown in FIG. 12C) covering the working electrode 320, the counter electrode 330 and the auxiliary electrode 340. The material of the substrate 310 can be any material that is known to be suitable for use in electrode substrates and preferably has flexibility and insulation properties, such as but not limited to: polymer materials such as polyester and polyimide. The aforementioned polymer materials can be used alone or in combination. The substrate 310 includes a surface 311 (i.e. a first surface), an opposite surface 312 (i.e. a second surface) opposite to the surface 311, a first end 313 and a second end 314. The substrate 310 is separated into three areas respectively—they are a signal output area 315 located close to the first end 313, a sensing area 316 located close to the second end 314, and a connecting area 317 located between the signal output area 315 and the sensing area 316. The working electrode 320 is disposed on the surface 311 of the substrate 310 and extended from the first end 313 to the second end 314 of the substrate 310. The working electrode 320 includes a signal output section 321 located in the signal output area 315 of the substrate 310, and a signal sensing section 322 located in the sensing area 316 of the substrate 310.

The counter electrode 330 and the auxiliary electrode 340 are disposed on the opposite surface 312 of the substrate 310 and extended from the first end 313 to the second end 314 of the substrate 310. The counter electrode 330 includes a signal sensing section 332 located in the sensing area 316 of the substrate 310, and the auxiliary electrode 340 includes a signal sensing section 342 located in the sensing area 316 of the substrate 310. The sensing area 316 of the micro biosensor 300 can be implanted subcutaneously to cause the signal sensing section 322 to measure the physiological signal of the analyte in the biofluid. The physiological signal is transmitted to the processor 210 through the signal output section 321 to obtain the physiological parameter. In addition, apart from the transmitter 200, the physiological parameter can also be obtained from the user device 20 through the wire/wireless communication. The common user device 20 can be a smartphone, a physiological signal receiver or a blood glucose meter.

The material of the surface of the counter electrode 330 includes silver and silver halide, preferably silver chloride or silver iodine. Because the electrode material of the counter electrode 330 of the present invention includes silver and silver halide (Ag/AgX), the counter electrode 330 of the present invention includes functions of the counter electrode and the reference electrode of the common knowledge in the art. Specifically, the counter electrode 330 of the present invention can (1) form an electronic circuit with the working electrode 320 to cause the current between the counter electrode 330 and the working electrode 320 to be conducted to ensure that the oxidation reaction occurs on the working electrode 320; and (2) provide a stable relative potential as a reference potential. Therefore, the working electrode 320 and the counter electrode 330 of the present invention form a 2-electrode system. In order to further reduce the cost and improve the biocompatibility of the biosensor of the present invention, the Ag/AgX can be used with carbon, for example, the Ag/AgX is mixed into carbon paste, and the content of the silver halide can be an amount that allows the counter electrode 330 to stably perform the measurement step. The surface of the counter electrode 330 can be partially covered by a conductive material to prevent silver halide from the dissolution and to protect the counter electrode 330, wherein the conductive material is selected from the material that does not affect the measuring result of the working electrode. For example, the conductive material is carbon.

In another embodiment, the biosensor is not limited to a wire-type or stacked-type electrode structure.

According to another embodiment of the present disclosure, the initial amount of the silver halide can be zero before the biosensor is ready for shipping out of the plant for sale. In this case the counter electrode 330 of the biosensor has no silver halide. After the biosensor is subcutaneously implanted in the patient and during the first replenishment period before the first measurement, the initial amount of the silver halide can be replenished by oxidizing the silver coated on the electrodes 330.

The auxiliary electrode 340 forms an electronic circuit with the counter electrode 330 in the replenishment step to cause the current between the counter electrode 330 and the auxiliary electrode 340 to be conducted to ensure that the oxidation reaction occurs on the counter electrode 330. The electrode material of the auxiliary electrode 340 can be the same as that of the working electrode 320 or be a lower sensitivity to hydrogen peroxide, such as carbon, than that of the working electrode 320.

The chemical reagent 350 covers at least partial surfaces of the signal sensing sections 322, 332, 342 of each of the electrodes. In another embodiment, the chemical reagent 350 covers at least partial surfaces of the signal sensing section 322 of the working electrode 320 (figure not shown). Specifically, the counter electrode 330 is not covered by the chemical reagent 350. The sensing area 316 of the micro biosensor 300 can be implanted subcutaneously to cause the signal sensing section 322 of the working electrode 320 to measure the physiological signal of the analyte in the biofluid. The physiological signal is transmitted to the processor 210 through the signal output section 321 of the working electrode 320 to obtain the physiological parameter. In addition, apart from the transmitter 200, the physiological parameter can also be obtained from the user device 20 through the wire/wireless communication.

Please refer to FIG. 12C, which is a sectional schematic diagram of a cut view of the micro biosensor along the section line A-A' in FIG. 21A, wherein the line A-A' is a section line of the sensing area 316 of the micro biosensor 300. In FIG. 12C, the working electrode 320 is disposed on the surface 311 of the substrate 310, the counter electrode 330 and the auxiliary electrode 340 are disposed on the opposite surface 312 of the substrate 310, and the surfaces of the working electrode 320, the counter electrode 330 and the auxiliary electrode 340 are covered by the chemical reagent 350. Basically, the chemical reagent 350 at least covers partial surface of the working electrode 320. The micro biosensor 300 of the present invention performs a measurement step during a measurement period, and performs a replenishment step during a replenishment period. When the measurement step is performed, a voltage level of the working electrode 320 is higher than that of the counter electrode 330, causing a current to flow from the working electrode 320 to the counter electrode 330, so that an oxidation reaction occurs on the working electrode 320 having an electrochemical reaction with the chemical reagent 350 and the analyte and the physiological signal is measured, and a reduction reaction occurs on the counter electrode 330, so that silver halide (AgX) in the counter electrode 330 is consumed and dissociated into silver (Ag) and halide ion ($X^-$). Because the silver halide in the counter electrode 330 is consumed, the silver halide needs to be replenished in the counter electrode 330 to perform the next measurement step. When the replenishment step is performed, the voltage level of the counter electrode 330 is higher than that of the auxiliary electrode 340, causing a current to flow from the counter electrode 330 to the auxiliary electrode 340, so that an oxidation reaction occurs on the counter electrode 330 to cause silver to combine with halide ion in the living body to replenish silver halide. The detailed measurement step and the detailed replenishment step are illustrated in FIG. 9.

Figure 13A:
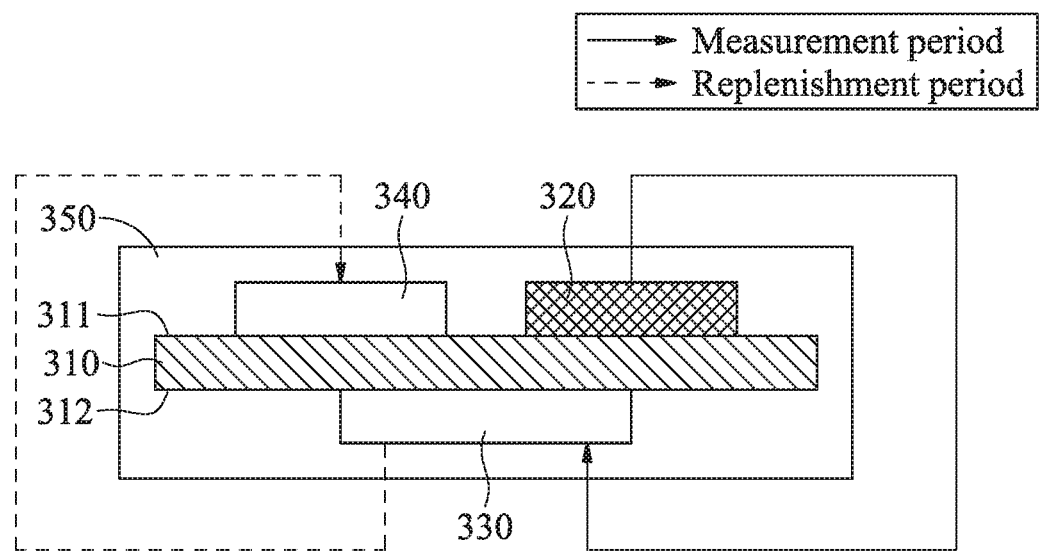
FIG. 13A shows a sectional schematic diagram of a second embodiment of the micro biosensor of the present invention.

Please refer to FIG. 13A, which is a sectional schematic diagram of a second embodiment of the micro biosensor of the present invention. In FIG. 13A, the working electrode 320 and the auxiliary electrode 340 can be disposed on the surface 311 of the substrate 310, the counter electrode 330 is disposed on the opposite surface 312 of the substrate 310, and the surfaces of the working electrode 320, the counter electrode 330 and the auxiliary electrode 340 are covered by the chemical reagent 350. In this embodiment, when the measurement step is performed, a current flows from the working electrode 320 to the counter electrode 330, so that an oxidation reaction occurs on the working electrode 320 and the physiological signal is measured, and silver halide (AgX) in the counter electrode 330 is consumed and dissociated into silver (Ag) and halide ion ($X^-$). When the replenishment step is performed, a current flows from the counter electrode 330 to the auxiliary electrode 340, so that an oxidation reaction occurs on the counter electrode 330 to cause the combination of silver and halide ion to replenish silver halide.

Figure 13B:
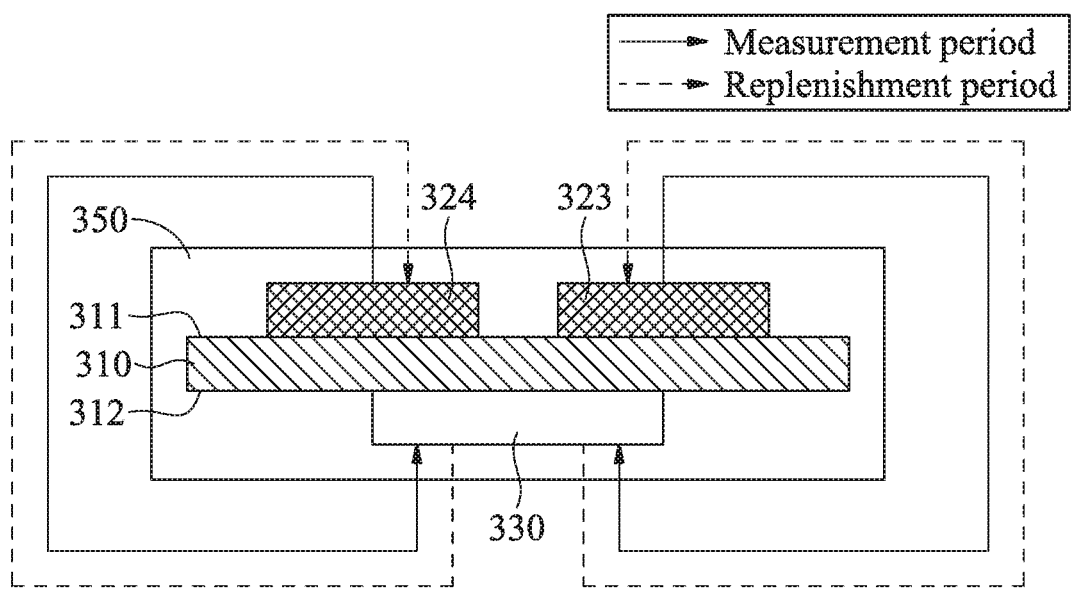
FIG. 13B shows a sectional schematic diagram of a third embodiment of the micro biosensor of the present invention.

Please refer to FIG. 13B, which is a sectional schematic diagram of a third embodiment of the micro biosensor of the present invention. In this embodiment, the micro biosensor 300 has two working electrodes which respectively are a first working electrode 323 and a second working electrode 324, wherein the auxiliary electrode is replaced by the second working electrode 324. In FIG. 13B, the first working electrode 323 and the second working electrode 324 are disposed on the surface 311 of the substrate 310, the counter electrode 330 is disposed on the opposite surface 312 of the substrate 310, and the surfaces of the first working electrode 323, the second working electrode 324 and the counter electrode 330 are covered by the chemical reagent 350. One of the first working electrode 323 and the second working electrode 324 can be selected to measure the physiological signal in the measurement step, and the first working electrode 323 or the second working electrode 324 forms the electronic circuit with the counter electrode 330 to replenish silver halide to the counter electrode 330 in the replenishment step. Therefore, in this embodiment, when the measurement step is performed, a current flows from the first working electrode 323 or the second working electrode 324 to the counter electrode 330, so that an oxidation reaction occurs on the first working electrode 323 or the second working electrode 324 and the physiological signal is measured, and silver halide (AgX) in the counter electrode 330 is consumed and dissociated into silver (Ag) and halide ion ($X^-$). When the replenishment step is performed, a current flows from the counter electrode 330 to the first working electrode 323 or the second working electrode 324, so that an oxidation reaction occurs on the counter electrode 330 to cause the combination of silver and halide ion to replenish silver halide.

Figure 13C:
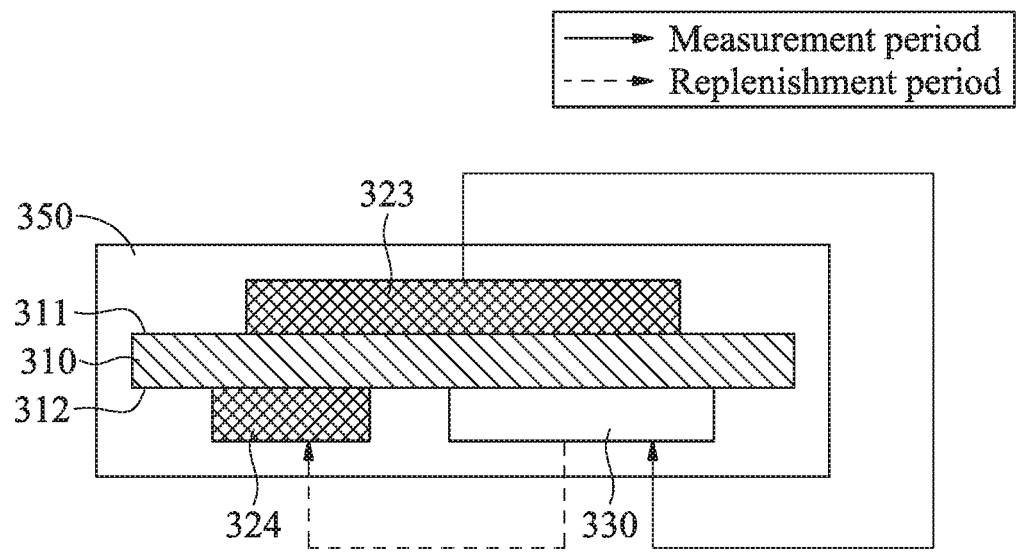
FIG. 13C shows a sectional schematic diagram of a fourth embodiment of the micro biosensor of the present invention.

Please refer to FIG. 13C, which is a sectional schematic diagram of a fourth embodiment of the micro biosensor of the present invention. In this embodiment, the micro biosensor 300 has two working electrodes which respectively are a first working electrode 323 and a second working electrode 324, wherein the auxiliary electrode is replaced by the second working electrode 324. In FIG. 13C, the first working electrode 323 is disposed on the surface 311 of the substrate 310, the counter electrode 330 and the second working electrode 324 are disposed on the opposite surface 312 of the substrate 310, and the surfaces of the first working electrode 323, the second working electrode 324 and the counter electrode 330 are covered by the chemical reagent 350. In this embodiment, the surface area of the first working electrode 323 can be increased to perform the measurement step, and the surface area of the second working electrode 324 can be decreased to perform the replenishment step to replenish silver halide to the counter electrode 330. Therefore, in this embodiment, when the measurement step is performed, a current flows from the first working electrode 323 to the counter electrode 330, so that an oxidation reaction occurs on the first working electrode 323 and the physiological signal is measured, and silver halide (AgX) in the counter electrode 330 is consumed and dissociated into silver (Ag) and halide ion ($X^-$). When the replenishment step is performed, a current flows from the counter electrode 330 to the second working electrode 324, so that an oxidation reaction occurs on the counter electrode 330 to cause the combination of silver and halide ion to replenish silver halide.

Figure 13D:
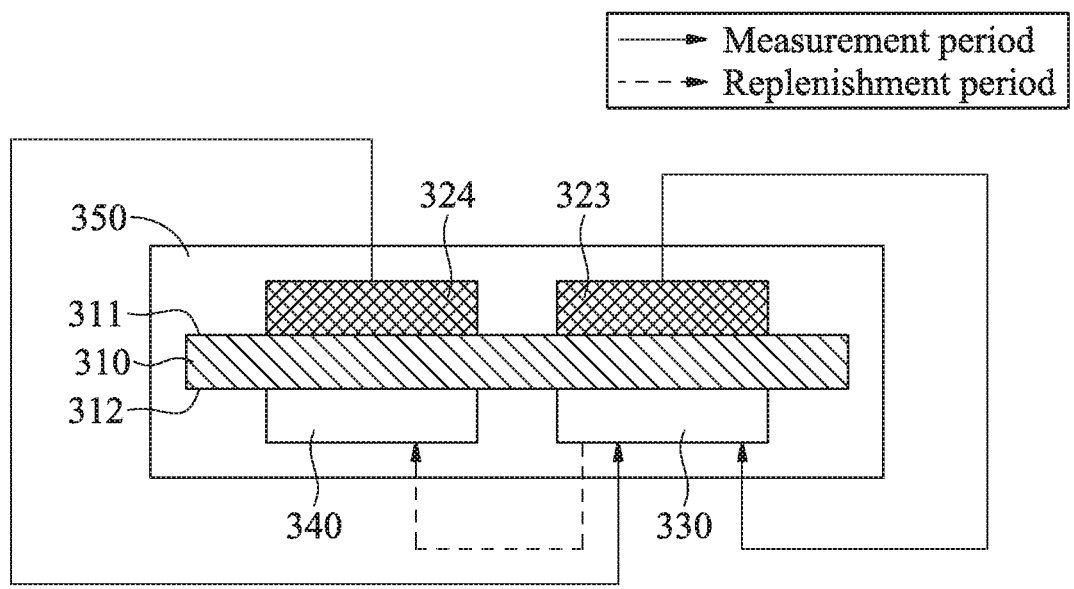
FIG. 13D shows a sectional schematic diagram of a fifth embodiment of the micro biosensor of the present invention.

Please refer to FIG. 13D, which is a sectional schematic diagram of a fifth embodiment of the micro biosensor of the present invention. The fifth embodiment is an addition of another working electrode in the first embodiment. Specifically, the micro biosensor 300 has two working electrodes, respectively are a first working electrode 323 and a second working electrode 324, one counter electrode 330 and one auxiliary electrode 340. In FIG. 13D, the first working electrode 323 and the second working electrode 324 are disposed on the surface 311 of the substrate 310, the counter electrode 330 and the auxiliary electrode 340 are disposed on the opposite surface 312 of the substrate 310, and the surfaces of the first working electrode 323, the second working electrode 324, the counter electrode 330 and the auxiliary electrode 340 are covered by the chemical reagent 350. One of the first working electrode 323 and the second working electrode 324 can be selected to measure the physiological signal in the measurement step, and the auxiliary electrode 340 forms the electronic circuit with the counter electrode 330 to replenish silver halide to the counter electrode 330 in the replenishment step. Therefore, in this embodiment, when the measurement step is performed, a current flows from the first working electrode 323 or the second working electrode 324 to the counter electrode 330, so that an oxidation reaction occurs on the first working electrode 323 or the second working electrode 324 and the physiological signal is measured, and silver halide (AgX) in the counter electrode 330 is consumed and dissociated into silver (Ag) and halide ion (X$^-$). When the replenishment step is performed, a current flows from the counter electrode 330 to the auxiliary electrode 340, so that an oxidation reaction occurs on the counter electrode 330 to cause the combination of silver and halide ion to replenish silver halide.

Figure 13E:
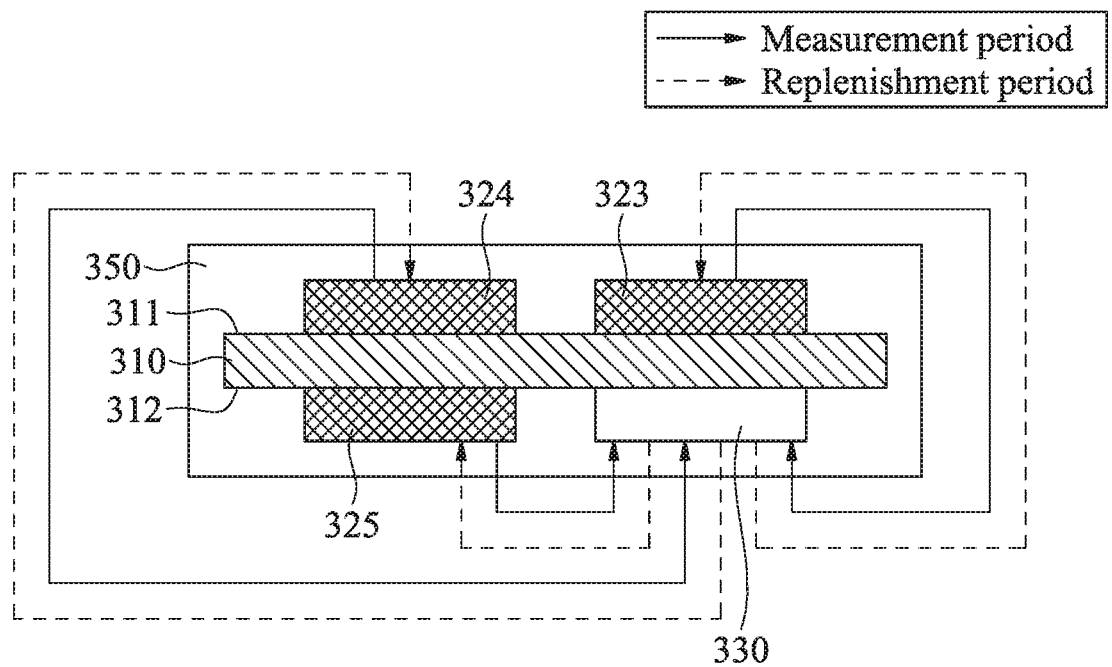
FIG. 13E shows a sectional schematic diagram of a sixth embodiment of the micro biosensor of the present invention.

Please refer to FIG. 13E, which is a sectional schematic diagram of a sixth embodiment of the micro biosensor of the present invention. In this embodiment, the micro biosensor 300 has three working electrodes which respectively are a first working electrode 323, a second working electrode 324 and a third working electrode 325, wherein the auxiliary electrode is replaced by the third working electrode 325. In FIG. 13E, the first working electrode 323 and the second working electrode 324 are disposed on the surface 311 of the substrate 310, the counter electrode 330 and the third working electrode 325 are disposed on the opposite surface 312 of the substrate 310, and the surfaces of the first working electrode 323, the second working electrode 324, the third working electrode 325 and the counter electrode 330 are covered by the chemical reagent 350. One of the first working electrode 323, the second working electrode 324 and the third working electrode 325 can be selected to measure the physiological signal in the measurement step, and the first working electrode 323, the second working electrode 324 or the third working electrode 32 forms the electronic circuit with the counter electrode 330 to replenish silver halide to the counter electrode 330 in the replenishment step. Therefore, in this embodiment, when the measurement step is performed, a current flows from the first working electrode 323, the second working electrode 324 or the third working electrode 325 to the counter electrode 330, so that an oxidation reaction occurs on the first working electrode 323, the second working electrode 324 or the third working electrode 325 and the physiological signal is measured, and silver halide (AgX) in the counter electrode 330 is consumed and dissociated into silver (Ag) and halide ion (X$^-$). When the replenishment step is performed, a current flows from the counter electrode 330 to the first working electrode 323, the second working electrode 324 or the third working electrode 325, so that an oxidation reaction occurs on the counter electrode 330 to cause the combination of silver and halide ion to replenish silver halide.

Figure 13F:
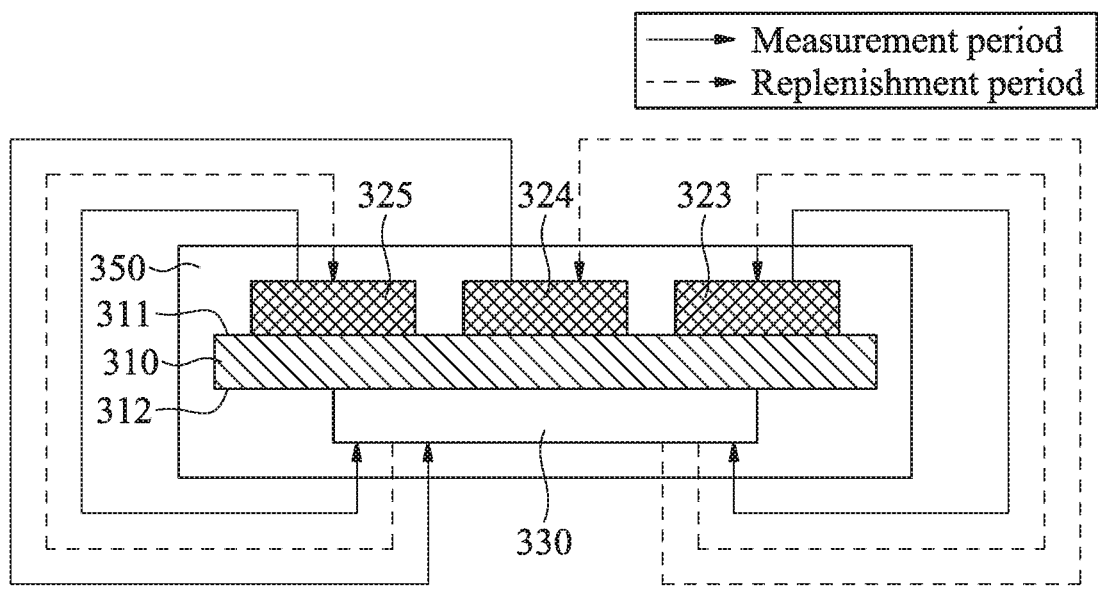
FIG. 13F shows a sectional schematic diagram of a seventh embodiment of the micro biosensor of the present invention.

Please refer to FIG. 13F, which is a sectional schematic diagram of a seventh embodiment of the micro biosensor of the present invention. The seventh embodiment is a variation of the electrode configuration of the sixth embodiment. In this embodiment, as shown in FIG. 13F, the first working electrode 323, the second working electrode 324 and the third working electrode 325 are disposed on the surface 311 of the substrate 310, the counter electrode 330 is disposed on the opposite surface 312 of the substrate 310, and the surfaces of the first working electrode 323, the second working electrode 324, the third working electrode 325 and the counter electrode 330 are covered by the chemical reagent 350. One of the first working electrode 323, the second working electrode 324 and the third working electrode 325 can be selected to measure the physiological signal in the measurement step, and the first working electrode 323, the second working electrode 324 or the third working electrode 32 forms the electronic circuit with the counter electrode 330 to replenish silver halide to the counter electrode 330 in the replenishment step. Therefore, in this embodiment, when the measurement step is performed, a current flows from the first working electrode 323, the second working electrode 324 or the third working electrode 325 to the counter electrode 330, so that an oxidation reaction occurs on the first working electrode 323, the second working electrode 324 or the third working electrode 325 and the physiological signal is measured, and silver halide (AgX) in the counter electrode 330 is consumed and dissociated into silver (Ag) and halide ion (X$^-$). When the replenishment step is performed, a current flows from the counter electrode 330 to the first working electrode 323, the second working electrode 324 or the third working electrode 325, so that an oxidation reaction occurs on the counter electrode 330 to cause the combination of silver and halide ion to replenish silver halide.

Figure 13G:
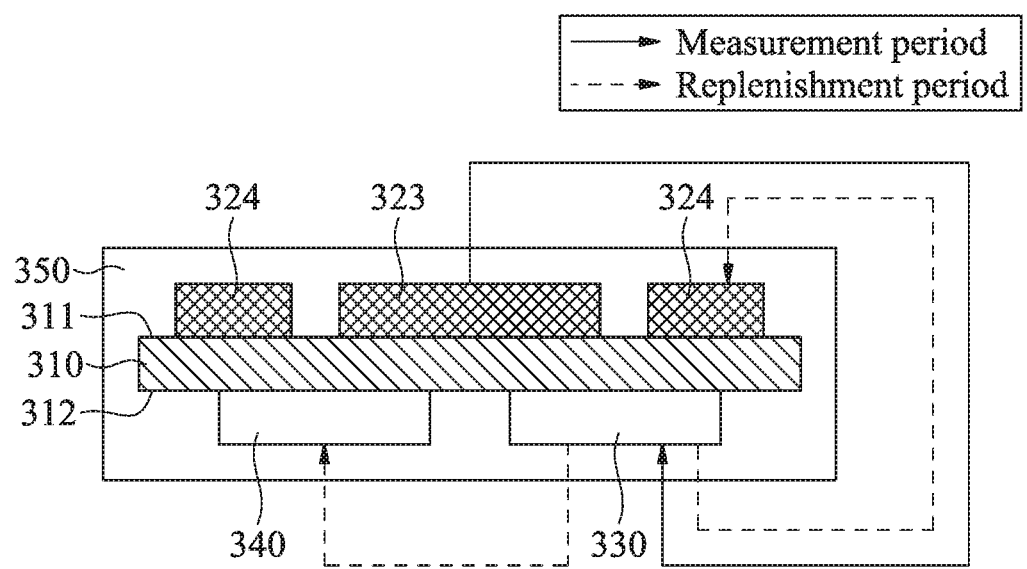
FIG. 13G shows a sectional schematic diagram of an eighth embodiment of the micro biosensor of the present invention.

Please refer to FIG. 13G, which is a sectional schematic diagram of an eighth embodiment of the micro biosensor of the present invention. Comparing with FIG. 13D, the difference is that the second working electrode 324 in FIG. 3G is U-shape. In the eighth embodiment, the first working electrode 323 and the second working electrode 324 are configured on the surface 311 of the substrate 310, the second working electrode 324 is adjacent to and around the first working electrode 323, and the counter electrode 330 and the auxiliary electrode 340 are disposed on the opposite surface 312 of the substrate 310. In this embodiment, when the measurement step is performed, a current flows from the first working electrode 323 to the counter electrode 330, so that an oxidation reaction occurs on the working electrode 320 and the physiological signal is measured, and silver halide (AgX) in the counter electrode 330 is consumed and dissociated into silver (Ag) and halide ion (X$^-$). When the replenishment step is performed, a current flows from the counter electrode 330 to the auxiliary electrode 340 or the second working electrode 324, so that an oxidation reaction occurs on the counter electrode 330 to cause the combination of silver and halide ion to replenish silver halide.

The detailed electrode stacks in FIGS. 12C-13G are omitted, and only the electrode positions are shown.

In any embodiment above, the substrate 310 of the present invention is an insulator. The electrode material of the working electrode 320 and the first working electrode 323 of the present invention includes but is not limited to: carbon, platinum, aluminum, gallium, gold, indium, iridium, iron, lead, magnesium, nickel, manganese, molybdenum, osmium, palladium, rhodium, silver, tin, titanium, zinc, silicon, zirconium, a mixture thereof, or derivatives thereof (such as alloys, oxides or metal compounds, etc.). Preferably, the materials of the working electrode 320 and the first working electrode 323 are a precious metal, a precious metal derivative or a combination thereof. More preferably, the working electrode and the first working electrode 323 are made of platinum-containing material. The materials of the second working electrode 324 and the third working electrode 325 can also use the elements or their derivatives as exemplified for the working electrodes 320 and the first working electrode 323 above. In another embodiment, the electrode materials of the second working electrode 324 and the third working electrode 325 can be materials having a lower sensitivity to hydrogen peroxide than that of the first working electrode 323, such as carbon.

Because the electrode material of the counter electrode 330 of the present invention includes silver and silver halide (Ag/AgX), the counter electrode 330 of the present invention includes functions of the counter electrode and the reference electrode of the common knowledge in the art. Specifically, the counter electrode 330 of the present invention can (1) form an electronic circuit with the working electrode 320 to cause the current between the counter electrode 330 and the working electrode 320 to be conducted to ensure that the electrochemical reaction occurs on the working electrode 320; (2) form an electronic circuit with the auxiliary electrode 340 to cause the current between the counter electrode 330 and the auxiliary electrode 340 to be conducted to ensure that the electrochemical reaction occurs on the counter electrode 330; and (3) provide a stable relative potential as a reference potential. Therefore, the working electrode 320, the counter electrode 330 and the auxiliary electrode 340 of the present invention form a 3-electrode system different from the traditional 3-electrode system.

When the electrode material of the auxiliary electrode 340 of the present invention is covered with platinum, the auxiliary electrode 340 also can be used as an electrode for measuring the physiological signal.

In any embodiment above, to prevent the silver electrode material from breakage due to over chlorination, a layer of conductive material, such as carbon, can be further disposed between the opposite surface 312 of the substrate 310 and the silver of the counter electrode 330. However, if the bottom layer of the counter electrode 330 is carbon, the resistance at a switch position will be too high. A conductive layer, such as silver, can be further disposed between the carbon conductive material and the opposite surface 312 of the substrate 310. Therefore, the material of the counter electrode 330 of the present invention sequentially is the conductive layer, the carbon layer and the silver/silver halide layer from the opposite surface 312 of the substrate 310.

Switching Applications of a Constant Voltage Circuit

Figure 14A:
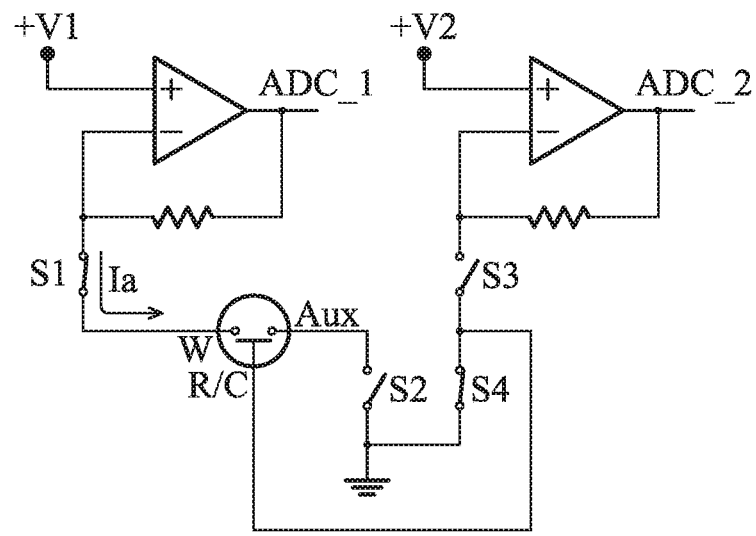
FIG. 14A shows a constant voltage circuit in a measurement mode in the present invention.
Figure 14B:
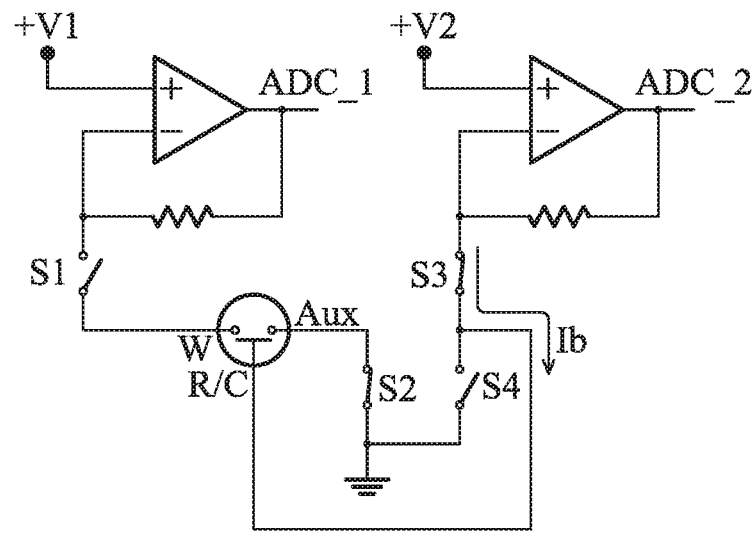
FIG. 14B shows a constant voltage circuit in a replenishment mode in the present invention.
Figure 15A:
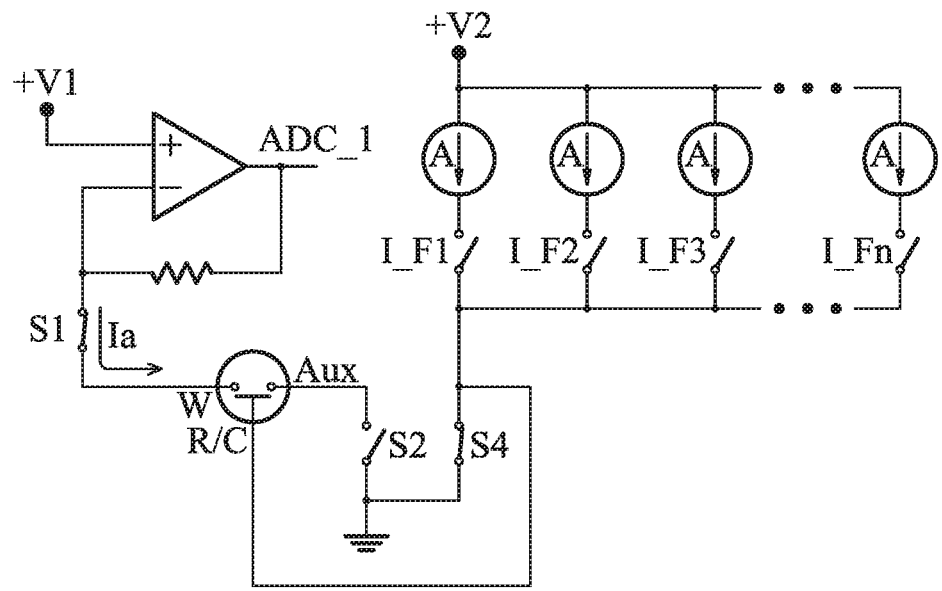
FIG. 15A shows a segmental constant current circuit in a measurement mode in the present invention.
Figure 15B:
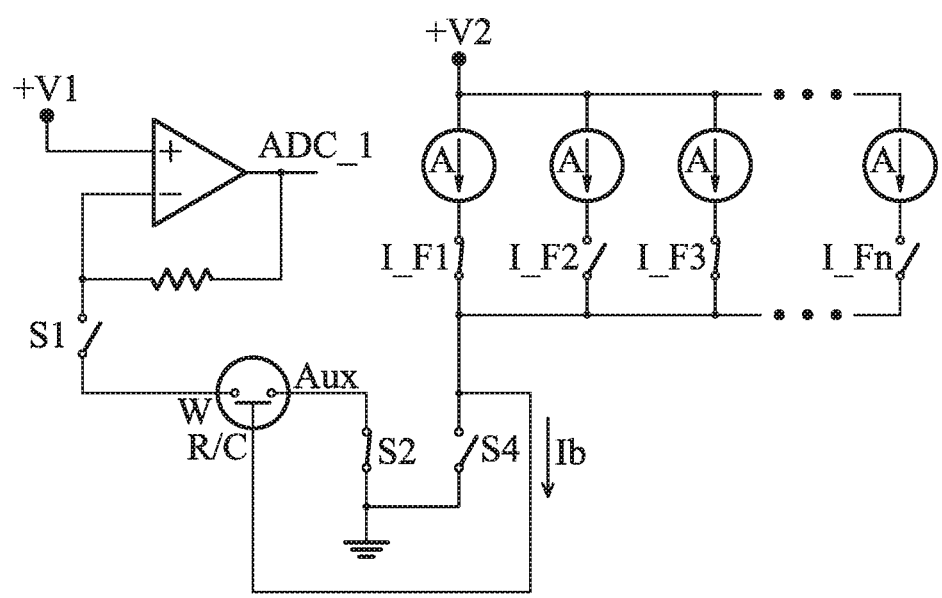
FIG. 15B shows a segmental constant current circuit in a replenishment mode in the present invention.
Figure 16A:
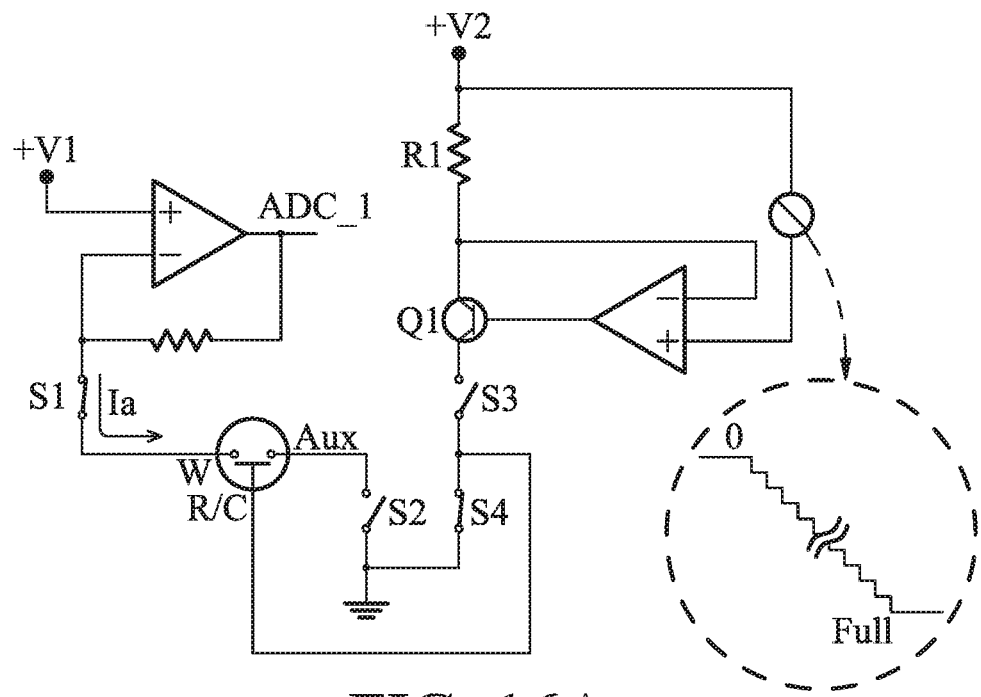
FIG. 16A shows a continuous variable constant current circuit in a measurement mode in the present invention.
Figure 16B:
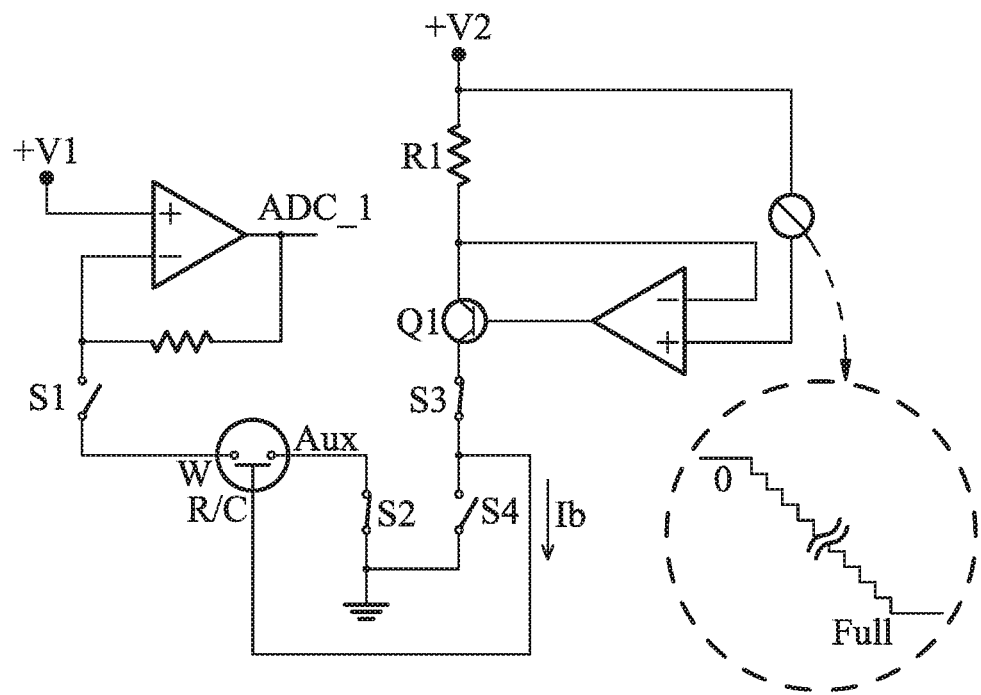
FIG. 16B shows a continuous variable constant current circuit in a replenishment mode in the present invention.

Please refer to FIGS. 14A-14B and FIGS. 5A-5D, wherein FIGS. 14A and 14B show a constant voltage circuit in a measurement mode and a replenishment mode, respectively, in the present invention, and FIGS. 5A-D respectively show the current schematic diagrams of the constant voltage circuit running in the measurement mode and the replenishment mode by turns in different ways. The measurement mode can be started and stopped by applying a measurement potential difference V1 and removing the measurement potential difference V1, respectively, and the corresponding current is represented by Ia. In the measurement mode, the measurement potential difference V1 is applied across the working electrode W and the counter electrode R/C during the measurement period T1, so that the voltage of the working electrode W is higher than that of the counter electrode R/C. During the measurement mode, as shown in FIG. 14A, the switches S1 and S4 are in the close circuit state, the switches S2 and S3 are in the open circuit state, the working electrode W is +V1, the auxiliary electrode Aux is in the open circuit state, and the counter electrode R/C is grounded, so that at the working electrode W, an oxidation reaction occurs, and the working electrode W electrochemically reacts with chemical reagents and an analyte to output a physiological signal Ia. The AgCl in the counter electrode R/C has a consumption amount corresponding to the physiological signal Ia. As shown in FIGS. 5A-5D, between any two of a plurality of measurement periods T1 is a period T2 during which no measurement is performed. In some preferred embodiments, T2 is a constant value.

The replenishment mode can be started and stopped by applying a replenishment potential difference V2 and removing the replenishment potential difference V2, respectively, and the corresponding current is represented by Ib. V2 is a constant value in a range of 0.1V to 0.8V, preferably range of 0.2V to 0.5V. In the replenishment mode, the replenishment potential difference V2 is applied across the auxiliary electrode Aux and the counter electrode R/C during the replenishment period t2 (t2 is in a range of 0 to T2), so that the voltage of the counter electrode R/C is higher than that of the auxiliary electrode Aux. During the replenishment mode, as shown in FIG. 14B, the switches S1 and S4 are in the open circuit state, the switches S2 and S3 are in the close circuit state, the working electrode W in the open circuit state, the auxiliary electrode Aux is grounded, and the counter electrode R/C is +V2, so that on the counter electrode R/C, an oxidation reaction of Ag occurs to replenish the counter electrode R/C with AgCl by a replenishment amount. In the constant voltage circuit, the replenishment potential difference V2 is a constant voltage, and the measured output current is Ib. In the present invention, the amount or value of capacity (with the unit "coulomb" and represented by the symbol "C") of AgCl is defined by calculating the area under the current curve, so the consumption amount of AgCl in the measurement mode is Ia*T1, and the replenishment amount of AgCl in the replenishment mode is Ib*t2. In such case, the replenishment amount of AgCl can be controlled by adjusting the period t2 during which the potential difference V2 is applied. In other words, on the premise that the AgCl on the counter electrode R/C is kept within the safe storage range, the replenishment amount can be equal to or not equal to (including approximately similar, greater than or less than) consumption amount.

In FIGS. 5A-5D, the horizontal axis represents time, the curve for V1 represents the application and removal of the measurement potential difference V1, and the curve for V2 represents the application and removal of the replenishment potential difference V2. Please refer to FIG. 5A. In a preferred embodiment, both V2 and T2 are constant values, and the period t2 (i.e., the replenishment period) during which V2 is applied is a variable value. The replenishment period t2 is dynamically adjusted in a range of 0 to T2 according to the physiological signal Ia measured in the measurement mode and during the measurement period T1. As shown in FIG. 5A, t2 can be t2', t2", or t2'" . . . . In other words, the replenishment period t2 can be changed according to the consumption amount of AgCl. In the condition of a high consumption amount of AgCl, the counter electrode R/C can be replenished for a longer time to keep the AgCl on the counter electrode R/C within the safe storage range. For example, the amount of AgCl replenished during t2" will be greater than the amount of AgCl replenished during t2'.

Please refer to FIG. 5B, in another preferred embodiment, V2, T2 and t2 are all constant values, wherein t2=T2. That is, the measurement mode and replenishment mode alternate seamlessly, and the period during which no measurement is performed is the replenishment period. Please refer to FIGS. 5C and 5D, in some preferred embodiments, V2, T2, and t2 are constant values, wherein t2 is a constant value greater than 0 and less than T2. For example, t2=½ T2, ⅖ T2, ⅗ T2, etc. The difference between FIG. 5C and FIG. 5D is that in FIG. 5C, after each measurement mode, a buffer time (buffer time=T2−t2) is passed before the replenishment mode starts; and in FIG. 5D, after each measurement mode, the replenishment mode starts immediately without any buffer time, and there is a period of time between the end of each replenishment mode and the start of the next measurement mode. In some preferred embodiments, t2 is less than T2, and t2 can be any time period during T2.

Please refer to FIGS. 5E and 5F, which show current-time schematic diagrams of the constant voltage circuit running in the measurement mode and the replenishment mode by turns in different ways. In FIGS. 5E and 5F, the horizontal axis represents time, the vertical axis represents current, and the curve represents the physiological parameter curve calculated from the measured physiological signal Ia. In the two embodiments, similar to that in FIG. 5A, V2 and T2 are constant values and the replenishment period t2 is a variable value. In FIGS. 5E and 5F, the white area under the curve represents the AgCl consumption amount in the measurement mode (Ia*Tl), and the oblique area represents the replenishment amount of AgCl in the replenishment mode (Ib*t2). It can be seen from the figures that in order to make Ib*t2 close to Ia*Tl or within a certain range of Ia*Tl, the replenishment period t2 is dynamically adjusted in a range of 0 to T2 according to the measured physiological signal Ia and the measurement period T1. According to requirements, the front part (as shown in FIG. 5E) or the back part (as shown in FIG. 5F) of the period (T2) where the measurement mode is not executed can be selected to perform the replenishment mode.

Switching Applications of a Segmental Constant Current Circuit

Please refer to FIGS. 6A-6B and FIGS. 8A-8C, wherein FIGS. 6A and 6B show a segmental constant current circuit in a measurement mode and a replenishment mode, respectively, according to the present invention, and FIGS. 8A-8C respectively show the voltage schematic diagrams of the constant current circuit running in the measurement mode and the replenishment mode by turns in different ways. The measurement mode can be started and stopped by applying a measurement potential difference V1 and removing the measurement potential difference V1, respectively, and the corresponding current is represented by Ia. In the measurement mode, the measurement potential difference V1 is applied across the working electrode W and the counter electrode R/C during the measurement period T1. During the measurement mode, as shown in FIG. 6A, the switches S1 and S4 are in the close circuit state, the remaining switches are in the open circuit state, the working electrode W is +V1, the auxiliary electrode Aux is in the open circuit state, and the counter electrode R/C is grounded, so that at the working electrode W, an oxidation reaction occurs, and the working electrode W electrochemically reacts with chemical reagents and an analyte to output a physiological signal Ia. The AgCl in the counter electrode R/C has a consumption amount corresponding to the physiological signal Ia. As shown in FIGS. 8A-8C, between any two of a plurality of measurement periods T1 is a period T2 during which no measurement is performed. In some preferred embodiments, T2 is a constant value.

The replenishment mode can be started and stopped by applying a replenishment potential difference V2, which is a variable value, and removing the replenishment potential difference V2, respectively, and the corresponding current is represented by Ib. In the replenishment mode, the replenishment potential difference V2 is applied across the auxiliary electrode Aux and the counter electrode R/C during the replenishment period t2 (wherein t2 is in a range of 0 to T2). During the replenishment mode, as shown in FIG. 6B, the switches S1 and S4 are in the open circuit state, the switch S2 and at least one of switches corresponding to I_F1 to I_Fn are in the close circuit state (wherein FIG. 6B exemplarily shows that the switches corresponding to I_F1 and I_F3 are in the close circuit state), the working electrode W is in the open circuit state, the auxiliary electrode Aux is grounded, and the counter electrode R/C is +V2, so that on the counter electrode R/C, an oxidation reaction of Ag occurs to replenish the counter electrode R/C with AgCl. In the replenishment mode, according to the magnitude of the physiological signal Ia and the measurement period T1, at least one of the switches corresponding to I_F1 to I_Fn can be selected to be turned on to output a constant current Ib, and the replenishment amount of AgCl can be controlled by adjusting the period t2 during which the potential difference V2 is applied. That is, on the premise that the AgCl on the counter electrode RIC is kept within the safe storage range, the replenishment amount can be equal to or not equal to (including approximately similar, greater than or less than) consumption amount.

Switching Applications of a Continuous Variable Constant Current Circuit.

Please refer to FIGS. 7A-7B and FIGS. 8A-8C, wherein FIGS. 7A and 7B show a continuous variable constant current circuit in a measurement mode and a replenishment mode, respectively, according to the present invention. The measurement mode and the replenishment mode in this embodiment are similar to those in FIGS. 6A and 6B, so they will not be repeated here. This embodiment differs from that in FIGS. 6A and 6B only in that in the replenishment mode of this embodiment, according to the physiological signal Ia, a constant current Ib can be output by the control of the digital-to-analog converter (DAC), and the replenishment amount of AgCl can be controlled by adjusting the period t2 during which the potential difference V2 is applied. That is, on the premise that the AgCl on the counter electrode R/C is kept within the safe storage range, the replenishment amount can be equal to or not equal to (including approximately similar, greater than or less than) consumption amount.

In FIGS. 8A-8C, the horizontal axis represents time, the vertical axis represents current, the curve for V1 represents the application and removal of the measurement potential difference V1, and the curve for V2 represents the application and removal of the replenishment potential difference V2. Please refer to FIG. 8A, in a preferred embodiment, T2 is a constant value, V2 and the period t2 (i.e., the replenishment period) during which V2 is applied are variable values. The replenishment period t2 is dynamically adjusted in a range of 0 to T2 according to the measurement period T1 and the physiological signal Ia measured in the measurement mode. As shown in FIG. 8A, t2 can be t2', t2" or t2'' . . . . In other words, the replenishment period t2 can be changed according to the consumption amount of AgCl. In the condition of a high consumption amount of AgCl, the counter electrode R/C can be replenished for a longer time to keep the AgCl on the counter electrode R/C within the safe storage range.

Please refer to FIG. 8B, in another preferred embodiment, V2 is a variable value, and T2 and t2 are constant values, wherein t2 is a constant value greater than 0 and less than T2. For example, t2 can be ½ T2, ⅖ T2, ⅗ T2, etc. In this embodiment, V2 is dynamically adjusted according to the consumption amount of AgCl in the step of measuring the physiological signal (i.e., in the measurement mode). One example of the dynamic adjustment method is as follows. For example, the segmental constant current circuit is used. The circuit includes n constant current supplies and n switches, and each constant current supply corresponds to a switch. In the replenishment mode, according to the consumption amount of AgCl, at least one of the n switches is selected to be turned on (i.e., in the close circuit state) to output a constant current value. When the replenishment period t2 is a constant value, the replenishment amount of AgCl can be controlled by selecting different constant current outputs.

Please refer to FIG. 8C, in another preferred embodiment, V2 is a variable value, T2 and t2 are constant values, wherein t2=T2. That is, the measurement mode and replenishment mode alternate seamlessly, and the period during which no measurement is performed is the replenishment period.

Compared with the continuous variable constant current circuit, in the segmental constant current circuit, multiple current paths can be controlled through multiple switches, and thus the replenishment can be performed by multi-segment constant current according to the amount of current required. The multi-segment constant current, in this way, saves electricity and can reduce costs. In addition, whether it is a constant voltage circuit or a constant current circuit, the potential difference can come from a DC power supply or an AC power supply, preferably from a DC power supply.

The embodiments of FIGS. 5A-5F, 6A-6B, 7A-7B and 8A-8C all involve the operation manner of alternately cycling measurement step and replenishment step, which means that there is an AgCl replenishment step between any two measurement steps. Such manner can better ensure that AgCl remains within the safe storage range. However, in some preferred embodiments, Y times of AgCl replenishment can be optionally performed during N measurements, where Y≤N, in such a way that the accumulated replenishment amount of AgCl can still be kept within the safe storage range. The measurement step and the replenishment step do not necessarily need to be performed in an alternate cycle. A replenishment step can also be performed after several measurement steps, or after a predetermined measurement time. For example, a replenishment step can be performed after 10 measurement steps, or after the accumulated measurement time reaches 1 hour.

Please refer to FIG. 8D, which shows a current-time schematic diagram of the constant current circuit running in the measurement mode and the replenishment mode by turns in a way similar to that of FIG. 8C. In FIG. 8D, the curve represents the physiological parameter curve calculated from the measured physiological signal Ia, the conditions of T2 and t2 being both constant values and V2 being a variable value are similar to those in FIG. 8C. In FIG. 8D, the white area under the curve represents the AgCl consumption amount in the measurement mode (Ia*T1), and the oblique area represents the replenishment amount of AgCl in the replenishment mode (Ib*t2). It can be seen from this figure that in order to make Ib*t2 close to Ia*T1 or within a certain range of Ia*T1, the replenishment potential difference V2 is dynamically adjusted according to the consumption amount of AgCl.

In addition, although FIGS. 5E, 5F, and 8D do not show the output timing of each physiological parameter value after each measurement step for measuring a physiological signal is performed, the physiological parameter value may be output, but is not limited to, when the measurement is completed or during the replenishment period and the AgCl replenishment step may be performed after every physiological parameter is output or after obtaining the physiological signal, but is not limited thereto.

In a two-electrode system including a working electrode W and a counter electrode R/C, the working electrode W must continuously switch between performing an oxidation reaction and performing a reduction reaction. In the chemical reaction environment of the electrodes, the switching between oxidation and reduction reactions must go through a stabilization period, such as several seconds or minutes. In contrast, in a three-electrode system including a working electrode W, a counter electrode R/C, and an auxiliary electrode Aux, the loop involving the working electrode W and the counter electrode R/C can be used for the measurement step, and the loop involving the auxiliary electrode Aux and the counter electrode R/C can be used for the replenishment step, and thus the disadvantage that the working electrode W needs a stabilization period is avoided. That is, the replenishment step can be performed immediately after the measurement step.

Please refer to FIG. 9, which shows a method of measuring an analyte according to the present invention. A usage lifetime of a micro biosensor can be prolonged by the method. The micro biosensor, which may be, for example, the micro biosensor shown in FIG. 2A to FIG. 3, is used to be implanted subcutaneously to measure a physiological signal representative of a physiological parameter associated with the analyte in a biofluid (such as tissue fluid). In the embodiment of FIG. 9, the analyte can be glucose in the tissue fluid, the physiological parameter is the glucose level in the human body, and the physiological signal is a current value measured by the micro-biological sensor. In this embodiment, the method for measuring the analyte includes repeatedly performing the measurement step (S901) and the replenishment step (S902). The measurement step (S901) includes using the aforementioned constant voltage circuit or the constant current circuit to perform the aforementioned measurement mode during the measurement period T1 to output a physiological signal (i.e., a current value), and at the same time, the AgCl on the counter electrode has a consumption amount corresponding to the current value. The measurement step (S901) also includes stopping the measurement step by stopping the measurement mode, and the current value is calculated to output a physiological parameter (i.e., glucose level).

In the measurement step (S901), the chemical equations are as follows.
The following oxidation reactions occur at the working electrode 320.

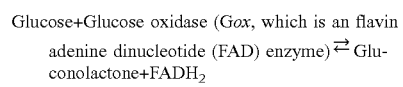
Glucose+Glucose oxidase (Gox, which is an flavin adenine dinucleotide (FAD) enzyme) $\rightleftarrows$ Gluconolactone+FADH$_2$

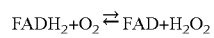
FADH$_2$+O$_2$ $\rightleftarrows$ FAD+H$_2$O$_2$

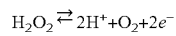
H$_2$O$_2$ $\rightleftarrows$ 2H$^+$+O$_2$+2$e^-$

The following reduction reactions occur at the counter electrode 330.

$$2AgCl + 2e^- \rightleftarrows 2Ag + 2Cl^-$$

The replenishment step (S902) includes using the aforementioned constant voltage circuit or constant current circuit to perform the aforementioned replenishment mode during the replenishment period, such that the AgCl on the counter electrode has a replenishment amount corresponding to consumption amount, and thus the AgCl on the counter electrode has an amount controlled within a safe storage range. As a result, the potential difference between the working electrode and the counter electrode can be kept stable, so that the obtained current value can still maintain a stable correlation with the glucose value (if the detected substance is other analytes, the correlation may be proportional or inverse correlation). In other words, it is possible to keep a stable correlation between a next current value obtained in a next measurement step and a next glucose value. The replenishment step (S902) also includes a step of stopping the replenishment step by stopping the aforementioned replenishment mode. After the replenishment step (S902) is finished, the method returns to the measurement step (S901) until N measurement steps (S901) and N replenishment steps (S902) are executed.

In the replenishment step (S902), the chemical equations are as follows. The following reduction reactions occur at the auxiliary electrode.

Glucose+Glucose oxidase (Gox, which is an flavin adenine dinucleotide (FAD) enzyme) $\rightleftarrows$ Gluconolactone+FADH$_2$ $$FADH_2 + O_2 \rightleftarrows FAD + H_2O_2$$

$$H_2O_2 + 2H^+ + 2e^- \rightleftarrows H_2O$$

$$O_2 + 4H^+ + 4e^- \rightleftarrows 2H_2O$$

The positive potential on the counter electrode 330 cause the following oxidation reactions occurring at the counter electrode 330.

$$2Ag \rightleftarrows 2Ag^+ + 2Cl^- \rightleftarrows 2AgCl + 2e^-$$

The Ag on the counter electrode is oxidized to Ag$^+$ and combined with Cl$^-$ from the body or from oxidation (or dissociation) of AgCl to form AgCl, such that part or all of the AgCl consumed during the measurement period T1 is replenished onto the counter electrode.

Human can intake chloride ions and iodide ions through iodine-doped salts. The available halide ions include at least chloride ions and iodide ions for replenishing the counter electrode with silver halide.

The following embodiments are directed to cycles of N measurement steps (S901) and N replenishment steps (S902). The physiological parameter mentioned is preferably a glucose value, and the physiological signal mentioned is preferably a current value. According to some preferred embodiments, each measurement potential difference V1 is applied during the measurement period T1, each replenishment potential difference V2 is applied during the replenishment period t2, and the measurement period T1 is a constant value, which can be a value within 3 seconds, 5 seconds, 10 seconds, 15 seconds, 30 seconds, 1 minute, 2.5 minutes, 5 minutes, 10 minutes, or 10 minutes. According to some preferred embodiments, the constant value may be a value within 30 seconds. The measurement period T1 is a constant value, and can be 2.5 seconds, 5 seconds, 15 seconds, 30 seconds, 1 minute, 2.5 minutes, 5 minutes, 10 minutes, or 30 minutes, preferably 30 seconds. According to some preferred embodiments, each measurement period T1 plus each replenishment period t2 is a constant value. According to some preferred embodiments, each replenishment potential difference V2 has a constant voltage value, and each replenishment period t2 is dynamically adjusted according to each consumption amount of AgCl (as shown in FIG. 5A). According to some preferred embodiments, each output physiological parameter is obtained through calculation of the physiological signals at a single measurement time point in each measurement period T1. According to some preferred embodiments, each output physiological parameter is obtained through a mathematical operation value of a plurality of physiological signals at a plurality of measurement time points in each measurement period T1. The aforementioned mathematical operation value is, for example, a accumulated value, an average value, a median value, an average value of median, and so on. According to some preferred embodiments, the replenishment amount of AgCl on the counter electrode is controlled within a safe storage range by controlling each replenishment amount to be equal to or not equal to (including approximately similar, greater than or less than) each consumption amount. As a result, a next physiological signal obtained during a next measurement step maintains a stable proportional correlation with a next physiological parameter. According to some preferred embodiments, the step of removing each measurement potential difference V1 is to disconnect the circuit that connects the working electrode and the counter electrode, or set each measurement potential difference V1 to zero. In other words, the power can be turned off to make the measurement circuit have an open circuit state; or, a 0 volt voltage can be applied across the working electrode and the counter electrode, wherein the operation time of either of the two operations is 0.01~0.5 seconds. The step of removing the measurement potential difference V1 can avoid the generation of A-shaped physiological signals. According to some preferred embodiments, the step of removing each replenishment potential difference V2 is to disconnect the circuit configured to connect the auxiliary electrode and the counter electrode, or set each replenishment potential difference V2 to zero.

According to some preferred embodiments, after the biosensor is implanted in the human body, a warm-up time is required for the biosensor to be in the condition of equilibrium and stability in the body in order to stably present a physiological signal that is positively correlated with an analyte concentration. Therefore, in the measurement step (S901), the measurement voltage is continuously applied until the end of the measurement period T1, and the measurement period T1 is controlled such that the physiological signal and the physiological parameter of the analyte have a stable proportional correlation. To this end, the measurement period T1 can be a variable value or a combination of a variable value and a constant value (for example, a variable value plus a constant value, in which the variable value may be 1 hour, 2 hours, 3 hours, 6 hours, 12 hours or 24 hours, and the constant value may be, for example, 30 seconds).

Please refer to FIGS. 5A-5F, 8A-8D and 9. The present invention uses a voltage applied to the counter electrode R/C during a period to measure a resultant current of the counter electrode, and the initial capacity of AgCl is obtained by mathematical calculation of the resultant current during the period. For example, the initial capacity of AgCl is defined by calculating area under a curve of the resultant current. The initial capacity of AgCl is also referred to as the initial amount or initial coulomb amount ($C_{initial}$), the following are all described by amount. The counter electrode R/C contains Ag and AgCl. When the amount of AgCl (X % AgCl) is known, the amount of Ag can be calculated (Y % Ag=100%−X % AgCl). In each measurement step (S901), the consumption amount of AgCl (denoted by $C_{consume}$) is defined by calculating the area under the current curve of the working electrode W. The AgCl of the counter electrode R/C has a consumption amount $C_{consume}$ corresponding to the physiological signal Ia, i.e., $C_{consume}$=Ia*T1. In each replenishment step (S902), each replenishment amount (denoted by $C_{replenish}$) of AgCl is defined by calculating the area under the current curve of the counter electrode R/C, i.e., $C_{replenish}$=Ib*t2, where t2 is a value in a range of 0~T2.

The calculation method of AgCl safe storage amount is described below. In some preferred embodiments, the safe storage range is represented by the ratio of Ag to AgCl. The present invention uses the coulomb amount (C) measured at the counter electrode to reflect the ratio of Ag to AgCl. In some preferred embodiments, the ratio of Ag to AgCl is 99.9%:0.1%, 99%:1%, 95%:5%, 90%:10%, 70%:30%, 50%:50%, 40%:60% or 30:70%, which assure of a certain amount of the AgCl on the counter electrode without being exhausted, and thus each measurement step for measuring the physiological signal can be performed stably. The remaining amount of AgCl is the sum of the replenishment amount and the initial amount minus the consumption amount. In some preferred embodiments, the remaining amount of AgCl varies within a range, that is, the remaining amount of AgCl is controlled within a range of the initial amount plus or minus a specific value (X value). Namely, $(C_{replenish}+C_{initial})-C_{consume}=C_{initial}\pm X$, where 0<X<100% $C_{initial}$, 10% $C_{initial}<X\leq90\% C_{initial}$, or 0.5% $C_{initial}<X\leq50\% C_{initial}$. In some preferred embodiments, the remaining amount of AgCl may, within a range, gradually decrease, gradually increase, change steadily, or change arbitrarily but still within the range.

Please refer to FIG. 10, which shows a method for measuring an analyte according to another embodiment of the present invention. Through this method, the usage lifetime of the micro biosensor can be prolonged and the amount of silver and silver halide materials of the counter electrode can be reduced. The micro biosensor, which may be, for example, the micro biosensor shown in FIG. 12A-12C and FIG. 13A-13G, is used to be implanted subcutaneously to measure a physiological signal representative of a physiological parameter associated with the analyte in a biofluid (such as tissue fluid). The electrode material of the counter electrode of the micro biosensor includes silver and silver halide. In the embodiment of FIG. 10, the analyte can be glucose in tissue fluid, the physiological parameter is the glucose value in the human body, and the physiological signal is a current value measured by the micro biosensor. Only one cycle of this embodiment is described below. The method of this embodiment starts with the step of applying a measurement voltage to drive a working electrode to measure a physiological signal for obtaining a physiological parameter, wherein a specific amount of silver halide is consumed (hereinafter referred to as "consumption amount") (S1001).

Then the step of applying the measurement voltage is stopped (S1002), and the obtained physiological signal is used to obtain a physiological parameter (S1003). After the physiological parameter is obtained, a replenishment voltage is applied across a counter electrode and a auxiliary electrode to drive a counter electrode, such that silver halide is replenished by a replenishment amount (S1004), wherein a value (i.e., the aforementioned "remaining amount") of a sum of the replenishment amount and an initial amount minus the consumption amount is controlled within a range of the initial amount plus or minus a specific value. The above control step is achieved by controlling the replenishment amount to be equal to or not equal to (including approximately similar, greater than or less than) the consumption amount so as to maintain the amount of silver halide within a safe storage range. According to the chemical equations, the increase or decrease of the mole number of silver halide corresponds to the increase or decrease of the mole number of silver. Therefore, for the ease of descriptions, the consumption amount of silver halide corresponds to a simulated increased amount of silver. In some preferred embodiments, a value of the remaining amount is controlled such that the ratio of the amount of silver halide to the sum of the amount of silver halide plus the amount of silver (AgCl/Ag+AgCl) is greater than 0 and less than 1 (which means that there should be a certain amount of silver halide in the counter electrode), preferably between 0.01-0.99, between 0.1-0.9, between 0.2-0.8, between 0.3-0.7, or between 0.4-0.6. When the replenishment amount is reached, the step of applying the replenishment voltage is stopped (S1005). Then the method returns to step S1001 to execute the next loop.

A specific embodiment of the present invention will be described below. Taking a usage lifetime of a biosensor must reach 16 days as an example. To this end, the method to calculate the required size of Ag/AgCl material on a signal sensing section of a electrode is described below. For example, the average of the measured current of the analyte for each measurement is 30 nA, the measurement period (T1) is 30 seconds, and the replenishment period (t2) is 30 seconds. The daily consumption amount of AgCl ($C_{consume/day}$)=1.3 mC/day. Assuming that the requirement of a usage lifetime of a biosensor is 16 days, the consumption amount of AgCl required for using 16 days is 1.3× 16=20.8 mC.

For example, the length of the counter electrode is 2.5 mm, which corresponds to the initial amount of AgCl $C_{initial}$=10 mC.

(3) On a condition that AgCl replenishment is not performed, for the sensor usage lifetime of 16 days, the required length of the counter electrode is at least:

$C_{16day}/C_{consume/day}$=20.8 mC/1.3 mg/day=16 mm.

(4) Therefore, on a condition that the replenishment method for the silver halide in the present application is not performed, the length of the counter electrode needs to exceed 16 mm in order to make the usage lifetime of the sensor achieve 16 days.

In this embodiment, on a condition that the replenishing technique for silver halide in the present invention is not used, the signal sensing section of the counter electrode needs to be configured with a relatively large size of Ag/AgCl material to achieve the usage lifetime of 16 days. Through the replenishment method for silver halide in the present invention, the replenishment step for silver halide is performed between two measurement steps. The consumption and replenishment of the silver halide cycles repeated in a short period of time (replenished when used), so the amount of Ag/AgCl material in the sensor can be reduced, and thereby the sensor is miniaturized. Therefore, there is no need to prepare 16 days of AgCl capacity for the signal sensing section material of the electrode for consumption. For example, the preparation of the capacity of AgCl for about 1-2 days can achieve a usage time of 16 days of the sensor. Thus, the present invention has the effect of prolonging the usage lifetime of the sensor. The capacity of AgCl for 1-2 days also refers to the initial amount of AgCl in the counter electrode before leaving the factory or before performing the first measurement. The initial amount of AgCl may be, for example, between about 1.3 and 2.6 mC, and can be in other smaller range or a larger range. In other embodiments, different AgCl capacities for 1-5 days, 1-3 days, 6-24 hours, and 6-12 hours can also be prepared. The size of the signal sensing section of the counter electrode can be configured in such a way that the counter electrode has a capacity which enables stable executions of each measurement step for glucose and the positive correlation between the measurement current and the glucose concentration in the body.

The prior art increased the electrode length/area to make the sensor reach the required measurement days without using the silver chloride replenishment technology of the present invention. For example, the length of the implantation end of the prior art is about 12 mm. Due to the long implantation length of the prior art, the implantation end needs to be implanted subcutaneous at an oblique angle to avoid the implantation end from implanting deeply into the subcutaneous tissue, which causes a large implantation wound. For another example, the capacity of AgCl for 1~2 days is about 1.3~2.6 mC, the length of the counter electrode for 1~2 days is 2.5~5 mm after conversion, and thus the length of the counter electrode needs 16 mm without using the replenishment method for silver halide in the present invention. Comparing to the example above, it is obvious that the present invention has more significant effect on shortening the size of the counter electrode. According to the silver chloride replenishment step of the present invention, the implantation end of the present invention can be shortened, for example, to no greater than 10 mm. Please refer to FIGS. 12A-12C, the lower half of the connecting area 317 to the second end 314 of the micro biosensor 300 of the present invention forms a short implantation end 318, as shown in FIGS. 12A and 12B. The implantation depth of the short implantation end 318 is at least a depth to the dermis where can measure the glucose concentration in the tissue fluid. According to the silver chloride replenishment step of the present invention, a length of the longest side of the short implantation end 318 is no greater than 6 mm, so that the short implantation end 318 of the micro biosensor 300 can be perpendicularly implanted under the biological epidermis. Preferably, the length of the longest side of the short implantation end 318 is no greater than 5 mm, 4.5 mm, 3.5 mm or 2.5 mm. The short implantation end 318 of the present invention includes the signal sensing section 332 of the counter electrode 330, and a length of the longest side of the signal sensing section 332 of the counter electrode 330 is no greater than 6 mm, preferably 2-6 mm, 2-5 mm, 2-4.5 mm, 2-3.5 mm, 0.5-2 mm or 0.2-1 mm.

Therefore, compared with the cases where the silver halide replenishment technique of the present invention is not used, the silver halide replenishment method of the present invention can effectively extend the micro sensor's usage lifetime, and can also greatly reduce the use of Ag/AgCl material on the counter electrode, which causes the size of the signal sensing section of the counter electrode to be reduced. Because of the reduced use of the Ag/AgCl material on the counter electrode, the sensor can be miniaturized and biological toxicity can be reduced. In addition, the reduced size of the electrode specifically refers to the shortened length of the implantation end of the sensor, which would reduce pain for the user during implantation.

Embodiment III

Figure 17:
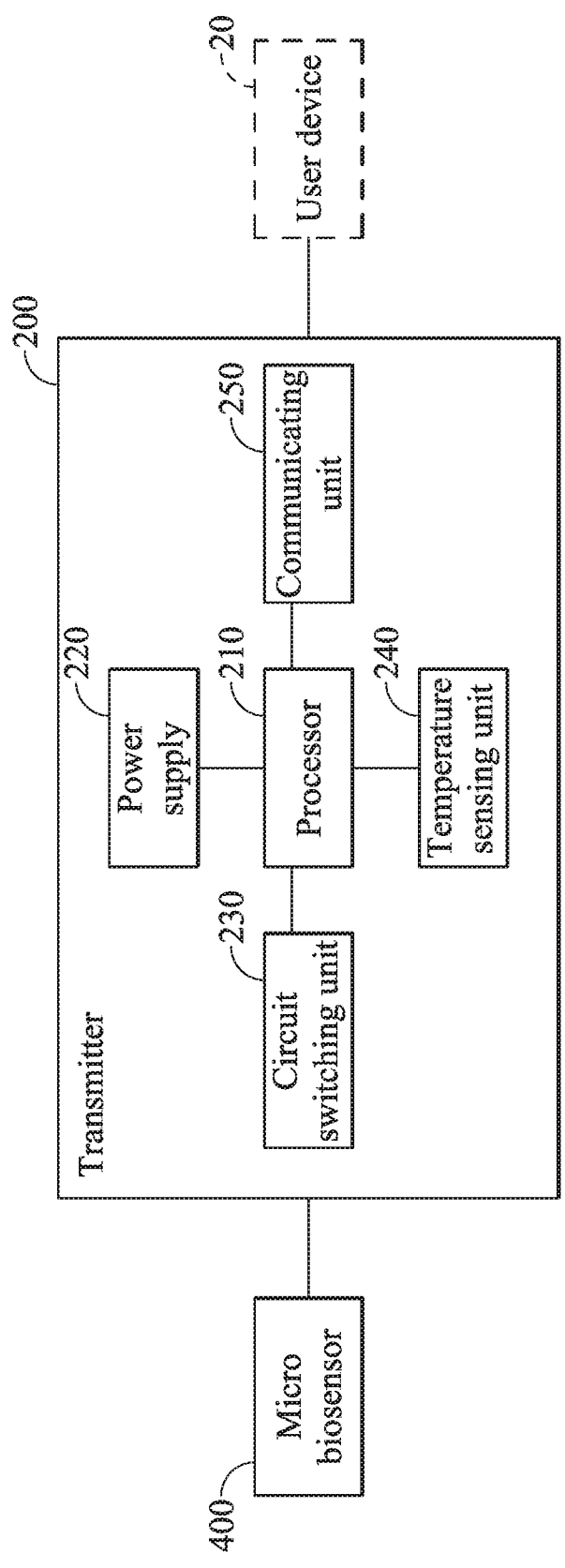
FIG. 17 shows a schematic diagram of a physiological signal measurement device of the present invention.

Please refer to FIG. 17, which is a schematic diagram of a physiological signal measurement device of the present invention. The physiological signal measurement device 10 of the present invention can be implanted subcutaneously to measure a physiological signal representing a physiological parameter associated with an analyte in a biofluid. The physiological signal measurement device 10 of the present invention includes a micro biosensor 400 and a transmitter 200, wherein the transmitter 200 is electrically connected to the micro biosensor 400 and includes a processor 210, a power supply 220, a circuit switching unit 230, a temperature sensing unit 240 and a communicating unit 250. The power supply 220 provides a voltage to the micro biosensor 400 through the circuit switching unit 230 for measuring the physiological signal, the temperature sensing unit 240 measures the body temperature of the living body, thereby the temperature measuring signal and the measured physiological signal measured by the micro biosensor 100 are transmitted to the processor 210, and the processor 210 operates the measured physiological signal to a physiological parameter. The communicating unit 250 can communicate with a user device by a wire or wireless transmission.

Figure 18A:
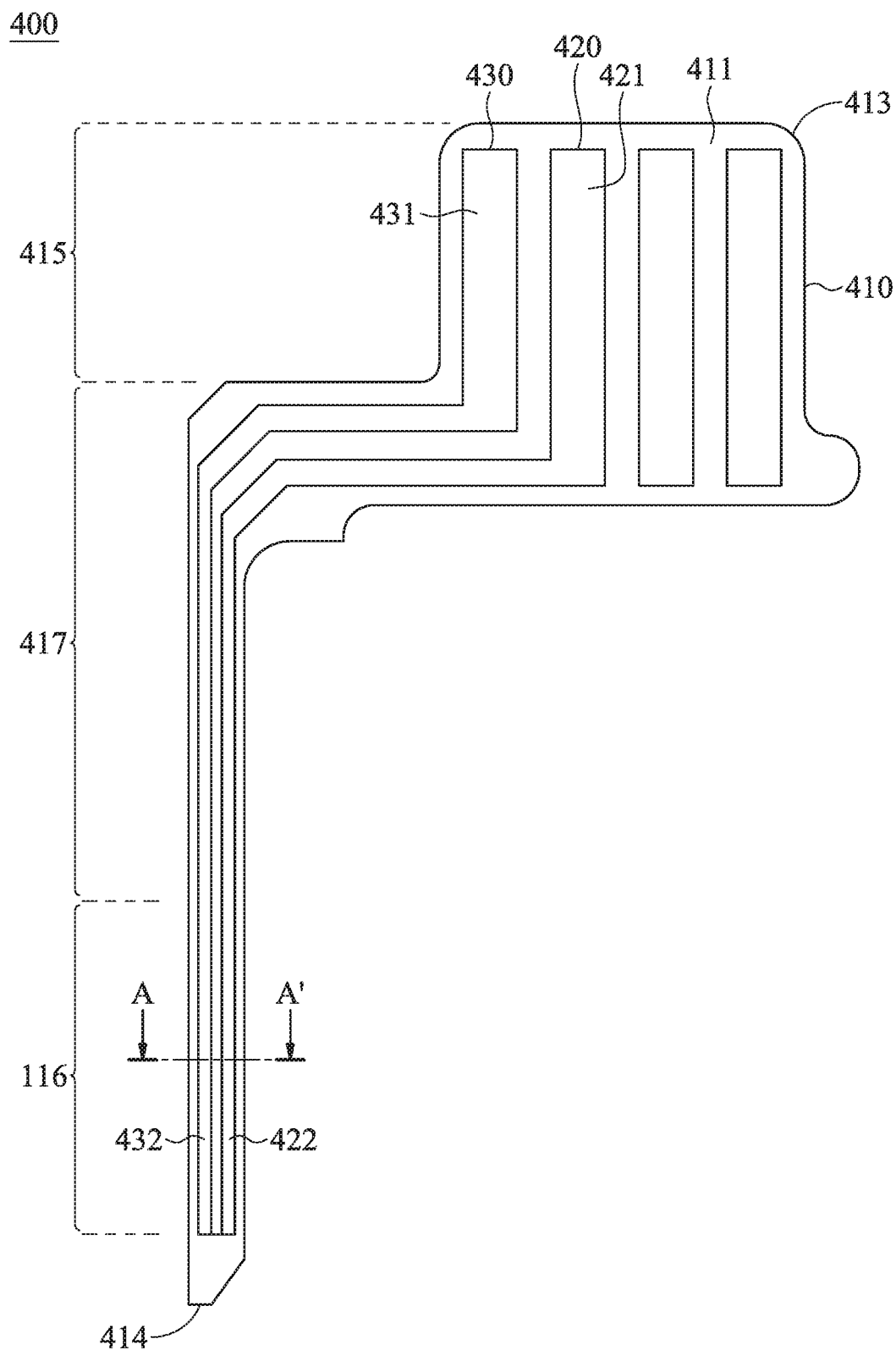
FIG. 18A shows a front schematic diagram of a first embodiment of a micro biosensor of the present invention.
Figure 18B:
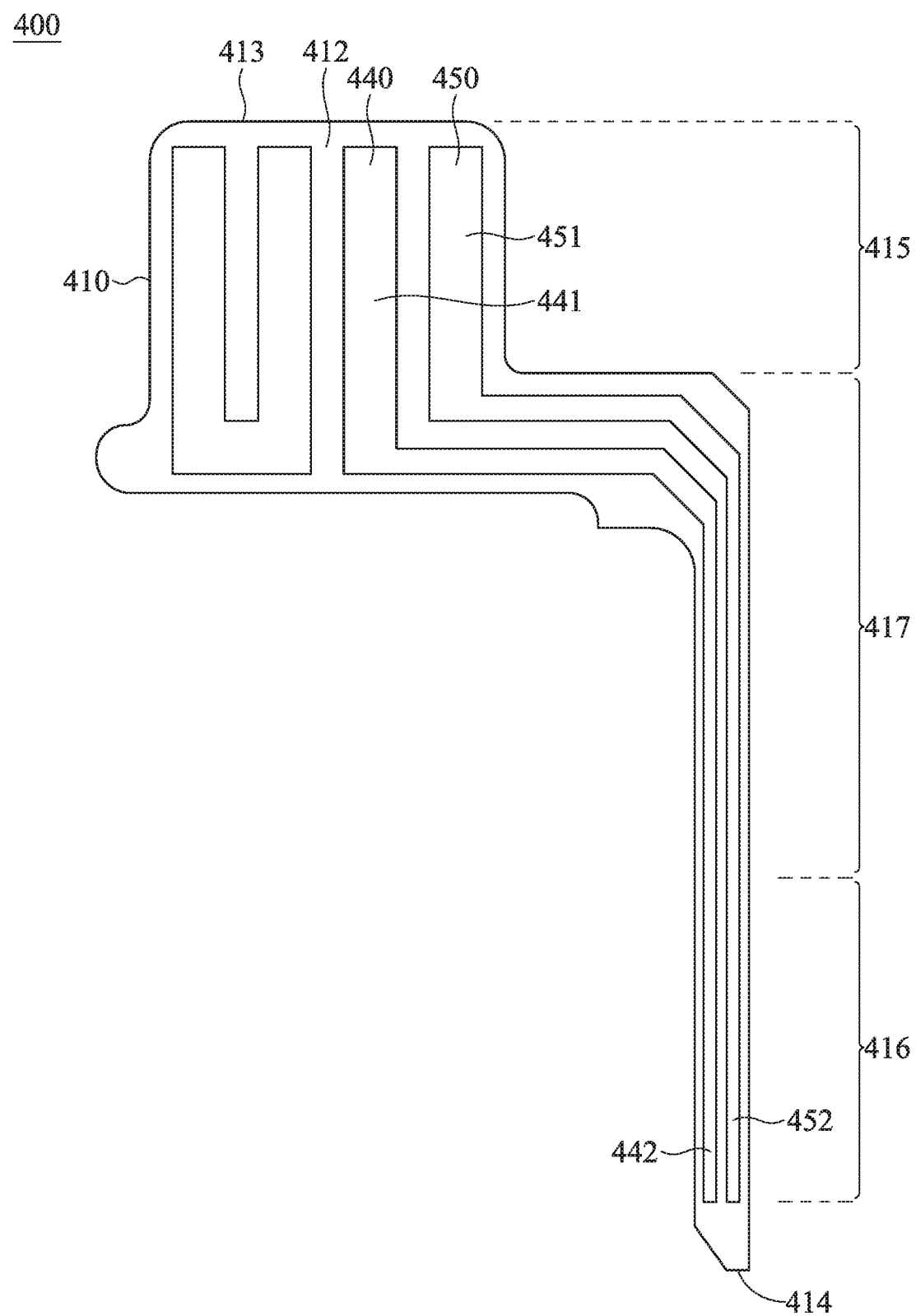
FIG. 18B shows a back schematic diagram of the first embodiment the micro biosensor of the present invention.
Figure 18C:
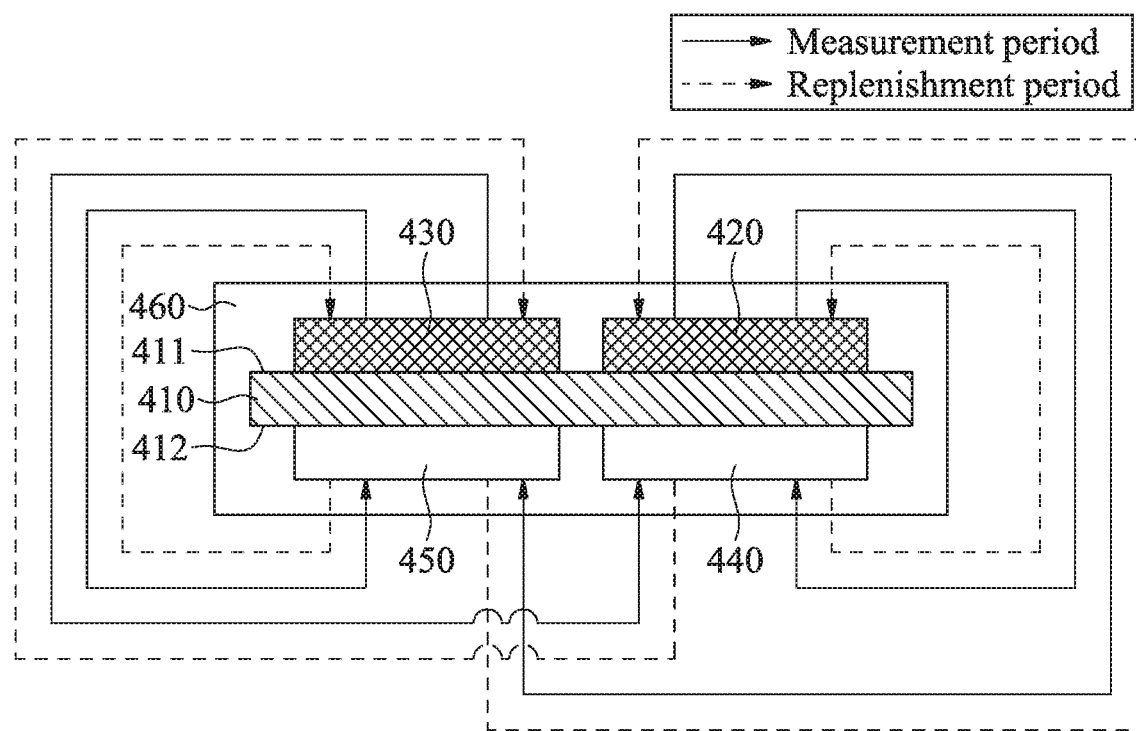
FIG. 18C shows a sectional schematic diagram of a cut view of the micro biosensor along the section line A-A' in FIG. 2A.

Please refer to FIGS. 18A and 18B, which are front and back schematic diagrams of a first embodiment of the micro biosensor of the present invention. The micro biosensor 400 of the present invention includes a substrate 410, a first working electrode 420, a second working electrode 430, a first counter electrode 440 and a second counter electrode 450 disposed on the substrate 410, and a chemical reagent 460 (as shown in FIG. 18C) covering the first working electrode 420, the second working electrode 430, the first counter electrode 440 and the second counter electrode 450. The material of the substrate 410 can be any material that is known to be suitable for use in electrode substrates and preferably has flexibility and insulation properties, such as but not limited to: polymer materials such as polyester and polyimide. The aforementioned polymer materials can be used alone or in combination. The substrate 410 includes a surface 411 (i.e. a first surface), an opposite surface 412 (i.e. a second surface) opposite to the surface 411, a first end 413 and a second end 414. The substrate 110 is separated into three areas respectively—they are a signal output area 415 located close to the first end 413, a sensing area 416 located close to the second end 414, and a connecting area 417 located between the signal output area 415 and the sensing area 416. The first working electrode 420 and the second working electrode 430 are disposed on the surface 411 of the substrate 410 and extended from the first end 413 to the second end 414 of the substrate 410. The first working electrode 420 includes a first signal output section 421 located in the signal output area 415 of the substrate 410, and a first signal sensing section 422 located in the sensing area 416 of the substrate 410. The second working electrode 430 includes a second signal output section 431 located in the signal output area 415 of the substrate 410, and a second signal sensing section 432 located in the sensing area 416 of the substrate 410.

The first counter electrode 440 and the second counter electrode 450 are disposed on the opposite surface 412 of the substrate 410 and extended from the first end 413 to the second end 414 of the substrate 410. The first counter electrode 440 includes a third signal output section 441 located in the signal output area 415 of the substrate 410, and a third signal sensing section 442 located in the sensing area 416 of the substrate 410. The second counter electrode 450 includes a fourth signal output section 451 located in the signal output area 415 of the substrate 410, and a fourth signal sensing section 452 located in the sensing area 416 of the substrate 410. The materials of the surfaces of the first counter electrode 440 and the second counter electrode 450 include silver and silver halide, preferably silver chloride or silver iodine. Because the electrode materials of the first counter electrode 440 and the second counter electrode 450 of the present invention include silver and silver halide (Ag/AgX), the first counter electrode 440 and the second counter electrode 450 of the present invention include functions of the counter electrode and the reference electrode of the common knowledge in the art. Specifically, the first counter electrode 440 and the second counter electrode 450 of the present invention can (1) form an electronic circuit with the first working electrode 420 or the second working electrode 430 to cause the current between the first counter electrode 440 or the second counter electrode 450 and the first working electrode 420 or the second working electrode 430 to be conducted to ensure that the oxidation reaction occurs on the first working electrode 420 or the second working electrode 430; and (2) provide a stable relative potential as a reference potential. Therefore, the first working electrode 420 or the second working electrode 430 and the first counter electrode 440 or the second counter electrode 450 of the present invention form a 4-electrode system. In order to further reduce the cost and improve the biocompatibility of the biosensor of the present invention, the Ag/AgX can be used with carbon, for example, the Ag/AgX is mixed into carbon paste, and the content of the silver halide can be an amount that allows the first counter electrode 440 and the second counter electrode 450 to stably perform the measurement step. The surface of the first counter electrode 440 and the second counter electrode 450 can be partially covered by a conductive material to prevent silver halide from the dissolution and to protect the first counter electrode 440 and the second counter electrode 450, wherein the conductive material is selected from the material that does not affect the measuring result of the working electrode. For example, the conductive material is carbon.

In another embodiment, the biosensor is not limited to a wire-type or stacked-type electrode structure.

According to another embodiment of the present disclosure, the initial amount of the silver halide can be zero before the biosensor is ready for shipping out of the plant for sale. In this case the first counter electrode 440 and/or the second counter electrode 450 of the biosensor has no silver halide. After the biosensor is subcutaneously implanted in the patient and during the first replenishment period before the first measurement, the initial amount of the silver halide can be replenished by oxidizing the silver coated on the first counter electrodes 440 and/or the second counter electrodes 450.

The chemical reagent 460 at least covers the first signal sensing section 422 of the first working electrode 420. In another embodiment, the chemical reagent 460 at least covers the first signal sensing section 422 of the first working electrode 420 and the second signal sensing section 432 of the second working electrode 430. In another embodiment, the chemical reagent 460 covers the signal sensing sections 422, 432, 442, 452 of all electrodes. In another embodiment, the first counter electrode 440 and/or the second counter electrode 450 are/is not covered by the chemical reagent 460. The sensing area 416 of the micro biosensor 400 can be implanted subcutaneously to cause the first signal sensing section 322 and the second signal sensing section 432 to measure the physiological signal of the analyte in the biofluid. The physiological signal is transmitted to the processor 210 through the first signal output section 421 and the second signal output section 431 to obtain the physiological parameter. In addition, apart from the transmitter 200, the physiological parameter can also be obtained from the user device 20 through the wire/wireless communication. The common user device 20 can be a smartphone, a physiological signal receiver or a blood glucose meter.

Please refer to FIG. 18C, which is a sectional schematic diagram of a cut view of the micro biosensor along the section line A-A' in FIG. 18A, wherein the line A-A' is a section line of the sensing area 416 of the micro biosensor 400. In FIG. 18C, the first working electrode 420 and the second working electrode 430 is disposed on the surface 411 of the substrate 410, the first counter electrode 440 and the second counter electrode 450 are disposed on the opposite surface 412 of the substrate 410, and the surfaces of the first working electrode 420, the second working electrode 430, the first counter electrode 440 and the second counter electrode 450 are covered by the chemical reagent 460. Basically, the chemical reagent 460 at least covers partial surface of one working electrode. The micro biosensor 400 of the present invention performs a measurement step during a measurement period, and performs a replenishment step during a replenishment period. One of the first working electrode 420 and the second working electrode 430 can be selected to measure the physiological signal in the measurement step, and the first working electrode 420 or the second working electrode 430 forms the electronic circuit with the first counter electrode 440 or the second counter electrode 450 to replenish silver halide to the first counter electrode 440 or the second counter electrode 450 in the replenishment step. Therefore, in this embodiment, when the measurement step is performed, a voltage level of the first working electrode 420 or the second working electrode 430 is higher than that of the first counter electrode 440 or the second counter electrode 450, causing a current to flow from the first working electrode 420 or the second working electrode 430 to the first counter electrode 440 or the second counter electrode 450, so that an oxidation reaction occurs on the first working electrode 420 or the second working electrode 430 having an electrochemical reaction with the chemical reagent 460 and the analyte and the physiological signal is measured, and a reduction reaction occurs on the first counter electrode 440 or the second counter electrode 450, so that silver halide (AgX) in the first counter electrode 440 or the second counter electrode 450 is consumed and dissociated into silver (Ag) and halide ion ($X^-$). Because the silver halide in the first counter electrode 440 or the second counter electrode 450 is consumed, the silver halide needs to be replenished in the first counter electrode 440 or the second counter electrode 450 to perform the next measurement step. When the replenishment step is performed, the voltage level of the first counter electrode 440 or the second counter electrode 450 is higher than that of the first working electrode 420 or the second working electrode 430, causing a current to flow from the first counter electrode 440 or the second counter electrode 450 to the first working electrode 420 or the second working electrode 430, so that an oxidation reaction occurs on the first counter electrode 440 or the second counter electrode 450 to cause silver to combine with halide ion to replenish silver halide. The detailed measurement step and the detailed replenishment step are illustrated in FIG. 10.

Figure 19A:
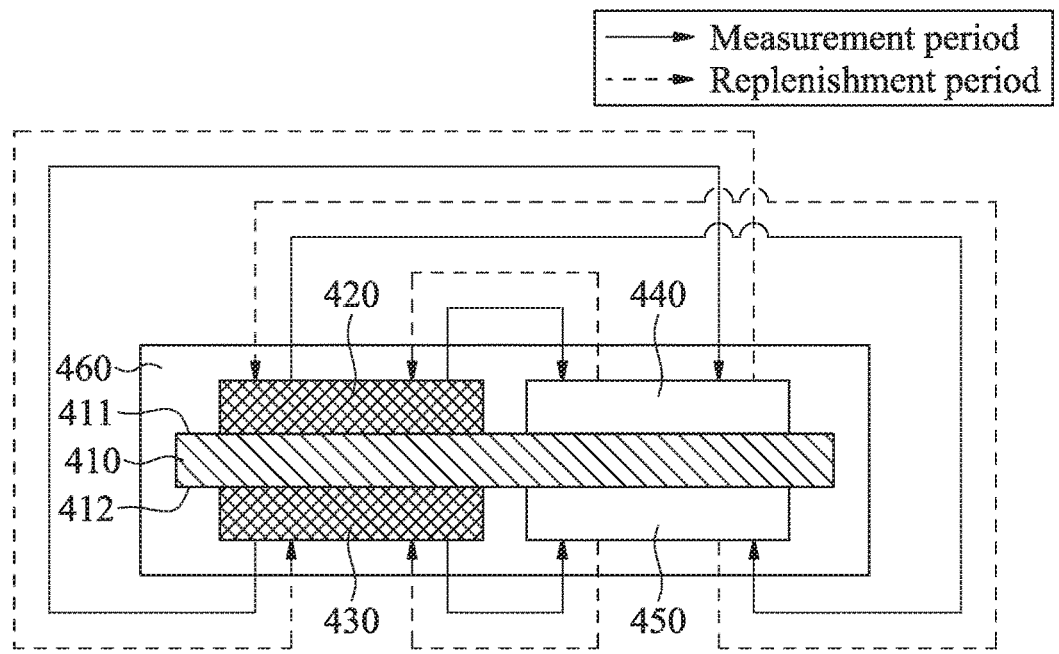
FIG. 19A shows a sectional schematic diagram of a second embodiment of the micro biosensor of the present invention.

Please refer to FIG. 19A, which is a sectional schematic diagram of a second embodiment of the micro biosensor of the present invention. The second embodiment is a variation of the electrode configuration of the first embodiment. In this embodiment, as shown in FIG. 19A, the first working electrode 420 and the first counter electrode 440 of the micro biosensor 400 of the present are disposed on the surface 411 of the substrate 410, the second working electrode 430 and the second counter electrode 450 are disposed on the opposite surface 412 of the substrate 410, and the surfaces of the first working electrode 420, the second working electrode 430, the first counter electrode 440 and the second counter electrode 450 are covered by the chemical reagent 460. Similarly, one of the first working electrode 420 and the second working electrode 430 can be selected to measure the physiological signal in the measurement step, and the first working electrode 420 or the second working electrode 430 forms the electronic circuit with the first counter electrode 440 or the second counter electrode 450 to replenish silver halide to the first counter electrode 440 or the second counter electrode 450 in the replenishment step. Therefore, in this embodiment, when the measurement step is performed, a current flows from the first working electrode 420 or the second working electrode 430 to the first counter electrode 440 or the second counter electrode 450, so that an oxidation reaction occurs on the first working electrode 420 or the second working electrode 430 and the physiological signal is measured, and a reduction reaction occurs on the first counter electrode 440 or the second counter electrode 450, so that silver halide (AgX) in the first counter electrode 440 or the second counter electrode is consumed and dissociated into silver (Ag) and halide ion ($X^-$). When the replenishment step is performed, a current flows from the first counter electrode 440 or the second counter electrode 450 to the first working electrode 420 or the second working electrode 430, so that an oxidation reaction occurs on the first counter electrode 440 or the second counter electrode 450 to cause the combination of silver and halide ion to replenish silver halide.

Figure 19B:
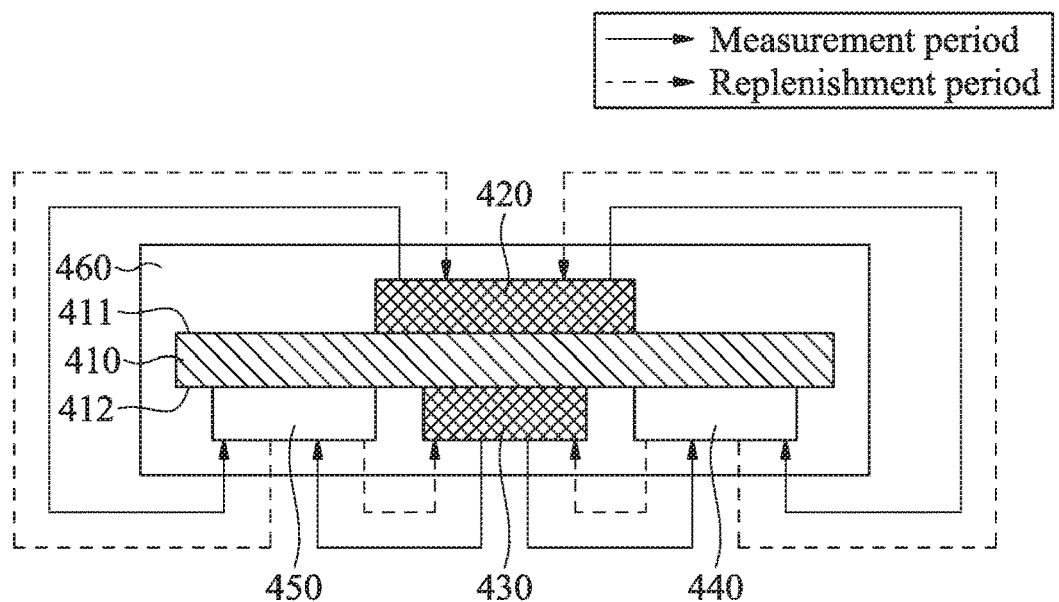
FIG. 19B shows a sectional schematic diagram of a third embodiment of the micro biosensor of the present invention.

Please refer to FIG. 19B, which is sectional schematic diagram of a third embodiment of the micro biosensor of the present invention. In the third embodiment, the first working electrode 420 of the micro biosensor 400 of the present is disposed on the surface 411 of the substrate 410, the second working electrode 430, the first counter electrode 440 and the second counter electrode 450 are disposed on the opposite surface 412 of the substrate 410, and the surfaces of the first working electrode 420, the second working electrode 430, the first counter electrode 440 and the second counter electrode 450 are covered by the chemical reagent 460. The second working electrode 430 can be disposed between two counter electrodes on the opposite surface 412, or disposed on the leftmost side or the rightmost side of the opposite surface 412 (figure not shown). In this embodiment, one of the first working electrode 420 and the second working electrode 430 can be selected to measure the physiological signal in the measurement step, and the first working electrode 420 or the second working electrode 430 forms the electronic circuit with the first counter electrode 440 or the second counter electrode 450 to replenish silver halide to the first counter electrode 440 or the second counter electrode 450 in the replenishment step.

Figure 19C:
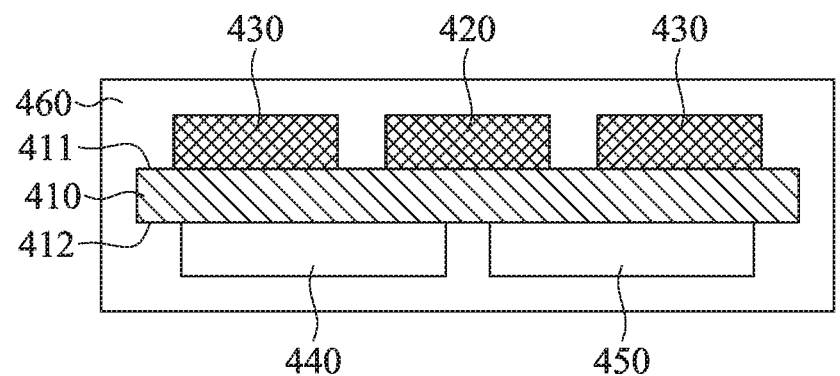
FIG. 19C shows a sectional schematic diagram of a fourth embodiment of the micro biosensor of the present invention.

Please refer to FIG. 19C, which is a sectional schematic diagram of a fourth embodiment of the micro biosensor of the present invention. In the fourth embodiment, the first working electrode 420 and the second working electrode 430 of the micro biosensor 400 of the present are disposed on the surface 411 of the substrate 410, wherein the second working electrode 430 is a U shape electrode adjacent to and around the sides of the first working electrode 420, the first counter electrode 440 and the second counter electrode 450 are disposed on the opposite surface 412 of the substrate 410, and the surfaces of the first working electrode 420, the second working electrode 430, the first counter electrode 440 and the second counter electrode 450 are covered by the chemical reagent 460. In this embodiment, one of the first working electrode 420 and the second working electrode 430 can be selected to measure the physiological signal in the measurement step, and the first working electrode 420 or the second working electrode 430 forms the electronic circuit with the first counter electrode 440 or the second counter electrode 450 to replenish silver halide to the first counter electrode 440 or the second counter electrode 450 in the replenishment step.

The detailed electrode stacks in FIGS. 18C-19C are omitted, and only the electrode positions are shown. Basically, the chemical reagent 460 in FIGS. 18C-19C at least covers partial surface of the first working electrode 420.

Materials of the first working electrode 420 and the second working electrode 430 include but are not limited to: carbon, platinum, aluminum, gallium, gold, indium, iridium, iron, lead, magnesium, nickel, manganese, molybdenum, osmium, palladium, rhodium, silver, tin, titanium, zinc, silicon, zirconium, a mixture thereof, or derivatives thereof (such as alloys, oxides or metal compounds, etc.). Preferably, the materials of the first working electrode 420 and the second working electrode 430 are a precious metal, a precious metal derivative or a combination thereof. More preferably, the first working electrode 420 and the second working electrode 430 are made of platinum-containing material. In another embodiment, the electrode material of the second working electrode 430 can be a material having a lower sensitivity to hydrogen peroxide than that of the first working electrode 420, such as carbon.

In any embodiment above, to prevent the silver electrode material from breakage due to over chlorination, a layer of conductive material, such as carbon, can be further disposed between the opposite surface 412 of the substrate 410 and the silver of the first counter electrode 440 and the second counter electrode 450. However, if the bottom layers of the first counter electrode 440 and the second counter electrode 450 are carbon, the resistance at a switch position will be too high. Conductive layers, such as silver, can be further disposed between the carbon conductive material and the opposite surface 412 of the substrate 410 for the first counter electrode 440 and the second counter electrode 450. Therefore, the material of the first counter electrode 440 and the second counter electrode 450 of the present invention sequentially are the conductive layer, the carbon layer and the silver/silver halide layer from the opposite surface 412 of the substrate 410.

Because there are two working electrodes and two counter electrodes in the micro biosensor 400 of the present invention, the measurement step is performed by such as the first working electrode 420 and the first counter electrode 440 while the replenishment step is performed by such as the second working electrode 430 and the second counter electrode 450, or the measurement step is performed by the first working electrode 420 while the replenishment step is performed by such as the second working electrode 430 and the second counter electrode 450 with the assistance of the second working electrode 430.

Switching Applications of a Constant Voltage Circuit

Figure 20A:
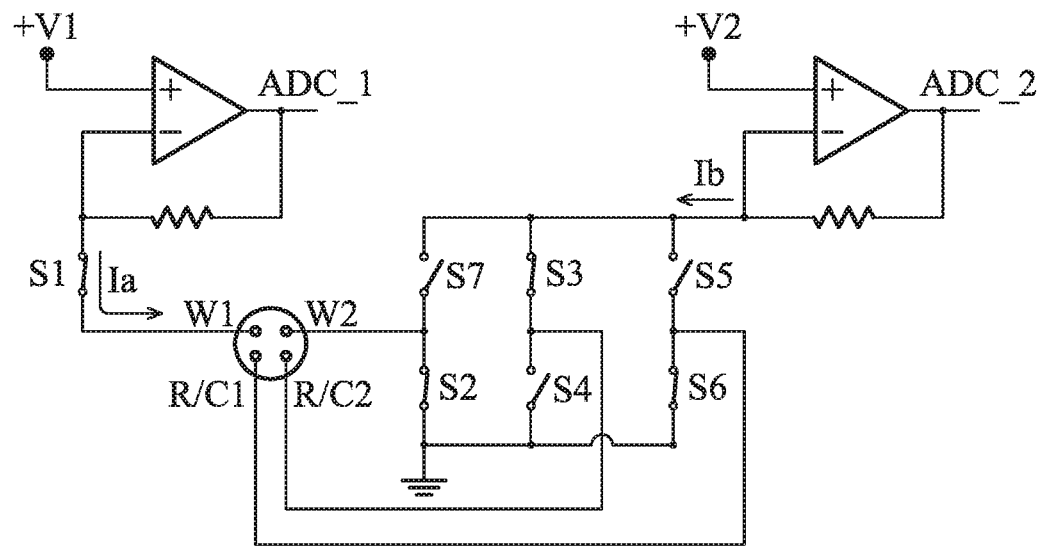
FIG. 20A shows a constant voltage circuit in the present invention that can perform a measurement mode and a replenishment mode according to a first manner.
Figure 20B:
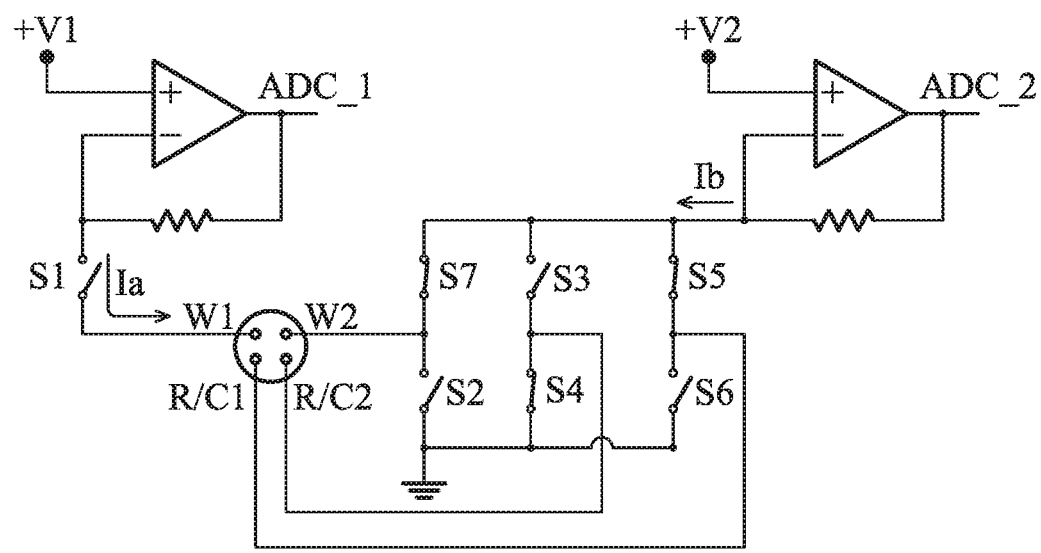
FIG. 20B shows a constant voltage circuit in the present invention that can perform a measurement mode and a replenishment mode according to a second manner.
Figure 20C:
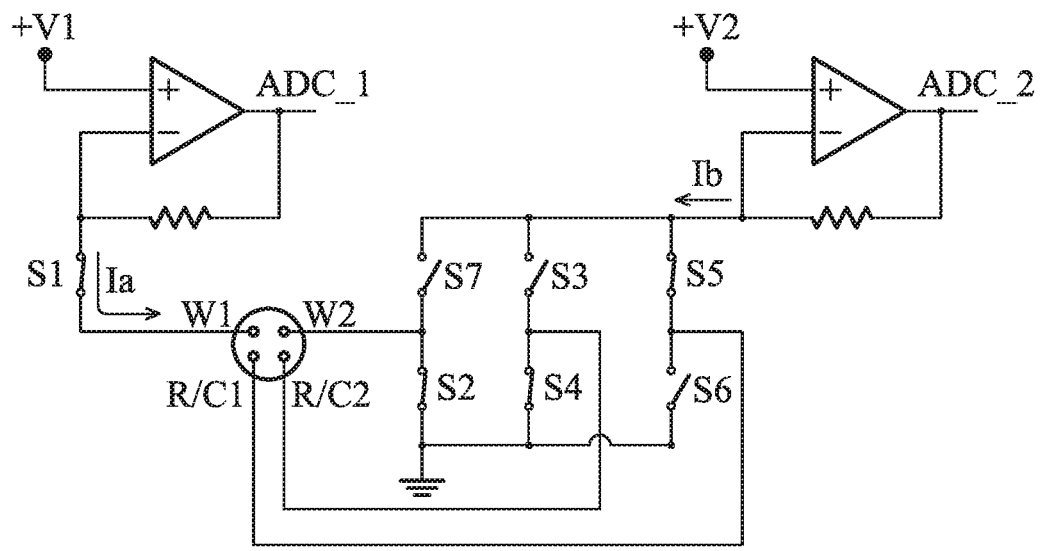
FIG. 20C shows a constant voltage circuit in the present invention that can perform a measurement mode and a replenishment mode according to a third manner.

Please refer to FIGS. 20A-20C, which show a constant voltage circuit in the present invention that can perform a measurement mode and a replenishment mode according to different manners. The measurement mode can be started and stopped by applying a measurement potential difference V1 and removing the measurement potential difference V1, respectively, and the corresponding current is represented by Ia. In the constant voltage circuit, the first working electrode W1 is controlled by the switch S1, the first counter electrode R/C1 is controlled by the switches S5 and S6, the second working electrode W2 is controlled by the switches S2 and S7, and the second counter electrode R/C2 is controlled by the switches S3 and S4. With the control of the above switches, there are multiple flexible operation manners.

As shown in FIG. 20A, in the measurement mode, the measurement potential difference V1 is applied across the first working electrode W1 and the first counter electrode R/C1 during the measurement period T1, so that the voltage of the first working electrode W1 is higher than that of the first counter electrode R/C1. During the measurement mode, the switches S1 and S6 are in the close circuit state, the switch S5 is in the open circuit state, the first working electrode W1 is +V1, and the first counter electrode R/C1 is grounded, so that at the first working electrode W1, an oxidation reaction occurs, and the first working electrode W1 electrochemically reacts with chemical reagents and an analyte to output a physiological signal Ia. The AgCl in the first counter electrode R/C1 has a consumption amount corresponding to the physiological signal Ia. The replenishment mode can be started and stopped by applying a replenishment potential difference V2 and removing the replenishment potential difference V2, respectively, and the corresponding current is represented by Ib. V2 is a constant value in a range of 0.1V to 0.8V, preferably range of 0.2V to 0.5V. In the replenishment mode, the replenishment potential difference V2 is applied across the second working electrode W2 and the second counter electrode R/C2 during the replenishment period t2, so that the voltage of the second counter electrode R/C2 is higher than that of the second working electrode W2. During the replenishment mode, the switches S4 and S7 are in the open circuit state, the switches S2 and S3 are in the close circuit state, the second counter electrode R/C2 is +V2 and the second working electrode W2 is grounded, so that on the second counter electrode R/C2, an oxidation reaction of Ag occurs to replenish the second counter electrode R/C2 with AgCl by a replenishment amount. In the constant voltage circuit, the replenishment potential difference V2 is a constant voltage, and the measured output current is Ib. In the present invention, the amount or value of capacity (with the unit "coulomb" and represented by the symbol "C") of AgCl is defined by calculating the area under the current curve, so the consumption amount of AgCl in the measurement mode is Ia*T1, and the replenishment amount of AgCl in the replenishment mode is Ib*t2. In such case, the replenishment amount of AgCl can be controlled by adjusting the period t2 during which the potential difference V2 is applied. In other words, on the premise that the AgCl on the first or second counter electrode R/C1 or R/C2 is kept within the safe storage range, the replenishment amount can be equal to or not equal to (including approximately similar, greater than or less than) consumption amount. FIG. 20A illustrates the overlap of the timing during which the measurement mode and the replenishment mode are performed simultaneously. The control of the above-mentioned switches can also result in other forms of circuits to have a variety of flexible operation modes. In some preferred embodiments, the timing of the measurement mode and timing of the replenishment mode can be the same timing, and can also partially overlap or not overlap.

FIG. 20B-20C are similar to FIG. 20A, and the mere differences are that FIG. 20B shows an embodiment in which W2 and R/C2 are used for measurement and simultaneously W1 and R/C1 are used for replenishment; and FIG. 20C shows an embodiment in which W1 and R/C2 are used for measurement and simultaneously W2 and R/C1 are used for replenishment. In some preferred embodiments, the constant voltage circuit alternately switches to FIG. 20A and FIG. 20B and repeats the cycles. In some preferred embodiments, the constant voltage circuit alternately switches to FIG. 20A and FIG. 204C and repeats the cycles. In the above manner, the first counter electrode R/C1 and the second counter electrode R/C2 can be consumed and replenished by turns, so that AgCl on the two counter electrodes can be kept within a safe storage range. In some preferred embodiments, the constant voltage circuit may have a third voltage source to control the replenishment potential difference V2 to be different from the measurement potential difference V1.

By controlling the application of the potential difference and the switching of the switches, the constant voltage circuit shown in FIGS. 20A-20C can also alternately perform the measurement mode and the replenishment mode. FIGS. 5A-5D respectively show the current schematic diagrams of the constant voltage circuit running in the measurement mode and the replenishment mode by turns in different ways. As shown in FIGS. 5A-5D, between any two of a plurality of measurement periods T1 is a period T2 during which no measurement is performed. In some preferred embodiments, T2 is a constant value. In FIGS. 5A-5D, the horizontal axis represents time, the curve for V1 represents the application and removal of the measurement potential difference V1, and the curve for V2 represents the application and removal of the replenishment potential difference V2. Please refer to FIG. 5A. In a preferred embodiment, both V2 and T2 are constant values, and the period t2 (i.e., the replenishment period) during which V2 is applied is a variable value. The replenishment period t2 is dynamically adjusted in a range of 0 to T2 according to the physiological signal Ia measured in the measurement mode and during the measurement period T1. As shown in FIG. 5A, t2 can be t2', t2'', or t2''' . . . . In other words, the replenishment period t2 can be changed according to the consumption amount of AgCl. In the condition of a high consumption amount of AgCl, the counter electrode R/C can be replenished for a longer time to keep the AgCl on the first counter electrode R/C1 within the safe storage range. For example, the amount of AgCl replenished during t2'' will be greater than the amount of AgCl replenished during t2'.

Please refer to FIG. 5B, in another preferred embodiment, V2, T2 and t2 are all constant values, wherein t2=T2. That is, the measurement mode and replenishment mode alternate seamlessly, and the period during which no measurement is performed is the replenishment period. Please refer to FIGS. 5C and 5D, in some preferred embodiments, V2, T2, and t2 are constant values, wherein t2 is a constant value greater than 0 and less than T2. For example, t2=½ T2, ⅖ T2, ⅗ T2, etc. The difference between FIG. 5C and FIG. 5D is that in FIG. 5C, after each measurement mode, a buffer time (buffer time=T2−t2) is passed before the replenishment mode starts; and in FIG. 5D, after each measurement mode, the replenishment mode starts immediately without any buffer time, and there is a period of time between the end of each replenishment mode and the start of the next measurement mode. In some preferred embodiments, t2 is less than T2, and t2 can be any time period during T2.

Please refer to FIGS. 5E and 5F, which show current-time schematic diagrams of the constant voltage circuit running in the measurement mode and the replenishment mode by turns in different ways. In FIGS. 5E and 5F, the horizontal axis represents time, and the curve represents the physiological parameter curve calculated from the measured physiological signal Ia. In the two embodiments, similar to that in FIG. 5A, V2 and T2 are constant values and the replenishment period t2 is a variable value. In FIGS. 5E and 5F, the white area under the curve represents the AgCl consumption amount in the measurement mode (Ia*Tl), and the oblique area represents the replenishment amount of AgCl in the replenishment mode (Ib*t2). It can be seen from the figures that in order to make Ib*t2 close to Ia*Tl or within a certain range of Ia*Tl, the replenishment period t2 is dynamically adjusted in a range of 0 to T2 according to the measured physiological signal Ia and the measurement period T1. According to requirements, the front part (as shown in FIG. 5E) or the back part (as shown in FIG. 5F) of the period (T2) where the measurement mode is not executed can be selected to perform the replenishment mode.

Switching Applications of a Segmental Constant Current Circuit.

Figure 21:
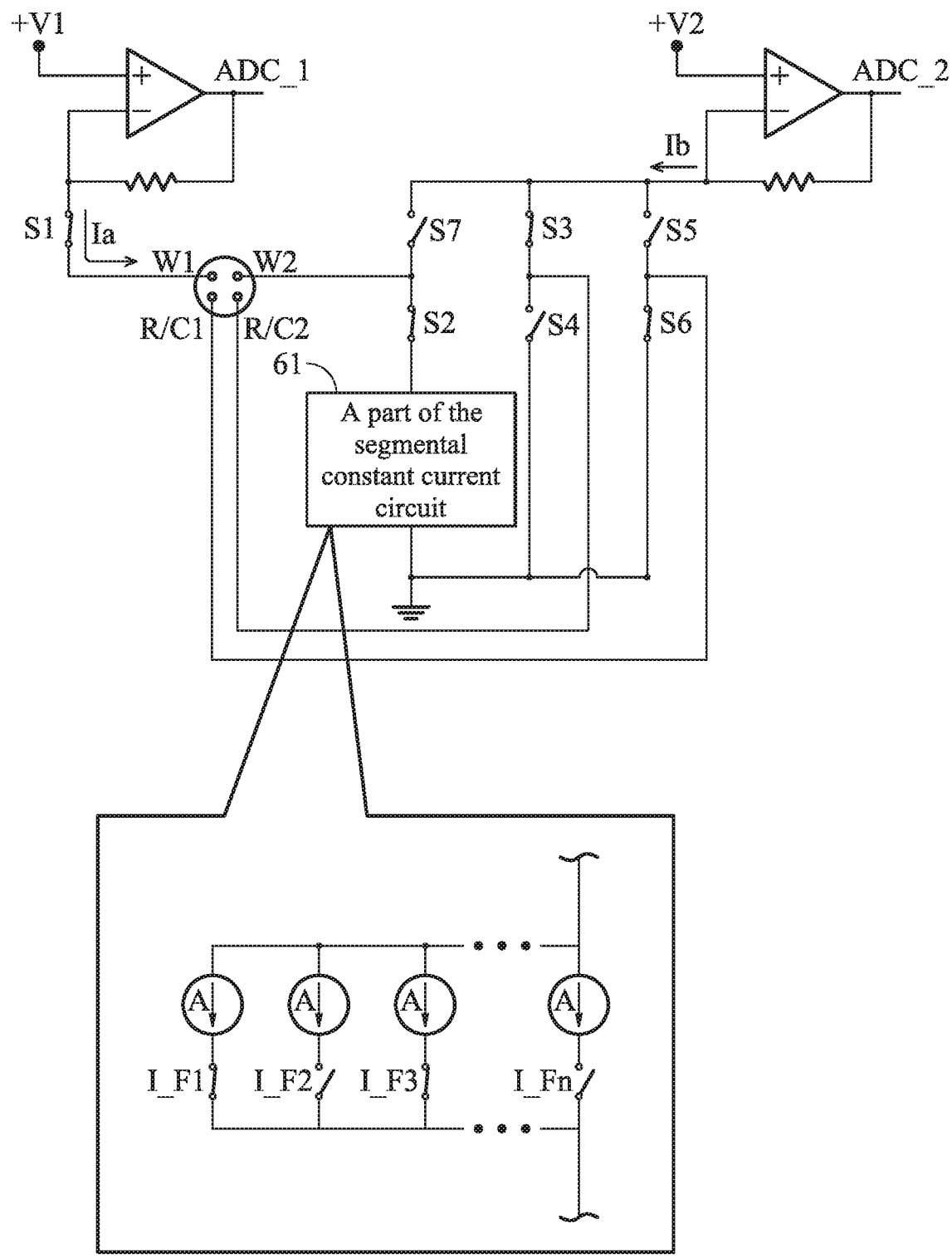
FIG. 21 shows a segmental constant current circuit in the present invention that can perform a measurement mode and a replenishment mode.

Please refer to FIG. 21, which shows a segmental constant current circuit of the present invention that can perform a measurement mode and a replenishment mode. The way by which the segmental constant current circuit repeats the measurement mode and the recharge mode is similar to that of FIG. 20A, so it will not be repeated here. The main difference is that the replenishment mode can be started and stopped by applying a replenishment potential difference V2, which is a variable value, and removing the replenishment potential difference V2, respectively, and the corresponding current is represented by Ib. Taking the embodiment where the replenishment mode is performed by using the second working electrode W2 and the second counter electrode R/C2 as an example, the replenishment potential difference V2 is applied across the second working electrode W2 and the second counter electrode R/C2 during the replenishment period t2. During the replenishment mode, the switches S2 and S3 are in the close circuit state, the switches S2 and at least one of switches corresponding to I_F1 to I_Fn in a part of the segmental constant current circuit 61 are in the close circuit state, the second working electrode W2 is grounded, and the second counter electrode R/C2 is +V2, so that on the second counter electrode R/C2, an oxidation reaction of Ag occurs to replenish the second counter electrode R/C2 with AgCl. The segmental constant current circuit in this embodiment can selectively switch to I_F1, I_F2, I_F3 ... I_Fn by controlling multiple switches corresponding to I_F1 to I_Fn to adjust the required replenishment potential difference V2 and output the current Ib. In the replenishment mode, according to the magnitude of the physiological signal Ia and the measurement period T1, the replenishment amount of AgCl can be controlled by adjusting the required replenishment potential difference V2 and the period t2 during which the potential difference V2 is applied. That is, on the premise that the AgCl on the first or second counter electrode R/C1 or R/C2 is kept within the safe storage range, the replenishment amount can be equal to or not equal to (including approximately similar, greater than or less than) the consumption amount. In another embodiment, the part of the constant current circuit 61 may be configured to be connected to the second counter electrode R/C2.

Switching Applications of a Continuous Variable Constant Current Circuit.

Figure 22:
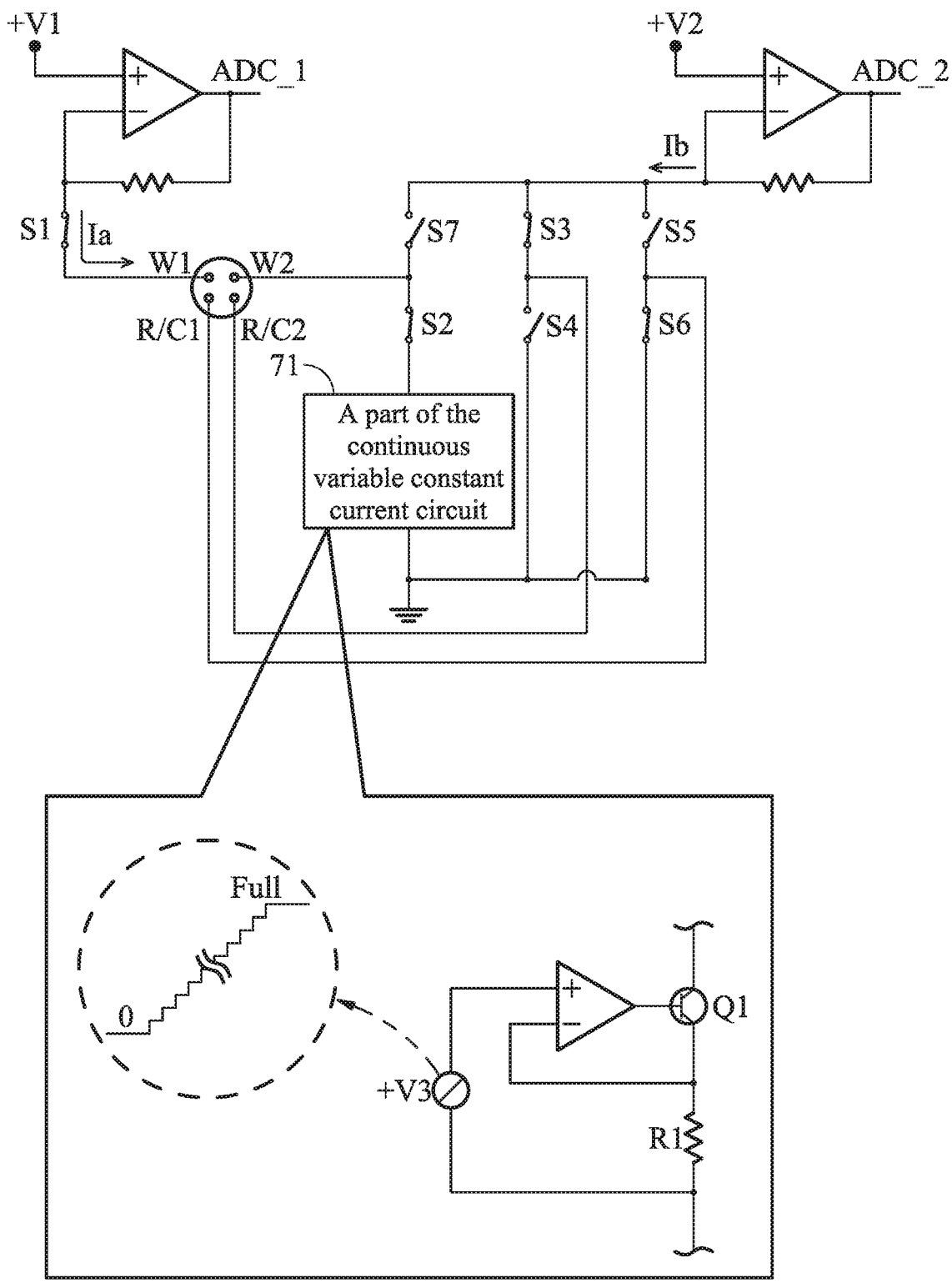
FIG. 22 shows a continuous variable constant current circuit in the present invention that can perform a measurement mode and a replenishment mode.

Please refer to FIG. 22, which shows a continuous variable constant current circuit of the present invention that can perform a measurement mode and a replenishment mode. The measurement mode of the continuous variable constant current circuit is similar to that in FIGS. 20A-20C and the replenishment mode thereof is similar to that in FIG. 21, so they will not be repeated here. The embodiment in FIG. 22 differs from that in FIG. 21 only in that a part of the continuous variable constant current circuit 71 in FIG. 22 output a constant current Ib through the control of a digital-to-analog converter (DAC).

Please refer to FIGS. 8A-8C, which respectively show voltage schematic diagrams of the constant current circuit running in the measurement mode and the replenishment mode by turns in different ways. In FIGS. 8A-8C, the horizontal axis represents time, the curve for V1 represents the application and removal of the measurement potential difference V1, and the curve for V2 represents the application and removal of the replenishment potential difference V2. Please refer to FIG. 8A, in a preferred embodiment, T2 is a constant value, V2 and the period t2 (i.e., the replenishment period) during which V2 is applied are variable values. The replenishment period t2 is dynamically adjusted in a range of 0 to T2 according to the measurement period T1 and the physiological signal Ia measured in the measurement mode. As shown in FIG. 8A, t2 can be t2', t2", or t2'" .... In other words, the replenishment period t2 can be changed according to the consumption amount of AgCl. In the condition of a high consumption amount of AgCl, the counter electrode R/C can be replenished for a longer time to keep the AgCl on the counter electrode R/C within the safe storage range.

Please refer to FIG. 8B, in another preferred embodiment, V2 is a variable value, and T2 and t2 are constant values, wherein t2 is a constant value greater than 0 and less than T2. For example, t2 can be ½ T2, ⅖ T2, ⅗ T2, etc. In this embodiment, V2 is dynamically adjusted according to the consumption amount of AgCl in the step of measuring the physiological signal (i.e., in the measurement mode). One example of the dynamic adjustment method is as follows. For example, the segmental constant current circuit is used. The circuit includes n constant current supplies and n switches, and each constant current supply corresponds to a switch. In the replenishment mode, according to the consumption amount of AgCl, at least one of the n switches is selected to be turned on (i.e., in the close circuit state) to output a constant current value. When the replenishment period t2 is a constant value, the replenishment amount of AgCl can be controlled by selecting different constant current outputs.

Please refer to FIG. 8C, in another preferred embodiment, V2 is a variable value, T2 and t2 are constant values, wherein t2=T2. That is, the measurement mode and replenishment mode alternate seamlessly, and the period during which no measurement is performed is the replenishment period.

Compared with the continuous variable constant current circuit, in the segmental constant current circuit, multiple current paths can be controlled through multiple switches, and thus the replenishment can be performed by segmental constant current according to the amount of current required. The segmental constant current, in this way, saves electricity and can reduce costs. In addition, whether it is a constant voltage circuit or a constant current circuit, the potential difference can come from a DC power supply or an AC power supply, preferably from a DC power supply.

The embodiments of FIGS. 5A-5F, 6A-6B, 7A-7B and 8A-8C all involve the operation manner of alternately cycling measurement step and replenishment step, which means that there is an AgCl replenishment step between any two measurement steps. Such manner can better ensure that AgCl remains within the safe storage range. However, in some preferred embodiments, Y times of AgCl replenishment can be optionally performed during N measurements, where Y≤N, in such a way that the accumulated replenishment amount of AgCl can still be kept within the safe storage range. The measurement step and the replenishment step do not necessarily need to be performed in an alternate cycle. A replenishment step can also be performed after several measurement steps, or after a predetermined measurement time. For example, a replenishment step can be performed after 10 measurement steps, or after the accumulated measurement time reaches 1 hour.

Please refer to FIG. 8D, which shows a current-time schematic diagram of the constant current circuit running in the measurement mode and the replenishment mode by turns in a way similar to that of FIG. 8C. In FIG. 8D, the curve represents the physiological parameter curve calculated from the measured physiological signal Ia, the conditions of T2 and t2 being both constant values and V2 being a variable value are similar to those in FIG. 8C. In FIG. 8D, the white area under the curve represents the AgCl consumption amount in the measurement mode (Ia*Tl), and the oblique area represents the replenishment amount of AgCl in the replenishment mode (Ib*t2). It can be seen from this figure that in order to make Ib*t2 close to Ia*Tl or within a certain range of Ia*Tl, the replenishment potential difference V2 is dynamically adjusted according to the consumption amount of AgCl.

In addition, although FIGS. 5E, 5F, and 8D do not show the output timing of each physiological parameter value after each measurement step for measuring a physiological signal is performed, the physiological parameter value may be output, but is not limited to, when the measurement is completed or during the replenishment period and the AgCl replenishment step may be performed after every physiological parameter is output or after obtaining the physiological signal, but is not limited thereto.

In the foregoing embodiments in which the constant currents or constant voltage circuits of the present invention alternately perform the measurement mode and the replenishment mode, the working electrode used in the measurement mode and the replenishment mode can be either the first working electrode W1 or the second working electrode W2, and the counter electrode used in the measurement mode can also be either the first counter electrode R/C1 or the second counter electrode R/C2. However, the counter electrode used in a replenishment mode is preferably the counter electrode used in the previous measurement mode just before the replenishment mode. Two exemplary embodiments are described below. Embodiment 1 performs the following steps in order: (a) measurement by using W1/W2 (representing one of W1 and W2) and R/C1, (b) replenishment by using the other one of W1 and W2 and R/C1, (c) measurement by using W1/W2 and R/C2, and (d) replenishment by using the other one of W1 and W2 and R/C2, and repeat the steps (a)-(d). Embodiment 2 repeats the steps (a), (b), (a), (b), (c), (d), (c) and (d) in order.

Figure 23A:
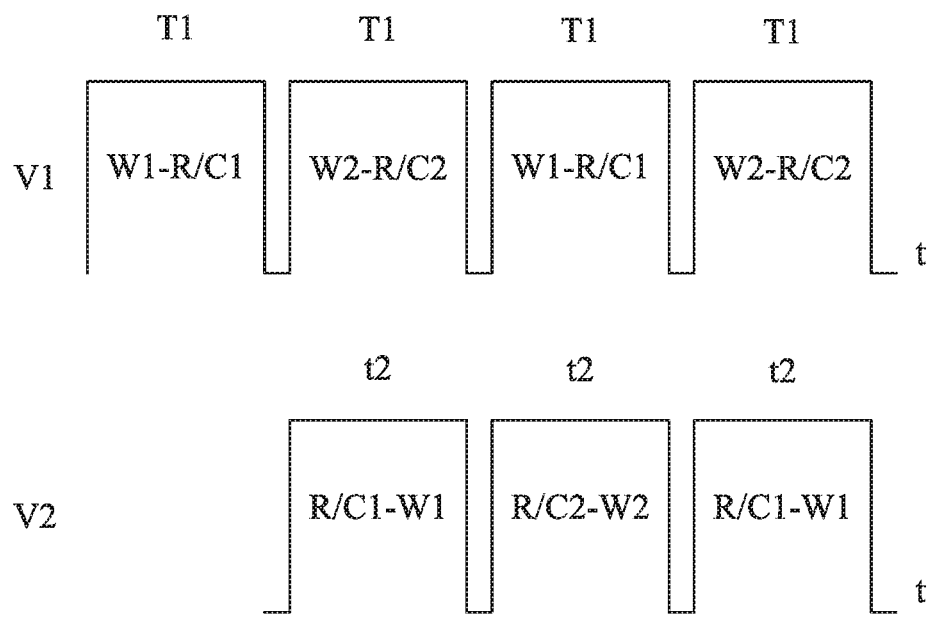
FIG. 23A shows a schematic diagram of the constant current or constant voltage circuit of the present invention performing the measurement mode and the replenishment mode according to an embodiment.
Figure 23B:
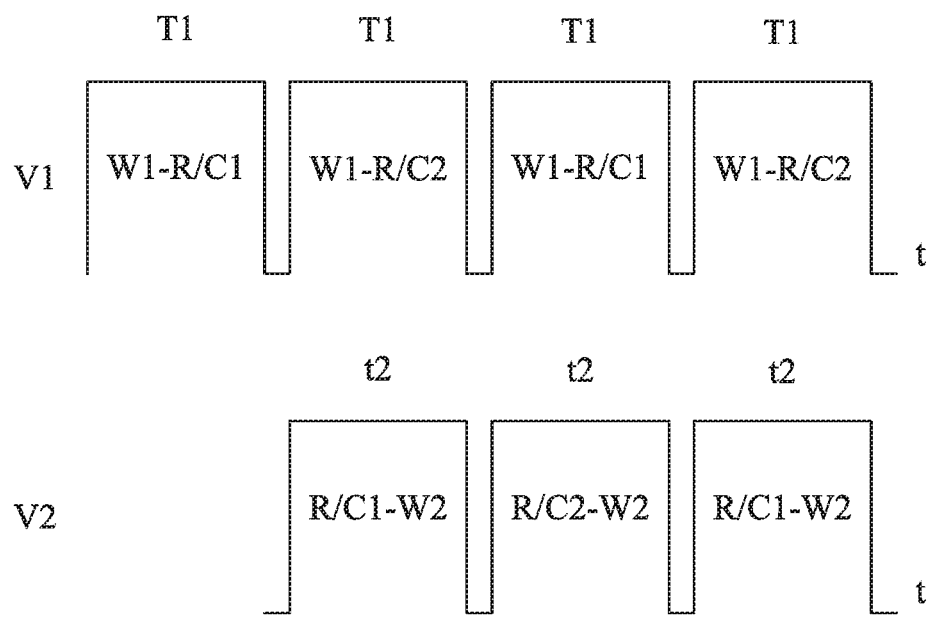
FIG. 23B shows a schematic diagram of the constant current or constant voltage circuit of the present invention performing the measurement mode and the replenishment mode according to another embodiment.

Please refer to FIGS. 23A and 23B, which show schematic diagrams of the constant current or constant voltage circuit of the present invention simultaneously performing the measurement mode and the replenishment mode according to different embodiments. In FIGS. 23A and 23B, the horizontal axis represents time, the curve for V1 represents the application and removal of the measurement potential difference V1, and the curve for V2 represents the application and removal of the replenishment potential difference V2. Because there are two counter electrodes and two working electrodes in the present invention, the measurement step and the replenishment step can be performed simultaneously. In the embodiment of FIG. 23A, a first combination consisting of the first working electrode W1 and the first counter electrode R/C1 and the second combination consisting of the second working electrode W2 and the second counter electrode R/C2 take turns to perform the measurement steps and the replenishment steps. That is, when the first combination is used for the measurement step, the second combination is used for the replenishment step, and vice versa. In the embodiment of FIG. 23B, the first working electrode W1 is fixed for the measurement steps, the second working electrode W2 is fixed for the replenishment steps, and the two counter electrodes are used by turn between the measurement step and the replenishment step. In some preferred embodiments, multiple T1s do not overlap each other. In some preferred embodiments, multiple t2s do not overlap each other. In some preferred embodiments, T1 and t2 overlap (meaning that they start simultaneously and end at the same time) or partially overlap. FIGS. 23A and 23B show that the first measurement (using R/C1) is not accompanied by a replenishment step, and the second measurement (using R/C2) is performed along with a replenishment step (replenishing R/C1). However, it is also possible to perform the replenishment step (replenishing R/C2) at the same time when the first measurement (using R/C1) is performed.

Please refer to FIG. 9, which shows a method of measuring an analyte according to the present invention. A usage lifetime of a micro biosensor can be prolonged by the method. The micro biosensor, which may be, for example, the micro biosensor shown in FIG. 18A-18C and FIGS. 19A-19C, is used to be implanted subcutaneously to measure a physiological signal representative of a physiological parameter associated with the analyte in a biofluid (such as tissue fluid). In the embodiment of FIG. 9, the analyte can be glucose in the tissue fluid, the physiological parameter is the glucose level or concentration in the human body, and the physiological signal is a current value measured by the micro-biological sensor. In this embodiment, the method for measuring the analyte includes repeatedly performing the measurement step (S901) and the replenishment step (S902). The measurement step (S901) includes using the aforementioned constant voltage circuit or the constant current circuit to perform the aforementioned measurement mode during the measurement period T1 to output a physiological signal (i.e., a current value), and at the same time, the AgCl on the counter electrode has a consumption amount corresponding to the current value. The measurement step (S901) also includes stopping the measurement step by stopping the measurement mode, and the current value is calculated to output a physiological parameter (i.e., glucose level).

In the measurement step (S901), the chemical equations are as follows.

The following oxidation reactions occur at the first working electrode 420 or the second working electrode 430.

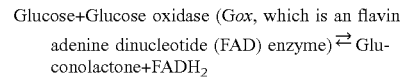

Glucose+Glucose oxidase (Gox, which is an flavin adenine dinucleotide (FAD) enzyme) $\rightleftarrows$ Gluconolactone+FADH$_2$

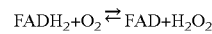

FADH$_2$+O$_2$ $\rightleftarrows$ FAD+H$_2$O$_2$

H$_2$O$_2$ $\rightleftarrows$ 2H$^+$+O$_2$+2e$^-$

The following reduction reactions occur at the first counter electrode 440 or the second counter electrode 450.

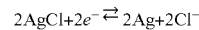

2AgCl+2e$^-$ $\rightleftarrows$ 2Ag+2Cl$^-$

The replenishment step (S902) includes using the aforementioned constant voltage circuit or constant current circuit to perform the aforementioned replenishment mode during the replenishment period, such that the AgCl on the counter electrode has a replenishment amount corresponding to consumption amount, and thus the AgCl on the counter electrode has an amount controlled within a safe storage range. As a result, the potential difference between the working electrode and the counter electrode can be kept stable, so that the obtained current value can still maintain a stable correlation with the glucose value (if the detected substance is other analytes, the correlation may be proportional or inverse correlation). In other words, it is possible to keep a stable correlation between a next current value obtained in a next measurement step and a next glucose value. The replenishment step (S902) also includes a step of stopping the replenishment step by stopping the aforementioned replenishment mode. After the replenishment step (S902) is finished, the method returns to the measurement step (S901) until N measurement steps (S901) and N replenishment steps (S902) are executed. In some preferred embodiments, the measurement step (S901) and the replenishment step (S902) are performed simultaneously, not simultaneously, or partially overlapping. In some preferred embodiments, N measurement steps do not overlap each other. In some preferred embodiments, N replenishment steps do not overlap each other.

In the replenishment step (S902), the chemical equations are as follows. The following reduction reactions occur at the first working electrode 420 or the second working electrode 430.

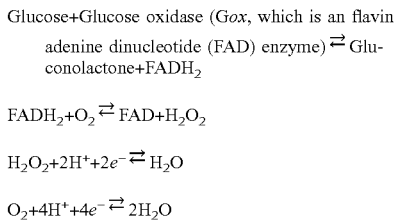

Glucose+Glucose oxidase (Gox, which is an flavin adenine dinucleotide (FAD) enzyme) $\rightleftarrows$ Gluconolactone+FADH$_2$ FADH$_2$+O$_2$ $\rightleftarrows$ FAD+H$_2$O$_2$ H$_2$O$_2$+2H$^+$+2$e^-$ $\rightleftarrows$ H$_2$O O$_2$+4H$^+$+4$e^-$ $\rightleftarrows$ 2H$_2$O The positive potential on the first counter electrode 440 or the second counter electrode 450 cause the following oxidation reactions occurring at the first counter electrode 440 or the second counter electrode 450.

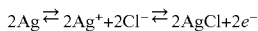

2Ag $\rightleftarrows$ 2Ag$^+$+2Cl$^-$ $\rightleftarrows$ 2AgCl+2$e^-$

The Ag on the counter electrode is oxidized to Ag$^+$ and combined with Cl$^-$ from the body or from oxidation (or dissociation) of AgCl to form AgCl, such that part or all of the AgCl consumed during the measurement period T1 is replenished onto the counter electrode.

Human can intake chloride ions and iodide ions through iodine-doped salts. The available halide ions include at least chloride ions and iodide ions for replenishing the counter electrode with silver halide.

The following embodiments are directed to cycles of N measurement steps (S901) and N replenishment steps (S902). The physiological parameter mentioned is preferably a glucose value, and the physiological signal mentioned is preferably a current value. According to some preferred embodiments, each measurement potential difference V1 is applied during the measurement period T1, each replenishment potential difference V2 is applied during the replenishment period t2, and the measurement period T1 is a constant value, which can be a value within 3 seconds, 5 seconds, 10 seconds, 15 seconds, 30 seconds, 1 minute, 2.5 minutes, 5 minutes, 10 minutes, or 10 minutes, and preferably within 30 seconds. The measurement period T1 is a constant value, and can be 2.5 seconds, 5 seconds, 15 seconds, 30 seconds, 1 minute, 2.5 minutes, 5 minutes, 10 minutes, or 30 minutes, preferably 30 seconds. According to some preferred embodiments, each measurement period T1 plus each replenishment period t2 is a constant value. According to some preferred embodiments, each replenishment potential difference V2 has a constant voltage value, and each replenishment period t2 is dynamically adjusted according to each consumption amount of AgCl (as shown in FIG. 5A). According to some preferred embodiments, each output physiological parameter is obtained through calculation of the physiological signals at a single measurement time point in each measurement period T1. According to some preferred embodiments, each output physiological parameter is obtained through a mathematical operation value of a plurality of physiological signals at a plurality of measurement time points in each measurement period T1. The aforementioned mathematical operation value is, for example, a accumulated value, an average value, a median value, an average value of median, and so on. According to some preferred embodiments, the replenishment amount of AgCl on the counter electrode is controlled within a safe storage range by controlling each replenishment amount to be equal to or not equal to (including approximately similar, greater than or less than) each consumption amount. As a result, a next physiological signal obtained during a next measurement step maintains a stable proportional correlation with a next physiological parameter. According to some preferred embodiments, the step of removing each measurement potential difference V1 is to disconnect the circuit that connects the working electrode and the counter electrode, or set each measurement potential difference V1 to zero. In other words, the power can be turned off to make the measurement circuit have an open circuit state; or, a 0 volt voltage can be applied across the working electrode and the counter electrode, wherein the operation time of either of the two operations is 0.01~0.5 seconds. The step of removing the measurement potential difference V1 can avoid the generation of A-shaped physiological signals. According to some preferred embodiments, the step of removing each replenishment potential difference V2 is to disconnect the circuit configured to connect the working electrode and the counter electrode, or set each replenishment potential difference V2 to zero.

According to some preferred embodiments, after the biosensor is implanted in the human body, a warm-up time is required for the biosensor to be in the condition of equilibrium and stability in the body in order to stably present a physiological signal that is positively correlated with an analyte concentration. Therefore, in the measurement step (S901), the measurement voltage is continuously applied until the end of the measurement period T1, and the measurement period T1 is controlled such that the physiological signal and the physiological parameter of the analyte have a stable proportional correlation. To this end, the measurement period T1 can be a variable value or a combination of a variable value and a constant value (for example, a variable value plus a constant value, in which the variable value may be 1 hour, 2 hours, 3 hours, 6 hours, 12 hours or 24 hours, and the constant value may be, for example, 30 seconds).

Please refer to FIGS. 5A-5F, 8A-8D and 9. The present invention uses a voltage applied to the counter electrode R/C during a period to measure a resultant current of the counter electrode, and the initial capacity of AgCl is obtained by mathematical calculation of the resultant current during the period. For example, the initial capacity of AgCl is defined by calculating area under a curve of the resultant current. The initial capacity of AgCl is also referred to as the initial amount or initial coulomb amount ($C_{initial}$), the following are all described by amount. The counter electrode R/C contains Ag and AgCl. When the amount of AgCl (X % AgCl) is known, the amount of Ag can be calculated (Y % Ag=100%−X % AgCl). In each measurement step (S901), the consumption amount of AgCl (denoted by $C_{consume}$) is defined by calculating the area under the current curve of the working electrode W. The AgCl of the counter electrode R/C has a consumption amount $C_{consume}$ corresponding to the physiological signal Ia, i.e., $C_{consume}$=Ia*T1. In each replenishment step (S902), each replenishment amount (denoted by $C_{replenish}$) of AgCl is defined by calculating the area under the current curve of the counter electrode R/C, i.e., $C_{replenish}$=Ib*t2, where t2 is a value in a range of 0~T2.

The calculation method of AgCl safe storage amount is described below. In some preferred embodiments, the safe storage range is represented by the ratio of Ag to AgCl. The present invention uses the coulomb amount (C) measured at the counter electrode to reflect the ratio of Ag to AgCl. In some preferred embodiments, the ratio of Ag to AgCl is 99.9%:0.1%, 99%:1%, 95%:5%, 90%:10%, 70%:30%, 50%:50%, 40%:60% or 30:70%, which assure of a certain amount of the AgCl on the counter electrode without being exhausted, and thus each measurement step for measuring the physiological signal can be performed stably. The remaining amount of AgCl is the sum of the replenishment amount and the initial amount minus the consumption amount. In some preferred embodiments, the remaining amount of AgCl varies within a range, that is, the remaining amount of AgCl is controlled within a range of the initial amount plus or minus a specific value (X value). Namely, ($C_{replenish}$+$C_{initial}$)−$C_{consume}$=$C_{initial}$±X, where 0<X<100% $C_{initial}$, 10% $C_{initial}$<X≤90% $C_{initial}$, or 0.5% $C_{initial}$<X≤50% $C_{initial}$. In some preferred embodiments, the remaining amount of AgCl may, within a range, gradually decrease, gradually increase, change steadily, or change arbitrarily but still within the range.

Please refer to FIG. 10, which shows a method for measuring an analyte according to another embodiment of the present invention. Through this method, the usage lifetime of the micro biosensor can be prolonged and the amount of silver and silver halide materials of the counter electrode can be reduced. The micro biosensor, which may be, for example, the micro biosensor shown in FIG. 18A-18C and FIGS. 19A-19C, is used to be implanted subcutaneously to measure a physiological signal representative of a physiological parameter associated with the analyte in a biofluid (such as tissue fluid). The electrode material of the counter electrode of the micro biosensor includes silver and silver halide. In the embodiment of FIG. 10, the analyte can be glucose in tissue fluid, the physiological parameter is the glucose value in the human body, and the physiological signal is a current value measured by the micro biosensor. Only two cycles of this embodiment is described below. The method of this embodiment starts with the step of applying a measurement voltage to drive a first or a second working electrode W1/W2 during a first measurement period to measure a physiological signal for obtaining a physiological parameter, wherein silver halide on a first or a second counter electrode R/C1 or R/C2 (assuming the first counter electrode R/C1) is consumed by a consumption amount (S1101).

Then the step of applying the measurement voltage is stopped (S1102), and the obtained physiological signal is used to obtain a physiological parameter (S1103). After the physiological parameter is obtained, a replenishment voltage is applied during a first replenishment period to drive the counter electrode, i.e., the first counter electrode R/C1, used in the step S1101 and having the consumption amount, such that silver halide is replenished by a replenishment amount (S1104), wherein a value (i.e., the aforementioned "remaining amount") of a sum of the replenishment amount and an initial amount minus the consumption amount is controlled within a range of the initial amount plus or minus a specific value. The above control step is achieved by controlling the replenishment amount to be equal to or not equal to (including approximately similar, greater than or less than) the consumption amount so as to maintain the amount of silver halide within a safe storage range. According to the chemical equations, the increase or decrease of the mole number of silver halide corresponds to the increase or decrease of the mole number of silver. Therefore, for the ease of descriptions, the consumption amount of silver halide corresponds to a simulated increased amount of silver. In some preferred embodiments, a value of the remaining amount is controlled such that the ratio of the amount of silver halide to the sum of the amount of silver halide plus the amount of silver (AgCl/Ag+AgCl) is greater than 0 and less than 1 (which means that there should be a certain amount of silver halide in the counter electrode), preferably between 0.01-0.99, between 0.1-0.9, between 0.2-0.8, between 0.3-0.7, or between 0.4-0.6. When the replenishment amount is reached, the step of applying the replenishment voltage is stopped (S1105). Then the method returns to the step S1101, and a measurement voltage is applied to drive a first or a second working electrode W1/W2 during a second measurement period to measure another physiological signal for obtaining another physiological parameter, wherein silver halide on the other counter electrode (i.e., the second counter electrode R/C2) is consumed by a consumption amount. Then the step of applying the measurement voltage is stopped (S1102), and the obtained physiological signal is used to obtain a physiological parameter (S1103). After the physiological parameter is obtained, a replenishment voltage is applied during a second replenishment period to drive the counter electrode, i.e., the second counter electrode R/C2, used in the step S1101 and having the consumption amount, such that silver halide is replenished by a replenishment amount (S1104). Then the method returns to step S1101 to execute the next loop.

A specific embodiment of the present invention will be described below. Taking a usage lifetime of a biosensor must reach 16 days as an example. To this end, the method to calculate the required size of Ag/AgCl material on a signal sensing section of a electrode is described below. For example, the average of the measured current of the analyte for each measurement is 30 nA, the measurement period (T1) is 30 seconds, and the replenishment period (t2) is 30 seconds. The daily consumption amount of AgCl ($C_{consume/day}$)=1.3 mC/day. Assuming that the requirement of a usage lifetime of a biosensor is 16 days, the consumption amount of AgCl required for using 16 days is 1.3× 16=20.8 mC.

For example, the length of the counter electrode is 2.5 mm, which corresponds to the initial amount of AgCl $C_{initial}$=10 mC.

(5) On a condition that AgCl replenishment is not performed, for the sensor usage lifetime of 16 days, the required length of the counter electrode is at least:

$C_{16day}/C_{consume/day}$=20.8 mC/1.3 mg/day=16 mm.

(6) Therefore, on a condition that the replenishment method for the silver halide in the present application is not performed, the length of the counter electrode needs to exceed 16 mm in order to make the usage lifetime of the sensor achieve 16 days.

In this embodiment, on a condition that the replenishing technique for silver halide in the present invention is not used, the signal sensing section of the counter electrode needs to be configured with a relatively large size of Ag/AgCl material to achieve the usage lifetime of 16 days. Through the replenishment method for silver halide in the present invention, the replenishment step for silver halide is performed between two measurement steps. The consumption and replenishment of the silver halide cycles repeated in a short period of time (replenished when used), so the amount of Ag/AgCl material in the sensor can be reduced, and thereby the sensor is miniaturized. Therefore, there is no need to prepare 16 days of AgCl capacity for the signal sensing section material of the electrode for consumption. For example, the preparation of the capacity of AgCl for about 1-2 days can achieve a usage time of 16 days of the sensor. Thus, the present invention has the effect of prolonging the usage lifetime of the sensor. The capacity of AgCl for 1-2 days also refers to the initial amount of AgCl in the counter electrode before leaving the factory or before performing the first measurement. The initial amount of AgCl may be, for example, between about 1.3 and 2.6 mC, and can be in other smaller range or a larger range. In other embodiments, different AgCl capacities for 1-5 days, 1-3 days, 6-24 hours, and 6-12 hours can also be prepared. The size of the signal sensing section of the counter electrode can be configured in such a way that the counter electrode has a capacity which enables stable executions of each measurement step for glucose and the positive correlation between the measurement current and the glucose concentration in the body.

The prior art increased the electrode length/area to make the sensor reach the required measurement days without using the silver chloride replenishment technology of the present invention. For example, the length of the implantation end of the prior art is about 12 mm. Due to the long implantation length of the prior art, the implantation end needs to be implanted subcutaneous at an oblique angle to avoid the implantation end from implanting deeply into the subcutaneous tissue, which causes a large implantation wound. For another example, the capacity of AgCl for 1-2 days is about 1.3~2.6 mC, the length of the counter electrode for 1~2 days is 2.5~5 mm after conversion, and thus the length of the counter electrode needs 16 mm without using the replenishment method for silver halide in the present invention. Comparing to the example above, it is obvious that the present invention has more significant effect on shortening the size of the counter electrode. According to the silver chloride replenishment step of the present invention, the implantation end of the present invention can be shortened, for example, to no greater than 10 mm. Please refer to FIGS. 18A-18C, the lower half of the connecting area 417 to the second end 414 of the micro biosensor 400 of the present invention forms a short implantation end 418, as shown in FIGS. 18A and 18B. The implantation depth of the short implantation end 418 is at least a depth to the dermis where can measure the glucose concentration in the tissue fluid. According to the silver chloride replenishment step of the present invention, a length of the longest side of the short implantation end 418 is no greater than 6 mm, so that the short implantation end 418 of the micro biosensor 100 can be perpendicularly implanted under the biological epidermis. Preferably, the length of the longest side of the short implantation end 418 is no greater than 5 mm, 4.5 mm, 3.5 mm or 2.5 mm. The short implantation end 418 of the present invention includes the third signal sensing section 442 and the fourth signal sensing section 452, and lengths of the longest sides of the third signal sensing section 442 and the fourth signal sensing section 452 are no greater than 6 mm, preferably 2-6 mm, 2-5 mm, 2-4.5 mm, 2-3.5 mm, 0.5-2 mm or 0.2-1 mm.

Therefore, compared with the cases where the silver halide replenishment technique of the present invention is not used, the silver halide replenishment method of the present invention can effectively extend the micro sensor's usage lifetime, and can also greatly reduce the use of Ag/AgCl material on the counter electrode, which causes the size of the signal sensing section of the counter electrode to be reduced. Because of the reduced use of the Ag/AgCl material on the counter electrode, the sensor can be miniaturized and biological toxicity can be reduced. In addition, the reduced size of the electrode specifically refers to the shortened length of the implantation end of the sensor, which would reduce pain for the user during implantation. In the device including four electrodes in the present invention, because the measurement and replenishment can be performed at the same time, compared with the two-electrode or three-electrode devices, the device in the present invention can have a shorter counter electrode size and can be operated by more flexible and efficient manners.

Embodiment IV

For the purpose of reducing a dimension of the counter electrode, the amount of the silver halide on the counter electrode can be minimized to an initial amount sufficient to support at least one measurement of the biosensor. The dimension of the counter electrode is quantified based on the initial amount of the silver halide which is sufficient to deal with at least one measurement of a physiological signal of a physiological parameter associated with an analyte in a patient. After a first measurement, a replenishment period is performed to replenish the silver halide that is consumed. Therefore, a method for determining a dimension of a counter electrode of a biosensor and for prolonging a usage lifetime of the biosensor is provided.

Figure 24:
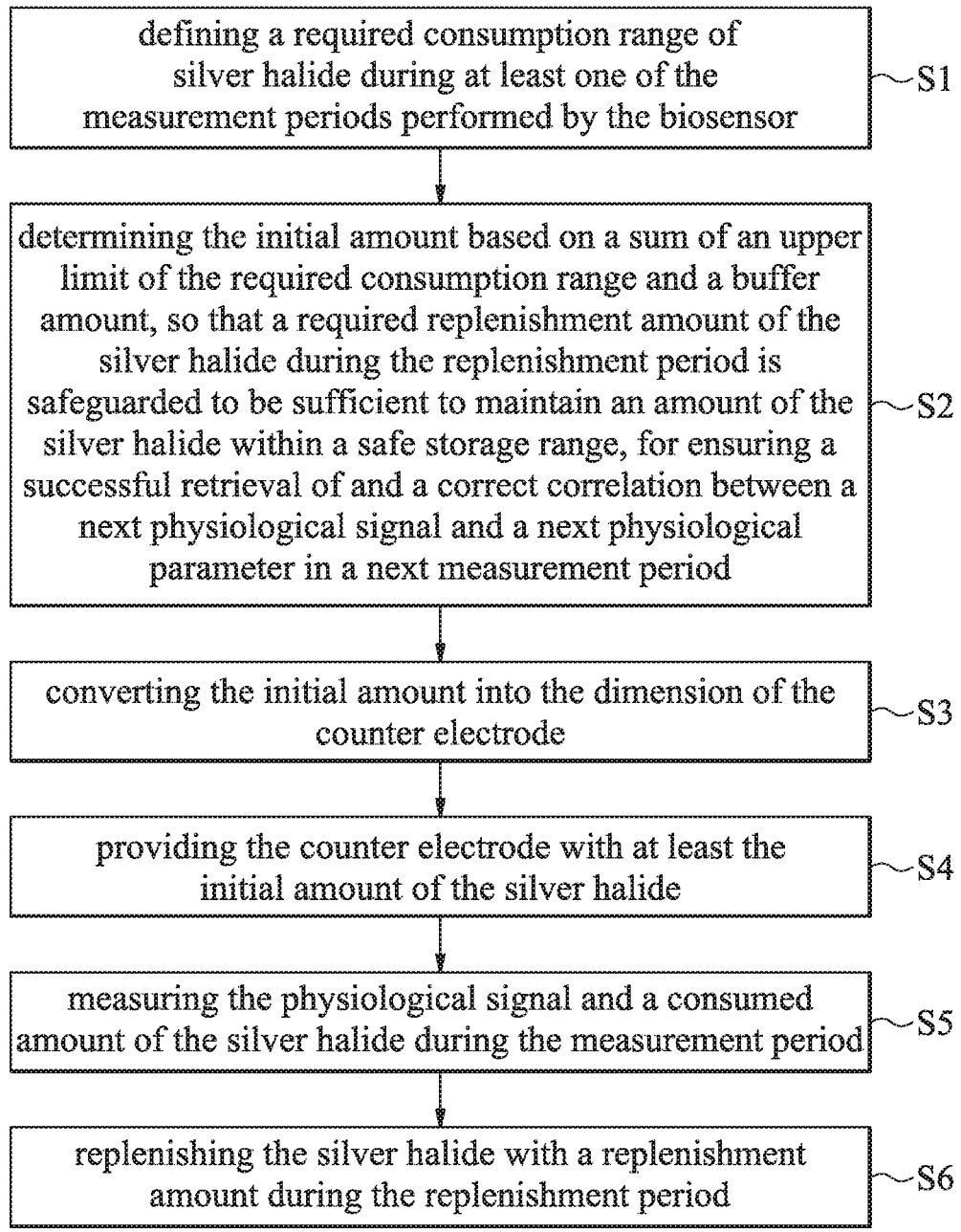
FIG. 24 is a flow diagram in accordance with one embodiment of the present disclosure.

As shown in FIG. 24, the method comprises the following steps: Step a: defining a required consumption range of the silver halide during at least one measurement period performed by the biosensor; Step b: determining the initial amount based on a sum of an upper limit of the required consumption range and a buffer amount, so that a required replenishment amount of the silver halide during the replenishment period is safeguarded to be sufficient to maintain an amount of the silver halide within a safe storage range, for ensuring a successful retrieval of and a correct correlation between a next physiological signal and a next physiological parameter in a next measurement period; Step c: converting the initial amount into the dimension of the counter electrode; Step d: providing the counter electrode with at least the initial amount of the silver halide; Step e: measuring the physiological signal and a consumption amount of the silver halide during the measurement period; and Step f: replenishing the silver halide with a replenishment amount during the replenishment period.

According to one embodiment of the present disclosure, the initial amount of the silver halide is readily prepared before the biosensor is ready for shipping out of the plant for sale. The silver halide can be coated on the counter electrode by printing a silver halide layer with the initial amount thereon, or by halogenating a silver layer coated thereon to have the initial amount of the silver halide.

In another embodiment of the present disclosure, before the biosensor is ready for shipping out of the plant for sale, the initial amount of the silver halide can be zero. In this case, the biosensor has no silver halide on the counter electrode. An initial amount of the silver halide can be replenished on the counter electrode by oxidizing the silver coated on the counter electrode during a very first replenishment period after the biosensor is implanted subcutaneously into the patient and before a first measurement is proceeded.

Normally, when a biosensor is implanted into a patient, the wound possibly caused to the skin and/or the subcutaneous tissues sometimes results in the signal monitored by the sensor to be unstable. In addition, before using the biosensor, the biosensor must be fully "wetted" or hydrated to balance with the analyte, such as the glucose in the biofluid, in the patient. Therefore, after implanting the biosensor into the living body, the user has to wait for a warming up period before the very first measurement for the biosensor to be ready for obtaining an accurate reading of the concentration of the analyte. Under the circumstance, because the biosensor needs the warm up period before measuring the analyte right after implanting into the living body, the very first replenishment period can be performed during the warm up period without delaying any desired measurement.

In order to realize how the initial amount of the silver halide is determined, an example of a calculation method is provided as follows. Defining a required consumption range of the silver halide during at least one measurement period performed by the biosensor, wherein the required consumption range is associated with the physiological parameter representative of the analyte. Taking one measurement of the glucose in the human body and silver halide is silver chloride as an example, an upper limit of a predetermined detection glucose concentration is chosen as a calculation benchmark. For example, the required consumption current obtained from one measurement of the physiological signal is 100 nA per second at a glucose concentration of, e.g., 600 mg/dL. If one measurement period lasts for 30 seconds, then the required consumption amount of the silver chloride is 3000 nC (or 0.003 mC), which is obtained by multiplying 100 nA by 30 sec. In this case, the upper limit of the required consumption amount of the silver chloride for one measurement can be chosen to be larger or equal to 0.003 mC. In another embodiment, the upper limit can be chosen to be another concentration value.

Due to the fact that the concentrations of the analyte in different patients, or that the concentrations of the analyte in the same patient at different times, can fluctuate to a large extent, the broader required consumption range of the silver halide is suggested accordingly, which means that a larger initial amount is required. Therefore, adding a buffer amount to the required consumption amount of the silver halide should be necessary for dealing with the fluctuation of the concentration of the analyte in the patient's body to maintain the amount of the silver halide on the counter electrode within a safe storage range, so that a stable correlation between a physiological signal and a physiological parameter in a next measurement period is kept. The buffer amount can be larger than 0 and is adjusted based on a predetermined usage period of the biosensor. The predetermined usage period of time can be any multiple of times, such as 1, 2, 4, 10 and 100 times of a measurement period of time, or a properly predetermined usage period of time can be chosen based on the biosensor, such as 1 hour, 2 hours, 6 hours, 1 day, 2 days, 3 days, 5 days and so on, so that a sufficient but minimized initial amount of the silver halide is prepared.

In addition to take one measurement as the calculation base for the required consumption range, the required consumption range can also be adjusted according to the predicted usage period of time of the biosensor to choose a plurality of measurement periods. A corresponding buffer amount is also adjusted according to the required consumption range, thereby the required initial amount of silver halide is adjusted.

In another embodiment of the present disclosure, an arithmetic mean, a geometric mean or a median of the required consumption range can also be used to replace the upper limit of the required consumption range for determining the initial amount, depending on the real situation that the biosensor may face. For example, it is known that an average electric current is 20 nA per second. If a measurement period lasts for 30 seconds, the required average consumption amount of the silver chloride in one measurement period is 600 nC (or 0.0006 mC), which is obtained by multiplying 20 nA by 30 sec. In this case the required average consumption amount of the chloride is 0.0006 mC.

Similarly, in consideration that the concentrations of the analyte of different patients, or that the concentrations of the same patient at different times, can fluctuate to a large extent, and there are a lot of the environmental factors in vivo, a broader required consumption range (i.e. a larger initial amount is required) of the silver halide is suggested.

If the measurement period is performed once every 1 minute and one measurement lasts for 30 sec, there will be 1440 measurements in a day. That is, the required consumption amount of the silver chloride for one day is 0.864 mC, which is obtained by multiplying 0.0006 mC by 1440 times per day, which is close to 1 mC. Therefore, the value 1 mC can be chosen to determine the initial amount of the silver chloride.

In the above-mentioned embodiments, the required consumption amount range of the silver halide and the buffer amount can be adjusted based on the predetermined usage period of time of the biosensor. The predetermined usage period of time can be any multiple of, such as 1, 2, 4, 10 and 100 times of, one measurement period of time, or a proper predetermined usage period of time chosen based on the biosensor, such as 1 hour, 2 hours, 6 hours, 1 day, 2 day, 3 days, 5 days and so on, so that a sufficient but minimized initial amount of the silver halide is prepared.

Due to the fact that the average electric current required for one measurement for each of the biosensors depends on the designs and characteristics of the biosensors produced by different makers, the required consumption range of the silver halide also depends on different biosensors. Therefore, It can be realized that any modification to the required consumption amount is within the scope of the present invention.

In addition to the required consumption range of the silver halide, an added buffer amount may further be considered for dealing with the fluctuation of the concentrations of the analyte in a patient. The buffer amount can be larger than 0 and is adjusted based on a predetermined usage period of the biosensor. The required consumption amount can be adjusted based on a plurality of the measurement periods in a predetermined usage period of the biosensor.

The initial amount can be determined based on a sum of an upper limit of the required consumption range and a buffer amount, so that a required replenishment amount of the silver halide during the replenishment period is safeguarded to be sufficient to maintain an amount of the silver halide within a safe storage range, for ensuring a successful retrieval of and a correct correlation between a next physiological signal and a next physiological parameter in a next measurement period. The buffer amount can be zero in case the replenishment amount of the silver halide is controlled to be sufficient to support the consumption amount in the next measurements.

In case the upper limit of the required consumption range of the silver chloride being 1 mC is chosen and the buffer amount being 0.5 mC is chosen, the initial amount of the silver chloride on the counter electrode can be determined to be 1.5 mC, which is the sum of 1 mC and 0.5 mC. Accordingly, the required replenishment amount range can be greater than zero, greater than 1.5 mC or less than 1.5 mC.

Based on the initial amount of the silver halide, at least the first measurement can be performed. After the first measurement is performed, a first replenishment is performed to replenish the silver halide that is consumed.

After the initial amount is determined, the required dimension of the counter electrode are determined accordingly. The dimension of the counter electrode is related to the total volume of the silver and the silver halide on the counter electrode. The initial amount of the silver halide can be transformed into the total volume of the silver halide on the counter electrode. The total volume of the silver and the silver halide is simply defined by an arithmetic product of a width, a length and a thickness of the silver and the silver halide on the counter electrode. Any one of the width, length and thickness can be adjusted to change the volume of the silver and the silver halide. Normally, the width and the thickness of the silver and the silver halide on the counter electrode is pre-determined to meet the limitation of the design and the manufacturing capability. Therefore, the volume of the silver and the silver halide on the counter electrode can be reduced by reducing the length of the silver and the silver halide on the counter electrode, which means that the length of the counter electrode can be shortened. Accordingly, a biosensor having a prolonged usage lifetime with a short counter electrode can be achieved by utilizing the method of determining the initial amount of the silver halide provided by the present disclosure. The patient will suffer from much less pain and discomfort caused by the implanted biosensor, and does not need to buy a new biosensor to replace the old one too frequently.

According to one embodiment of the present disclosure, when the initial amount of the silver halide for one day is 1.5 mC, in case the unit amount (or unit capacity) of the silver halide, which varies depending on the characteristics of the biosensors of different makers, is 300 mC/mm$^3$, the required volume of the silver halide is 0.005 mm$^3$. When the width of the counter electrode is 0.3 mm and the thickness of the silver halide is 0.01 mm, the length of the silver halide on the counter electrode is 1.67 mm. Proportionally, if the initial amount of the silver halide is required for 3.6 days, the length of the silver halide, i.e. the length of the counter electrode is approximately 6 mm, and if the initial amount of the silver halide is required for 6 days, the length of the counter electrode is approximately 10 mm. Because the length of the counter electrode can be shortened, the length of the biosensor implanted into the patient can be shortened accordingly, and a vertical implantation of the biosensor to the patient is also possible in order to minimize the wound to the patient. Therefore, not only the usage lifetime of the biosensor can be prolonged because of the replenishment periods provided by the present disclosure, but also the pains and discomfort caused to the patient can be reduced because of the shortened length of the counter electrode.

Of course, the reduction to the volume of the silver and the silver halide can be achieved by modifying at least one of the length, width and thickness of the silver and silver halide. All of the above modifications are still within the scope of the present disclosure.

The present disclosure is also applicable for the biosensor having any number of the counter electrodes and any number of the working electrodes, such as the biosensor having one working electrode, one auxiliary electrode and having one counter electrode, two working electrodes and one counter electrode, or having two working electrodes and two counter electrodes. If the biosensor has two or more counter electrodes, all of the counter electrodes can have the same dimension, and/or the same initial amount of the silver halide.

Embodiments

Group 1

1. A method of measuring an analyte using a biosensor for prolonging a usage lifetime of the biosensor implanted subcutaneously to measure a physiological signal representative of a physiological parameter associated with the analyte in a biofluid, the biosensor comprising a working electrode and a counter electrode, the working electrode being at least partially covered by a chemical reagent configured to react with the analyte, the counter electrode having a silver and a silver chloride, the method comprising the following cyclic steps of:

a) performing a measurement step, including sub-steps of:

i. applying a measurement potential difference across the working electrode and the counter electrode so that the working electrode has a higher voltage than that of the counter electrode during a measurement period, causing a first oxidation reaction to occur on the working electrode having an electrochemical reaction with the chemical reagent and the analyte, thereby the working electrode outputting a physiological signal, where the silver halide of the counter electrode has a consumption amount corresponding to the physiological signal; and ii. removing the measurement potential difference to stop the physiological signal measurement step, and converting the physiological signal to output a physiological parameter; and b) performing a replenishment step, including sub-steps of:

i. applying a replenishment potential difference across the counter electrode and the working electrode during a replenishment period so that the counter electrode has a higher voltage than that of the working electrode, causing a second oxidation reaction to occur to the silver on the counter electrode, so that the silver chloride gains a replenishment amount, wherein the replenishment amount is related to the consumption amount that the silver halide of the counter electrode has an amount maintained in a safe storage range, and a next physiological signal and a next physiological parameter obtained in a next measurement step are kept in a stable correlation; and ii. removing the replenishment potential difference to stop the replenishment step.

2. The method according to claim 1, wherein the measurement potential difference and the replenishment potential difference are applied for a measurement time period and a replenishment time period respectively, and the measurement time period has a time value being one of a constant measurement time period value or a variable measurement time period value.

3. The method according to claim 2, wherein a total time period of the measurement time period plus the replenishment time period is a constant.

4. The method according to claim 2, wherein the replenishment potential difference has a constant voltage value, and the replenishment time period is dynamically adjusted based on the consumption amount of the silver halide.

5. The method according to claim 2, wherein the replenishment time period has a constant time period value, and the replenishment potential difference has a value dynamically adjusted based on the consumption amount of the silver halide.

6. The method according to claim 2, wherein the constant measurement time period is a time value being no greater than one selected from the group consisting of 15 seconds, 30 seconds, 1 minute, 2 minutes, 5 minutes and 10 minutes.

7. The method according to claim 1, wherein the amount of the silver chloride of the counter electrode in the safe storage range is maintained by controlling the replenishment amount to be close to or equal to the consumption amount.

8. The method according to claim 1, wherein the amount of the silver chloride of the counter electrode in the safe storage range is maintained by controlling the replenishment amount to be larger than the consumption amount.

9. The method according to claim 1, wherein the amount of the silver chloride of the counter electrode in the safe storage range is maintained by controlling the replenishment amount to be smaller than the consumption amount.

10. The method according to claim 1, wherein the amount of the silver chloride of the counter electrode in the safe storage range is maintained by controlling the replenishment amount to be unequal to the consumption amounts.

11. A method of measuring an analyte using a biosensor for prolonging a usage lifetime of the biosensor implanted subcutaneously to measure a physiological signal representative of a physiological parameter associated with the analyte in a biofluid, the biosensor comprising a working electrode and a counter electrode, the working electrode being at least partially covered by a chemical reagent, the counter electrode including a silver and a silver halide having an initial amount, the method comprising cyclic steps of:
applying a measurement voltage to drive the working electrode to measure the physiological signal, thereby obtaining the physiological parameter, where the silver halide is consumed a specific amount;
stopping applying the measurement voltage; and
whenever the physiological parameter is obtained, applying a replenishment voltage to drive the counter electrode to cause an oxidation reaction, thereby the silver halide of a replenishment amount being replenished to the counter electrode,
wherein a guarding value of a sum of the replenishment amount and the initial amount subtracting the consumption amount is controlled within a range of the initial amount plus or minus a specific value.

12. The method according to claim 11, wherein the specific value is X, and the X satisfies a condition of: 0<X<100% of the initial amount.

13. The method according to claim 11, wherein the measurement voltage is applied for a measurement time period, the replenishment voltage is applied for a replenishment time period, and the measurement time period has a time value being one of a constant measurement time period value and a variable measurement time period value.

14. The method according to claim 13, wherein the replenishment voltage has a constant voltage value, and the replenishment time period is dynamically adjusted based on the consumption amount of the silver halide.

15. The method according to claim 13, wherein the replenishment time period has a constant time value, and the replenishment voltage has a value dynamically adjusted based on the consumption amount of the silver halide.

16. The method according to claim 11, wherein the guarding value is secured by controlling the replenishment amount of the silver halide at one selected from the group consisting of being close to, equal to, larger than, smaller than, and unequal to the consumption amount of the silver halide to maintain an amount of the silver halide in a safe storage range.

17. A micro biosensor for implanting subcutaneous implantation to measure a physiological parameter representative of a physiological signal associated with an analyte in a living body, comprising:
a substrate;
a chemical reagent;
a working electrode disposed on the substrate, at least partially covered by the chemical reagent, and driven for a first oxidation reaction to measure the physiological signal for obtaining the physiological parameter within a measurement period;
a counter electrode disposed on the substrate, and including a silver and a silver halide having an initial amount and being consumed in a specific amount within the measurement period; and
whenever the respective physiological parameter is obtained, driving the counter electrode for a second oxidation reaction within a replenishment period, thereby the silver halide of a replenishment amount being replenished to the counter electrode,
wherein a guarding value of a sum of the replenishment amount and the initial amount subtracting the consumption amount is controlled within a range of the original amount plus or minus a specific value.

18. The biosensor according to claim 17, wherein the guarding value is controlled so that a ratio of an amount of the silver halide and a sum of an amount of the silver and the amount of the silver halide is larger than 0 and smaller than 1.

19. The biosensor according to claim 17, further comprising a short implantation end having a length no greater than 6 mm.

20. The biosensor according to claim 17, wherein the counter electrode is at least partially covered by the chemical reagent.

Group 2
1. A method of measuring an analyte using a biosensor for prolonging a usage lifetime of the biosensor implanted subcutaneously to measure a physiological signal representative of a physiological parameter associated with the analyte in a biofluid, the biosensor comprising a working electrode, a counter electrode and an auxiliary electrode, the working electrode being at least partially covered by a chemical reagent configured to react with the analyte, the counter electrode having a silver and a silver halide, the method comprising the following steps of:

a) performing a measurement step, including sub-steps of:
i. applying a measurement potential difference across the working electrode and the counter electrode so that the working electrode has a higher voltage level than that of the counter electrode during a measurement period, for causing a first oxidation reaction to occur on the working electrode having an electrochemical reaction with the chemical reagent and the analyte to output a current physiological signal, where the silver halide of the counter electrode has a current consumption amount corresponding to the current physiological signal; and
ii. removing the measurement potential difference to stop the measurement step, and operating the current physiological signal to output a current physiological parameter;

b) performing a replenishment step, including sub-steps of:
i. applying a replenishment potential difference across the counter electrode and the auxiliary electrode during a replenishment period so that the counter electrode has a higher voltage level than that of the auxiliary electrode, causing a second oxidation reaction to occur to the silver on the counter electrode, so that the silver halide gains a replenishment amount corresponding to the consumption amount so that the silver halide of the counter electrode has an amount maintained in a safe storage range, and a next physiological signal and a next physiological parameter obtained in a next measurement step are kept in a specific correlation; and
ii. removing the replenishment potential difference to stop the replenishment step;

c) performing a next measurement step including the same sub-steps as those in the step a); and
d) performing a next replenishment step including the same sub-steps as those in the step b).

2. The method according to claim 1, wherein the measurement potential difference and the replenishment potential difference are applied for a measurement time period and a replenishment time period respectively, and the measurement time period has a time value being one of a constant measurement time period value or a variable measurement time period value.

3. The method according to claim 2, wherein a total time period of the measurement time period plus the replenishment time period is a constant.

4. The method according to claim 2, wherein the replenishment potential difference has a constant voltage value, and the replenishment time period is dynamically adjusted based on the consumption amount of the silver halide.

5. The method according to claim 2, wherein the replenishment time period has a constant time period value, and the replenishment potential difference has a value dynamically adjusted based on the consumption amount of the silver halide.

6. The method according to claim 2, wherein the constant measurement time period is a time value being no greater than one selected from the group consisting of 3 seconds, 5 seconds, 10 seconds, 15 seconds, 30 seconds, 1 minute, 2 minutes, 5 minutes and 10 minutes.

7. The method according to claim 1, wherein the amount of the silver halide of the counter electrode in the safe storage range is maintained by controlling the replenishment amount to be close to or equal to the consumption amount.

8. The method according to claim 1, wherein the amount of the silver halide of the counter electrode in the safe storage range is maintained by controlling the replenishment amount to be larger than the consumption amount.

9. The method according to claim 1, wherein the amount of the silver halide of the counter electrode in the safe storage range is maintained by controlling the replenishment amount to be smaller than the consumption amount.

10. The method according to claim 1, wherein the amount of the silver halide of the counter electrode in the safe storage range is maintained by controlling the replenishment amount to be unequal to the consumption amount.

11. A method of measuring an analyte using a biosensor for prolonging a usage lifetime of the biosensor implanted subcutaneously to measure a physiological signal representative of a physiological parameter associated with the analyte in a biofluid, the biosensor comprising a working electrode, a counter electrode and an auxiliary electrode, the working electrode being at least partially covered by a chemical reagent, the counter electrode including a silver and a silver halide having an initial amount, the method comprising cyclic steps of:

applying a measurement voltage to drive the working electrode to measure the physiological signal, thereby obtaining the physiological parameter, where the silver halide is consumed by a consumption amount;

stopping applying the measurement voltage; and whenever the physiological parameter is obtained, applying a replenishment voltage between the counter electrode and the auxiliary electrode to drive the counter electrode to cause an oxidation reaction, thereby the silver halide of a replenishment amount being replenished to the counter electrode, wherein a guarding value of a sum of the replenishment amount and the initial amount subtracting therefrom the consumption amount is controlled within a range of the initial amount plus or minus a specific value.

12. The method according to claim 11, wherein the measurement voltage is applied for a measurement time period, the replenishment voltage is applied for a replenishment time period, and the measurement time period has a time value being one of a constant measurement time period value and a variable measurement time period value.

13. The method according to claim 12, wherein the replenishment voltage has a constant voltage value, and the replenishment time period is dynamically adjusted based on the consumption amount of the silver halide.

14. The method according to claim 12 wherein the replenishment time period has a constant time value, and the replenishment voltage has a value dynamically adjusted based on the consumption amount of the silver halide.

15. The method according to claim 11, wherein the guarding value is secured by controlling the replenishment amount of the silver halide at one selected from the group consisting of being close to, equal to, larger than, smaller than, and unequal to the consumption amount of the silver halide to maintain an amount of the silver halide in a safe storage range.

16. The method according to claim 11, wherein the specific value is X, and the X satisfies a condition of: 0<X<100% of the initial amount.

17. A micro biosensor for subcutaneous implantation to measure a physiological parameter representative of a physiological signal associated with an analyte in a living body, comprising:
a substrate;
a chemical reagent;
a working electrode disposed on the substrate, at least partially covered by the chemical reagent, and being driven for a first oxidation reaction to measure the physiological signal to obtain the physiological parameter within a measurement period;
a counter electrode disposed on the substrate, and including a silver and a silver halide having an initial amount and being consumed with a specific amount within the measurement period; and
an auxiliary electrode disposed on the substrate, wherein:
whenever the respective physiological parameter is obtained, driving the counter electrode and the auxiliary electrode for a second oxidation reaction within a replenishment period, thereby the silver halide of a replenishment amount being replenished to the counter electrode,
wherein a guarding value of a sum of the replenishment amount and the initial amount subtracting therefrom the consumption amount is controlled within a range of the original amount plus or minus a specific value.

18. The biosensor according to claim 17, wherein the guarding value is controlled so that a ratio of an amount of the silver halide and a sum of an amount of the silver and the amount of the silver halide is larger than 0 and smaller than 1.

19. The biosensor according to claim 17, further comprising a short implantation end having a length no greater than 6 mm.

20. The biosensor according to claim 17, wherein the counter electrode is at least partially covered by the chemical reagent, and the auxiliary electrode includes a platinum.

Group 3

1. A method of measuring an analyte using a biosensor for prolonging a usage lifetime of the biosensor implanted subcutaneously to measure a physiological signal representative of a physiological parameter associated with the analyte in a biofluid, the biosensor comprising a first working electrode, a second working electrode, a first counter electrode and a second counter electrode, each working electrode being at least partially covered by a chemical reagent configured to react with the analyte, each counter electrode having a silver and a silver halide, the method comprising the following steps of:
a) performing a first measurement step, including sub-steps of:
i. applying a first measurement potential difference across the first working electrode and the first counter electrode so that the first working electrode has a higher voltage level than that of the first counter electrode during a first measurement period, for causing a first oxidation reaction to occur on the first working electrode having an electrochemical reaction with the chemical reagent and the analyte, thereby the first working electrode outputting a first physiological signal, where the silver halide of the first counter electrode has a first consumption amount corresponding to the first physiological signal; and
ii. removing the first measurement potential difference to stop the first measurement step, and operating the first physiological signal to output a first physiological parameter;
b) performing a first replenishment step, including sub-steps of:
i. applying a first replenishment potential difference across the first counter electrode and one of the first and the second working electrodes during a first replenishment period so that the first counter electrode has a higher voltage level than that of the one of the first and the second working electrodes, for causing a second oxidation reaction to occur to the silver on the first counter electrode so that the silver halide gains a first replenishment amount corresponding to the first consumption amount; and
ii. removing the first replenishment potential difference to stop the first replenishment step;
c) performing a second measurement step, including sub-steps of:
i. applying a second measurement potential difference across one of the first and the second working electrodes and the second counter electrode so that the one of the first and the second working electrodes has a higher voltage level than that of the second counter electrode during a second measurement period, for causing the first oxidation reaction to occur on the one of the first and the second working electrodes having the electrochemical reaction with the chemical reagent and the analyte, thereby the one of the first and the second working electrodes outputting a second physiological signal, where the silver halide of the second counter electrode has a second consumption amount corresponding to the second physiological signal; and
ii. removing the second measurement potential difference to stop the second measurement step, and operating the second physiological signal to output a second physiological parameter;
d) performing a second replenishment step, including sub-steps of:
i. applying a second replenishment potential difference across the second counter electrode and the second working electrode during a second replenishment period so that the second counter electrode has a higher voltage level than that of the second working electrode, for causing the second oxidation reaction to occur to the silver on the second counter electrode so that the silver halide gains a second replenishment amount; and
ii. removing the second replenishment potential difference to stop the second replenishment step; and
e) repeatedly performing steps like the steps a-b), or c)-d), wherein:
the silver halide of each counter electrode has an amount maintained in a safe storage range so that a next physiological signal and a next physiological parameter obtained in a next measurement step are kept in a specific correlation.

2. The method according to claim 1, wherein each of the first and the second measurement time periods has a measurement time having a time value being a constant measurement time value or a variable measurement time value, and each of the first and the second replenishment time periods has a replenishment time.

3. The method according to claim 2, wherein each of the first and the second replenishment potential differences has a constant voltage value, and each of the replenishment times is dynamically adjusted based on a consumption amount of the silver halide during the corresponding measurement time period.

4. The method according to claim 2, wherein each of the first and the second replenishment times has a constant time value, and each of the replenishment potential differences has a value dynamically adjusted based on a consumption amount of the silver halide during the corresponding measurement time period.

5. The method according to claim 1, wherein the amount of the silver halide of each counter electrode in the safe storage range is maintained by controlling each replenishment amount to be close to or equal to each consumption amount.

6. The method according to claim 1, wherein the amount of the silver halide of each counter electrode in the safe storage range is maintained by controlling the corresponding replenishment amount to be larger than each consumption amount.

7. The method according to claim 1, wherein the amount of the silver halide of each counter electrode in the safe storage range is maintained by controlling the corresponding replenishment amount to be smaller than each consumption amount.

8. The method according to claim 1, wherein the amount of the silver halide of each counter electrode in the safe storage range is maintained by controlling the corresponding replenishment amount to be unequal to each consumption amount.

9. The method according to claim 1, wherein a first content of the silver halide of the first counter electrode at any time is calculated as a first ratio of an amount of the silver halide of the first counter electrode and a sum of an amount of the silver and the amount of the silver halide of the first counter electrode, a second content of the silver halide of the second counter electrode at any time is calculated as a second ratio of an amount of the silver halide of the second counter electrode and a sum of an amount of the silver and the amount of the silver halide of the second counter electrode, and each of the first ratio and the second ratio is a value larger than 0 and smaller than 1.

10. The method according to claim 1, wherein the first measurement period and the second replenishment period are one of the same, independent of each other and partially overlapping, and the first replenishment period and the second measurement period are one of the same time, independent of each other and partially overlapping.

11. A method of measuring an analyte using a biosensor for prolonging a usage lifetime of the biosensor implanted subcutaneously to measure a physiological signal representative of a physiological parameter associated with the analyte in a biofluid, the biosensor comprising two working electrodes and two counter electrodes disposed on a substrate, each working electrode being at least partially covered by a chemical reagent, each counter electrode including an electrode material having a silver and a silver halide, each silver halide having an initial amount, the method comprising cyclic steps of:

applying a measurement voltage to drive one of the two working electrodes at a measurement period to measure the physiological signal, thereby obtaining the physiological parameter, wherein the silver halide of one of the two working electrodes is consumed by a consumption amount;

stopping applying the measurement voltage; and applying a replenishment voltage to drive the consumed counter electrode at a replenishment period to replenish the silver halide of a replenishment amount to the consumed counter electrode, wherein:

whenever the physiological parameter is obtained, within the replenishment period, a guarding value of a sum of the replenishment amount and the initial amount subtracting the consumption amount is controlled within a range of the initial amount plus or minus a specific value.

12. The method according to claim 11, wherein the guarding value is X, and the X satisfies a condition of: $0<X<100\%$ of the initial amount.

13. The method according to claim 11, wherein the guarding value is secured by controlling the replenishment amount being close to or equal to the consumption amount to maintain an amount of the silver halide in a safe storage range.

14. The method according to claim 11, wherein the guarding value is secured by controlling the replenishment amount being larger than the consumption amount to maintain an amount of the silver halide in a safe storage range.

15. The method according to claim 11, wherein the guarding value is secured by controlling the replenishment amount being smaller than the consumption amount to maintain an amount of the silver halide in a safe storage range.

16. The method according to claim 11, wherein the guarding value is secured by controlling the replenishment amount being unequal to the consumption amount to maintain an amount of the silver halide in a safe storage range.

17. The method according to claim 11, wherein each initial amount is calculated as a ratio of an amount of the silver halide of the respective counter electrode and a sum of an amount of the silver and the amount of the silver halide of the respective counter electrode, and the ratio is a value larger than 0 and smaller than 1, and the measurement period is independent of another measurement period.

18. An implantation micro biosensor with relatively long usage lifetime and relatively small size of counter electrode for measuring a physiological parameter representative of a physiological signal associated with an analyte in a living body, comprising:

a substrate;

a chemical reagent;

two working electrodes disposed on the substrate, wherein each of the working electrodes includes a first signal sensing section at least partially covered by the chemical reagent, and one of the two working electrodes is driven for an oxidation reaction to measure the physiological signal to obtain the physiological parameter within a specific measurement period; and two counter electrodes disposed on the substrate, wherein each of the counter electrodes includes a second signal sensing section having a size and a electrode material having a silver and a silver halide, and the silver halide has an initial amount and is consumed with a consumption amount within the specific measurement period, wherein:

whenever the respective physiological parameter is obtained, one of the counter electrodes is driven within a replenishment period, thereby the silver halide of a replenishment amount being replenished to the driven counter electrode, wherein a guarding value of a sum of the replenishment amount and the initial amount subtracting the consumption amount is controlled within a range of the original amount plus or minus a specific value.

19. The implantation micro biosensor according to claim 18, wherein the guarding value is controlled so that a ratio of an amount of the silver halide and a sum of an amount of the silver and the amount of the silver halide is larger than 0 and smaller than 1, each counter electrode is at least partially covered by the chemical reagent, and the measurement period is independent of another measurement period.

20. The implantation micro biosensor according to claim 18, wherein the size of the two counter electrodes is so adjusted that the amount of the silver halide is maintained in a safe range and a length of the second signal sensing section is no greater than 6 mm, and any two adjacent measurement periods include a former measurement period and a latter measurement period, one of the two working electrodes and one of the two counter electrodes are driven within the former measurement period, and one of the two working electrodes is driven within the latter measurement period.

While the present disclosure has been described in terms of what is presently considered to be the most practical and preferred embodiments, it is to be understood that the present disclosure need not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for determining a dimension of a counter electrode of a biosensor and for prolonging a usage lifetime of the biosensor, wherein the counter electrode comprises a silver and a silver halide, the dimension is quantified based on an initial amount of the silver halide being sufficient to measure a physiological signal representative of a physiological parameter associated with an analyte in a living body, the biosensor is implanted subcutaneously into the living body and further includes a working electrode and an auxiliary electrode, and the silver halide is consumed during a measurement period and replenished during a replenishment period, the method comprising the following steps of:

a. defining a required consumption range of the silver halide during at least one of multiple measurement periods performed by the biosensor, wherein the required consumption range is defined based on a predetermined consumption current and a predetermined length of the measurement period;

b. determining the initial amount based on a sum of an upper limit of the required consumption range and a buffer amount, so that a required replenishment amount of the silver halide during the replenishment period is safeguarded to be sufficient to maintain an amount of the silver halide within a safe storage range, for ensuring a successful retrieval of and a correct correlation between a next physiological signal and a next physiological parameter in a next measurement period;

c. converting the initial amount into the dimension of the counter electrode;

d. providing the counter electrode with at least the initial amount of the silver halide;

e. measuring the physiological signal and calculating a consumption amount of the silver halide during the measurement period;

f. replenishing the silver halide with a replenishment amount during the replenishment period;

g. during the measurement period, applying a measurement voltage between the working electrode and the counter electrode to drive the working electrode to measure the physiological signal to obtain the physiological parameter;

h. stopping applying the measurement voltage, before which the silver halide is consumed;

i. during the replenishment period, applying a replenishment voltage between the counter electrode and the working electrode, thereby the silver halide gaining the replenishment amount;

j. during a second measurement period, applying the measurement voltage between the working electrode and the counter electrode to drive the working electrode to measure the physiological signal to obtain the physiological parameter;

k. stopping applying the measurement voltage, wherein when the measurement voltage is applied, the silver halide is consumed; and l. during a second replenishment period, applying a replenishment voltage between the counter electrode and the auxiliary electrode, thereby the silver halide gaining the replenishment amount.

2. The method according to claim 1, wherein the required consumption range is associated with the physiological parameter.

3. The method according to claim 1, wherein the required consumption range is adjusted based on the multiple measurement periods in a predetermined usage period of the biosensor.

4. The method according to claim 1, wherein the buffer amount is larger than 0 and is adjusted based on a predetermined usage period of the biosensor.

5. The method according to claim 1, wherein the step d is completed before the biosensor is shipped out for sale.

6. The method according to claim 1, wherein maintaining the amount of the silver halide within the safe storage range during the replenishment period is to keep a sum of the replenishment amount and the initial amount subtracting therefrom the consumption amount controlled within a range of the initial amount plus or minus a specific value.

7. The method according to claim 6, wherein the specific value is X in the 0<X<100% of the initial amount.

8. A method for determining a dimension of a counter electrode of a biosensor and for prolonging a usage lifetime of the biosensor, wherein the counter electrode comprises a silver and a silver halide, the dimension is quantified based on an initial amount of the silver halide being sufficient to measure a physiological signal representative of a physiological parameter associated with an analyte in a living body, the biosensor is implanted subcutaneously into the living body and further includes a working electrode and an auxiliary electrode, and the silver halide is consumed during a measurement period and replenished during a replenishment period, the method comprising the following steps of:

a. defining a required consumption range of the silver halide during at least one of multiple measurement periods performed by the biosensor, wherein the required consumption range is defined based on a predetermined consumption current and a predetermined length of the measurement period;

b. determining the initial amount based on a sum of an upper limit of the required consumption range and a buffer amount, so that a required replenishment amount of the silver halide during the replenishment period is safeguarded to be sufficient to maintain an amount of the silver halide within a safe storage range, for ensuring a successful retrieval of and a correct correlation between a next physiological signal and a next physiological parameter in a next measurement period;

c. converting the initial amount into the dimension of the counter electrode;

d. providing the counter electrode with at least the initial amount of the silver halide;

e. measuring the physiological signal and calculating a consumption amount of the silver halide during the measurement period;

f. replenishing the silver halide with a replenishment amount during the replenishment period;

g. during the measurement period, applying a measurement voltage between the working electrode and the counter electrode to drive the working electrode to measure the physiological signal to obtain the physiological parameter;

h. stopping applying the measurement voltage, before which the silver halide is consumed;

i. during the replenishment period, applying a replenishment voltage between the counter electrode and the working electrode, thereby the silver halide gaining the replenishment amount;

j. during a second measurement period, applying the measurement voltage between the working electrode and the counter electrode to drive the working electrode to measure the physiological signal to obtain the physiological parameter;

k. stopping applying the measurement voltage, wherein when the measurement voltage is applied, the silver halide is consumed; and l. during a second replenishment period, applying a replenishment voltage between the counter electrode and the auxiliary electrode, thereby the silver halide gaining the replenishment amount, wherein the step d is implemented before the step e after the biosensor is implanted, wherein the step d is implemented before the step e after the biosensor is implanted.

9. A physiological signal measurement device for measuring a physiological signal representative of a physiological parameter associated with an analyte, comprising:

a biosensor, comprising:

a working electrode configured to be driven for measuring the physiological signal during a first measurement period;

a counter electrode including a silver and a silver halide having an initial amount, wherein the counter electrode is configured to consume the silver halide in a consumption amount during the first measurement period, and during a first replenishment period, the counter electrode and the working electrode are configured to be driven to replenish the silver halide;

an auxiliary electrode configured to replace the working electrode to be driven to replenish the silver halide during the first replenishment period; and a circuit configured to drive the working electrode and the counter electrode during the first replenishment period and control a required replenishment amount range of the silver halide within a safe storage range, wherein the safe storage range is defined by a sum of an upper limit of a required consumption range and a buffer amount, and the required consumption range of the silver halide is defined based on a predetermined consumption current and a predetermined length of a specific measurement period performed by the physiological signal measurement device.

10. The physiological signal measurement device according to claim 9, further comprising a second working electrode and a second counter electrode having a second silver and a second silver halide, wherein:

during a second measurement period, the second working electrode and the second counter electrode are driven to measure the physiological signal; and during a second replenishment period, the second working electrode and the second counter electrode are driven to replenish the second silver halide on the second counter electrode.

11. The physiological signal measurement device according to claim 9, further comprising a second working electrode and a second counter electrode having a silver and a silver halide, wherein:

during a second measurement period, the working electrode and the second counter electrode are configured to be driven to measure the physiological signal; and during a second replenishment period, the second working electrode and the second counter electrode are configured to be driven to replenish the silver halide on the second counter electrode.

12. The physiological signal measurement device according to claim 9, wherein the counter electrode has a length defined based on the initial amount.

13. The physiological signal measurement device according to claim 12, wherein the length is not greater than 6 mm so that the biosensor is configured to be implanted vertically to a skin of a living body.

14. The physiological signal measurement device according to claim 12, wherein the length is not greater than 10 mm.

15. The physiological signal measurement device according to claim 9, wherein the biosensor is configured to be implanted into a living body.

* * * * *